(12) United States Patent
Fetell et al.

(10) Patent No.: US 9,682,033 B2
(45) Date of Patent: Jun. 20, 2017

(54) METHODS OF TREATING POSTHERPETIC NEURALGIA WITH A TOPICAL FORMULATION OF A SPIRO-OXINDOLE COMPOUND

(71) Applicant: Teva Pharmaceuticals International GmbH, Jona (CH)

(72) Inventors: Michael Fetell, Miami Beach, FL (US); Richard Malamut, Rose Valley, PA (US); Michael J. Lamson, Cary, NC (US); Ofer Spiegelstein, Ramat Hasharon (IL); Yigal Paul Goldberg, Vancouver (CA); Nicola Anne Price, Qualicum Beach (CA)

(73) Assignee: Teva Pharmaceuticals International GmbH, Jona (CH)

( * ) Notice: Subject to any disclaimer, the term of this patent is extended or adjusted under 35 U.S.C. 154(b) by 0 days.

(21) Appl. No.: 15/016,921

(22) Filed: Feb. 5, 2016

(65) Prior Publication Data
US 2016/0228354 A1    Aug. 11, 2016

Related U.S. Application Data

(60) Provisional application No. 62/112,555, filed on Feb. 5, 2015.

(51) Int. Cl.
| | | |
|---|---|---|
| *A61K 31/407* | (2006.01) | |
| *A61K 31/167* | (2006.01) | |
| *A61K 9/00* | (2006.01) | |
| *A61K 9/06* | (2006.01) | |
| *A61K 31/4439* | (2006.01) | |
| *A61K 31/5517* | (2006.01) | |
| *A61K 47/10* | (2017.01) | |
| *A61K 47/14* | (2017.01) | |

(52) U.S. Cl.
CPC ........... *A61K 9/0014* (2013.01); *A61K 9/06* (2013.01); *A61K 31/167* (2013.01); *A61K 31/407* (2013.01); *A61K 31/4439* (2013.01); *A61K 31/5517* (2013.01); *A61K 47/10* (2013.01); *A61K 47/14* (2013.01)

(58) Field of Classification Search
CPC ...... A61K 9/00; A61K 9/0014; A61K 31/407; A61K 31/167
See application file for complete search history.

(56) References Cited

U.S. PATENT DOCUMENTS

| | | |
|---|---|---|
| 3,189,617 A | 6/1965 | Archer et al. |
| 3,723,459 A | 3/1973 | Paragamian |
| 3,845,770 A | 11/1974 | Theeuwes et al. |
| 4,045,576 A | 8/1977 | Welstead, Jr. et al. |
| 4,326,525 A | 4/1982 | Swanson et al. |
| 4,438,130 A | 3/1984 | Kaplan |
| 4,440,785 A | 4/1984 | Walsh |
| 4,670,566 A | 6/1987 | Walsh |
| 4,886,788 A | 12/1989 | Skuballa et al. |
| 4,935,446 A | 6/1990 | Imaki et al. |
| 5,023,265 A | 6/1991 | Scherlock et al. |
| 5,116,854 A | 5/1992 | Marfat |
| 5,182,289 A | 1/1993 | Ting et al. |
| 5,278,162 A | 1/1994 | Wilkerson |
| 5,296,478 A | 3/1994 | Teleha |
| 5,304,121 A | 4/1994 | Sahatjian |
| 5,453,516 A | 9/1995 | Fischer et al. |
| 5,663,431 A | 9/1997 | Di Malta et al. |
| 5,686,624 A | 11/1997 | Di Malta et al. |
| 5,696,145 A | 12/1997 | Foulon et al. |
| 5,723,625 A | 3/1998 | Keplinger et al. |
| 5,726,322 A | 3/1998 | Di Malta et al. |
| 5,728,723 A | 3/1998 | Di Malta et al. |

(Continued)

FOREIGN PATENT DOCUMENTS

| | | |
|---|---|---|
| CA | 2095718 A1 | 5/1992 |
| CA | 2107348 A1 | 7/1993 |

(Continued)

OTHER PUBLICATIONS

Adams et al., "Bicyclic N-Hydroxyurea Inhibitors of 5-Lipoxygenase: Pharmacodynamic, Pharmacokinetic, and in Vitro Metabolic Studies Characterizing N-Hydroxy-N-(2,3-dihydro-6-(phenylmethoxy)-3-benzofuranyl)urea," *J. Med. Chem.* 39(26): 5035-5046, 1996.

Akai, "Development of Novel Asymmetric Reactions Oriented to Next-Generation Enzymatic Organic Syntheses," *Yakugaku Zasshi* 123(11): 919-931, 2003.

Al-Thebeiti and El-Zohry, "A Facile Route for the Synthesis of Some New Spiro[indoline-3,3'-indan]-2,1'-dione Derivatives," *Heterocycles* 41(11): 2475-2480, 1995.

Alabaster et al., "The Synthesis of 5-Substituted 2,3-Dihydrobenzofurans," *Synthesis* 12: 950-952, Dec. 1988.

(Continued)

*Primary Examiner* — San-Ming Hui
(74) *Attorney, Agent, or Firm* — Seed IP Law Group LLP

(57) ABSTRACT

Methods of treating postherpetic neuralgia in a mammal with a pharmaceutical composition comprising a spiro-oxindole compound of the formula:

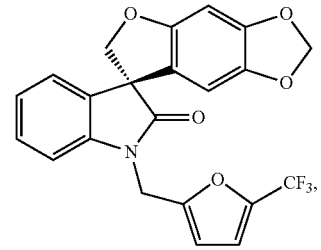

are disclosed. The methods provide excellent penetration of the spiro-oxindole compound into the affected skin area to effectively reduce the severity of the postherpetic neuralgia and/or to alleviate the postherpetic neuralgia with minimal or negligible systemic exposure of the spiro-oxindole compound.

22 Claims, No Drawings

(56) References Cited

U.S. PATENT DOCUMENTS

| | | | |
|---|---|---|---|
| 5,763,471 A | 6/1998 | Fourtillan et al. |
| 5,767,128 A | 6/1998 | Guillaumet et al. |
| 5,776,936 A | 7/1998 | Lee et al. |
| 5,849,780 A | 12/1998 | Di Malta et al. |
| 5,886,026 A | 3/1999 | Hunter et al. |
| 5,994,350 A | 11/1999 | Foulon et al. |
| 6,046,341 A | 4/2000 | Foulon et al. |
| 6,090,818 A | 7/2000 | Foulon et al. |
| 6,099,562 A | 8/2000 | Ding et al. |
| 6,110,969 A | 8/2000 | Tani et al. |
| 6,225,347 B1 | 5/2001 | Buchmann et al. |
| 6,235,780 B1 | 5/2001 | Ohuchida et al. |
| 6,262,293 B1 | 7/2001 | Tani et al. |
| 6,288,119 B1 | 9/2001 | Ohuchida et al. |
| 6,355,627 B1 | 3/2002 | Ishida et al. |
| 6,414,153 B1 | 7/2002 | Kelly et al. |
| 6,670,357 B2 | 12/2003 | Leftheris et al. |
| 6,964,973 B2 | 11/2005 | Zhi et al. |
| 7,368,470 B2 | 5/2008 | Sundermann et al. |
| 7,700,641 B2 | 4/2010 | Chafeev et al. |
| 7,799,798 B2 | 9/2010 | Chafeev et al. |
| 7,888,345 B2 | 2/2011 | Hoyt et al. |
| 7,935,721 B2 | 5/2011 | Sun et al. |
| 8,101,647 B2 | 1/2012 | Chafeev et al. |
| 8,106,087 B2 | 1/2012 | Chafeev et al. |
| 8,263,606 B2 | 9/2012 | Chafeev et al. |
| 8,415,370 B2 | 4/2013 | Chafeev et al. |
| 8,445,696 B2 | 5/2013 | Cadieux et al. |
| 8,450,358 B2 | 5/2013 | Chafeev et al. |
| 8,466,188 B2 | 6/2013 | Chafeev et al. |
| 8,742,109 B2 | 6/2014 | Cadieux et al. |
| 8,883,840 B2 | 11/2014 | Chafeev et al. |
| 2002/0039790 A1 | 4/2002 | Keplinger et al. |
| 2004/0038970 A1 | 2/2004 | Thurieau et al. |
| 2004/0167224 A1 | 8/2004 | Ozaki et al. |
| 2005/0004137 A1 | 1/2005 | Romano |
| 2005/0004138 A1 | 1/2005 | Romano |
| 2005/0014764 A1 | 1/2005 | Romano et al. |
| 2005/0020617 A1 | 1/2005 | Bastian et al. |
| 2005/0038036 A1 | 2/2005 | Romano et al. |
| 2005/0075351 A1 | 4/2005 | Berg et al. |
| 2005/0153998 A1 | 7/2005 | Ito et al. |
| 2005/0159473 A1 | 7/2005 | Sall et al. |
| 2005/0171186 A1 | 8/2005 | Fensome et al. |
| 2005/0256110 A1 | 11/2005 | Collins et al. |
| 2005/0256144 A1 | 11/2005 | Kath et al. |
| 2006/0247441 A1 | 11/2006 | Wilk |
| 2007/0049609 A1 | 3/2007 | Broka et al. |
| 2007/0072831 A1 | 3/2007 | Cai et al. |
| 2007/0105820 A1 | 5/2007 | Chafeev et al. |
| 2007/0299102 A1 | 12/2007 | Felding et al. |
| 2008/0103151 A9 | 5/2008 | Chafeev et al. |
| 2011/0034500 A1 | 2/2011 | Chafeev et al. |
| 2011/0086899 A1 | 4/2011 | Winters et al. |
| 2011/0237567 A9 | 9/2011 | Chafeev et al. |
| 2011/0269788 A1 | 11/2011 | Cadieux et al. |
| 2011/0294842 A9 | 12/2011 | Cadieux et al. |
| 2012/0122909 A9 | 5/2012 | Chafeev et al. |
| 2013/0072537 A1 | 3/2013 | Chafeev et al. |
| 2013/0143941 A1 | 6/2013 | Winters et al. |
| 2013/0252962 A1 | 9/2013 | Chafeev et al. |
| 2013/0274483 A1 | 10/2013 | Sun et al. |
| 2014/0336390 A1 | 11/2014 | Cadieux et al. |
| 2015/0025121 A1 | 1/2015 | Chafeev et al. |
| 2015/0291623 A1 | 10/2015 | Chafeev et al. |

FOREIGN PATENT DOCUMENTS

| | | |
|---|---|---|
| CA | 2129215 A1 | 1/1995 |
| CA | 2274898 A1 | 6/1998 |
| CA | 2450550 A1 | 1/2003 |
| CA | 2466915 A1 | 8/2003 |
| CA | 2487494 A1 | 12/2003 |
| CA | 2235686 C | 6/2007 |
| DE | 1956237 A | 5/1971 |
| DE | 2113343 A1 | 9/1972 |
| EP | 0147805 A2 | 7/1985 |
| EP | 0164860 A1 | 12/1985 |
| EP | 0175551 A1 | 3/1986 |
| EP | 0608058 A1 | 7/1994 |
| EP | 1422217 A2 | 5/2004 |
| EP | 1557166 A1 | 7/2005 |
| EP | 2073806 B1 | 2/2012 |
| FR | 2722195 A1 | 1/1996 |
| JP | 7-508976 A | 10/1995 |
| JP | 1095766 A | 4/1998 |
| JP | 2003505388 | 2/2003 |
| JP | 2006-519224 A | 8/2006 |
| WO | WO 86/03749 A1 | 7/1986 |
| WO | WO 91/01306 A1 | 2/1991 |
| WO | WO 91/04974 A1 | 4/1991 |
| WO | WO 91/06545 A1 | 5/1991 |
| WO | WO 92/09577 A1 | 6/1992 |
| WO | WO 93/12786 A1 | 7/1993 |
| WO | WO 93/15051 A1 | 8/1993 |
| WO | WO 93/23083 A1 | 11/1993 |
| WO | WO 94/03427 A1 | 2/1994 |
| WO | WO 95/06688 A1 | 3/1995 |
| WO | WO 95/14667 A1 | 6/1995 |
| WO | WO 96/19477 A1 | 6/1996 |
| WO | WO 97/15556 A1 | 5/1997 |
| WO | WO 97/36895 A1 | 10/1997 |
| WO | WO 98/25901 A1 | 6/1998 |
| WO | WO 98/50016 A2 | 11/1998 |
| WO | WO 00/06556 A1 | 2/2000 |
| WO | WO 00/42044 A1 | 7/2000 |
| WO | WO 00/71129 A1 | 11/2000 |
| WO | WO 01/05790 A1 | 1/2001 |
| WO | WO 01/38564 A2 | 5/2001 |
| WO | WO 01/38564 A3 | 5/2001 |
| WO | WO 01/74775 A1 | 10/2001 |
| WO | WO 02/30868 A1 | 4/2002 |
| WO | WO 02/38544 A2 | 5/2002 |
| WO | WO 03/000677 A1 | 1/2003 |
| WO | WO 03/037274 A2 | 5/2003 |
| WO | WO 03/037890 A2 | 5/2003 |
| WO | WO 03/064425 A1 | 8/2003 |
| WO | WO 03/078394 A1 | 9/2003 |
| WO | WO 03/106457 A1 | 12/2003 |
| WO | WO 2004/000225 A2 | 12/2003 |
| WO | WO 2004/000227 A2 | 12/2003 |
| WO | WO 2004/048320 A1 | 6/2004 |
| WO | WO 2004/074285 A1 | 9/2004 |
| WO | WO 2005/011657 A2 | 2/2005 |
| WO | WO 2005/016913 A1 | 2/2005 |
| WO | WO 2005/019208 A1 | 3/2005 |
| WO | WO 2005/035498 A1 | 4/2005 |
| WO | WO 2005/056554 A1 | 6/2005 |
| WO | WO 2005/070919 A1 | 8/2005 |
| WO | WO 2005/092304 A2 | 10/2005 |
| WO | WO 2005/092895 A2 | 10/2005 |
| WO | WO 2005/097107 A2 | 10/2005 |
| WO | WO 2005/097122 A2 | 10/2005 |
| WO | WO 2005/097136 A1 | 10/2005 |
| WO | WO 2005/099689 A1 | 10/2005 |
| WO | WO 2005/104711 A2 | 11/2005 |
| WO | WO 2005/105753 A2 | 11/2005 |
| WO | WO 2005/110992 A1 | 11/2005 |
| WO | WO 2005/111024 A1 | 11/2005 |
| WO | WO 2006/012173 A1 | 2/2006 |
| WO | WO 2006/017075 A1 | 2/2006 |
| WO | WO 2006/023107 A1 | 3/2006 |
| WO | WO 2006/023109 A1 | 3/2006 |
| WO | WO 2006/049290 A1 | 5/2006 |
| WO | WO 2006/055752 A2 | 5/2006 |
| WO | WO 2006/087019 A1 | 8/2006 |
| WO | WO 2006/091646 A2 | 8/2006 |
| WO | WO 2006/110654 A1 | 10/2006 |
| WO | WO 2006/110917 A2 | 10/2006 |
| WO | WO 2006/113864 A2 | 10/2006 |
| WO | WO 2006/113875 A2 | 10/2006 |
| WO | WO 2007/025925 A1 | 3/2007 |
| WO | WO 2008/046046 A1 | 4/2008 |
| WO | WO 2008/046049 A1 | 4/2008 |

(56) References Cited

FOREIGN PATENT DOCUMENTS

| | | |
|---|---|---|
| WO | WO 2008/046065 A1 | 4/2008 |
| WO | WO 2008/046082 A2 | 4/2008 |
| WO | WO 2008/046083 A2 | 4/2008 |
| WO | WO 2008/046084 A2 | 4/2008 |
| WO | WO 2008/046087 A2 | 4/2008 |
| WO | WO 2008/060789 A2 | 5/2008 |
| WO | WO 2008/110741 A2 | 9/2008 |
| WO | WO 2008/117050 A1 | 10/2008 |
| WO | WO 2008/153801 A1 | 12/2008 |
| WO | WO 2010/045197 A1 | 4/2010 |
| WO | WO 2010/045251 A2 | 4/2010 |
| WO | WO 2010/053998 A1 | 5/2010 |
| WO | WO 2010/078307 A1 | 7/2010 |
| WO | WO 2010/132352 A2 | 11/2010 |
| WO | WO 2011/002708 A1 | 1/2011 |
| WO | WO 2011/047173 A9 | 4/2011 |
| WO | WO 2011/047174 A1 | 4/2011 |
| WO | WO 2011/106729 A2 | 9/2011 |
| WO | WO 2011/109526 A1 | 9/2011 |
| WO | WO 2013/154712 A1 | 10/2013 |
| WO | WO 2015/120151 A1 | 8/2015 |
| WO | WO 2016/127068 A1 | 8/2016 |

OTHER PUBLICATIONS

Alcaide et al., "Efficient Entry to Diversely Functionalized Spirocyclic Oxindoles from Isatins through Carbonyl-Addition/Cyclization Reaction Sequences," *J. Org. Chem.* 71(6): 2346-2351, 2006.

Alper et al., "Eine neuartige Methode zur Synthese von Spiro[pyrrolidin-3,3'-oxindolen]: katalysierte Ringerweiterung von Cyclopropanen mit Aldiminen," *Angew. Chem.* 111(21): 3379-3381, 1999.

Alper et al., "Facile, Novel Methodology for the Synthesis of Spiro[pyrrolidin-3,3'-oxindoles]: Catalyzed Ring Expansion Reactions of Cyclopropanes by Aldimines," *Angew. Chem. Int. Ed.* 38(21): 3186-3189, 1999.

Altman et al., "Development of Criteria for the Classification and Reporting of Osteoarthritis," *Arthritis and Rheumatism* 29(8): 1039-1049, Aug. 1986.

Anderson et al., "Measures of Rheumatoid Arthritis Disease Activity," *Arthritis Care & Research* 63(S11): S14-S36, Nov. 2011.

Anger et al., "Medicinal Chemistry of Neuronal Voltage-Gated Sodium Channel Blockers," *Journal of Medicinal Chemistry* 44(2): 115-137, Jan. 18, 2001.

Arcangeli et al., "Targeting Ion Channels in Cancer: A Novel Frontier in Antineoplastic Therapy," *Current Medicinal Chemistry* 16: 66-93, 2009.

Autrey and Tahk, "The Synthesis and Stereochemistry of Some Isatylideneacetic Acid Derivatives," *Tetrahedron* 23: 901-917, 1967.

Bacher et al., "Oxindole alkaloids from *Uncaria tomentosa* induce apoptosis in proliferating, G0/G1-arrested and bcl-2-expressing acute lymphoblastic leukaemia cells," *British Journal of Haematology* 132: 615-622, 2005.

Banfi et al., "High Diastereoface Selection in an Ester Enolate Addition to α-Alkoxy Aldehydes: Stereoselective Synthesis of α-Methylene-β-hydroxy-γ-alkoxy Esters," *J. Org. Chem.* 49: 3784-3790, 1984.

Basavaiah et al., "TiCl$_4$ catalyzed tandem construction of C—C and C—O bonds: a simple and one-pot atom-economical stereoselective synthesis of spiro-oxindoles," *Chem. Commun.* 2621-2623, 2005.

Bean et al., "Lidocaine Block of Cardiac Sodium Channels," *J. Gen. Physiol.* 81: 613-642, May 1983.

Bellamy et al., "Validation Study of WOMAC: A Health Status Instrument for Measuring Clinically Important Patient Relevant Outcomes to Antirheumatic Drug Therapy in Patients with Osteoarthritis of the Hip or Knee," *J. Rheumatol.* 15: 1833-1840, 1988.

Bennett and Xie, "A peripheral mononeuropathy in rat that produces disorders of pain sensation like those seen in man," *Pain* 33: 87-107, 1988.

Beyersbergen Van Henegouwen et al., "First Total Synthesis of *ent*-Gelsedine via a Novel Iodide-Promoted Allene *N*-Acyliminium Ion Cyclization," *J. Org. Chem.* 65(24): 8317-8325, 2000.

Beyersbergen Van Henegouwen et al., "Total Synthesis of (+)-Gelsedine," *Angew. Chem. Int. Ed.* 38(15): 2214-2217, 1999.

Billert and Beckert, "Beiträge zur Chemie der Pyrido[1,2-α]pyrazine—Reaktivität gegenüber Heterocumulenen der Kohlensäurereihe und Ketenen," *J. Prakt. Chem.* 341(4): 332-341, 1999.

Binder et al., "Disease mechanisms in neuropathic itch," *Nature Clinical Practice/ Neurology* 4(6): 329-337, Jun. 2008.

Blair et al., "Roles of Tetrodotoxin (TTX)-Sensitive Na$^+$ Current, TTX-Resistant Na$^+$ Current, and Ca$^{2+}$ Current in the Action Potentials of Nociceptive Sensory Neurons," *The Journal of Neuroscience* 22(23): 10277-10290, Dec. 1, 2002.

Bond et al., "Cyclopiamines A and B, Novel Oxindole Metabolites of *Penicillium cyclopium* Westling," *Journal of the Chemical Society, Perkin Transaction 1: Organic and Bio-Organic Chemistry* 7: 1751-1761, 1979.

Brackenbury and Djamgoz, "Activity-dependent regulation of voltage-gated Na$^+$ channel expression in Mat-LyLu rat prostate cancer cell line," *J. Physiol.* 573.2: 343-356, 2006.

Bramson et al., "Oxindole-Based Inhibitors of Cyclin-Dependent Kinase 2 (CDK2): Design, Synthesis, Enzymatic Activities, and X-ray Crystallographic Analysis," *J. Med. Chem.* 44: 4339-4358, 2001.

Braude and Lindwall, "Condensations of Isatin with Acetone by the Knoevenagel Method," *Journal of the American Chemical Society* 55: 325-327, Jan. 1933.

Byrn et al., "Chapter 11, Hydrates and Solvates," in *Solid-State Chemistry of Drugs*, Second Edition, 1999, pp. 233-247.

Caldwell et al., "Sodium channel Na$_v$1.6 is localized at nodes of Ranvier, dendrites, and synapses," *PNAS* 97(10): 5616-5620, May 9, 2000.

Cañas-Rodriguez and Leeming, "N-Phenyl-2-indolinones and N-Phenylindolines. A New Class of Antidepressant Agents," *Journal of Medicinal Chemistry* 15(7): 762-770, 1972.

Capilla et al., "Synthesis of isoquinolines and tetrahydroisoquinolines as potential antitumour agents," *Tetrahedron* 57: 8297-8303, 2001.

Carlson et al., "Potential hypolipidemic agents: VI. Syntheses of some new halo-substituted pyridine compounds. Effects on noradrenaline-stimulated free fatty acid mobilization," *Acta Pharm. Suecica* 9: 411-418, 1972.

Cassebaum and Liedel, "Beziehungen zwischen Konstitution und α-Aminosäure-dehydrogenasewirkung von Isatinen," *Journal für praktische Chemie* 4(12):91-95, 1960.

Catterall, "Molecular mechanisms of gating and drug block of sodium channels," *2002 Sodium channels and neuronal hyperexcitability*, Wiley, Chichester (Novartis Foundation Symposium 241), p. 206-225.

Cestèle and Catterall, "Molecular mechanisms of neurotoxin action on voltage-gated sodium channels," *Biochimie* 82: 883-892, 2000.

Chande et al., "Facile synthesis of active antitubercular, cytotoxic and antibacterial agents: a Michael addition approach," *European Journal of Medicinal Chemistry* 40: 1143-1148, 2005.

Chaplan et al., "Quantitative assessment of tactile allodynia in the rat paw," *Journal of Neuroscience Methods* 53: 55-63, 1994.

Chen et al., "Antiviral treatment for preventing postherpetic neuralgia (Review)," *Cochrane Database of Systematic Reviews* 2: CD006866, 2014, 45 pages.

Chioni et al., "A novel adhesion molecule in human breast cancer cells: Voltage-gated Na$^+$ channel β1 subunit," *The International Journal of Biochemistry & Cell Biology* 41: 1216-1227, 2009.

Chung et al., "Sodium channels and neuropathic pain," *Novartis Found Symp.* 261: 19-27, 2004.

Clare et al., "Voltage-gated sodium channels as therapeutic targets," *Drug Discovery Today* 5(11): 506-520, Nov. 2000.

(56) References Cited

OTHER PUBLICATIONS

Claudi et al., "Synthesis and Dopamine Receptor Affinities of 2-(4-Fluoro-3-hydroxyphenyl)ethylamine and N-Substituted Derivatives," *J. Med. Chem.* 33: 2408-2412, 1990.

Coppola, "N-Acylation of Isatins. A Direct Route to N-Arylisatoic Anhydrides," *J. Heterocyclic Chem.* 24: 1249-1251, Sep./Oct. 1987.

Corey and Noe, "Preparation of O-Allyl-N-(9-Anthracenylmethyl)Cinchonidinium Bromide as a Phase Transfer Catalyst for the Enantioselective Alkylation of Glycine Benzophenone Imine tert-Butyl Ester: (4S)-2-(Benzhydrylidenamino)Pentanedioic Acid, 1-tert-Butyl Ester-5-Methyl Ester [[Cinchonanium, 1-(9-anthracenylmethyl)-9-(2-propenyloxy)-, bromide, (8α,9R)-and L-Glutamic acid, N-(diphenylmethylene)-, 1-(1,1-dimethylethyl) 5-methyl ester]]," *Organic Syntheses* 80(11): 38-45, 2003; Col. vol. 11: 404-409.

Cossy et al., "A Convenient Route to Spiropyrrolidinyl-Oxindole Alkaloids via C-3 Substituted Ene-Pyrrolidine Carbamate Radical Cyclization," *Tetrahedron Letters* 39: 2331-2332, 1998.

Cox et al., "An SCN9A channelopathy causes congenital inability to experience pain," *Nature* 444: 894-898, Dec. 14, 2006.

Craner et al., "Molecular changes in neurons in multiple sclerosis: Altered axonal expression of $Na_v1.2$ and $Na_v1.6$ sodium channels and $Na^+ / Ca^{2+}$ exchanger," *PNAS* 101(21): 8168-8173, May 25, 2004.

Cravotto et al., "Azomethine Ylide Cycloaddition/Reductive Heterocyclization Approach to Oxindole Alkaloids: Asymmetric Synthesis of (—)-Horsfiline," *J. Org. Chem.* 66(25): 8447-8453, 2001.

Creveling and Daly, "Batrachotoxinin A [$^3$H]Benzoate Binding to Sodium Channels," *Methods in Neurosciences* 8: 25-37, 1992.

Cube et al., "3-(2-Ethoxy-4-{4-[3-hydroxy-2-methyl-4-(3-methylbutanoyl)-phenoxy]butoxy}phenyl)propanoic acid: a brain penetrant allosteric potentiator at the metabotropic glutamate receptor 2 (mGluR2)," *Bioorganic & Medicinal Chemistry Letters* 15: 2389-2393, 2005.

Cummins et al., "The roles of sodium channels in nociception: Implications for mechanisms of pain," *Pain* 131: 243-257, 2007.

Dallacker and Sanders, "Darstellung and Reaktionen von 5-(3'-Hydroxy-oxindol-3'-yl)-1,3-benzdioxole," *Chemiker-Zeitung* 110(11): 405-411, 1986.

Davies et al., "Review of Lidocaine Patch 5% Studies in the Treatment of Postherpetic Neuralgia," *Drugs* 64(9): 937-947, 2004.

Dehmlow et al., "Monodeazacinchona Alkaloid Derivatives: Synthesis and Preliminary Applications as Phase-Transfer Catalysts," *Eur. J. Org. Chem.* 13: 2087-2093, 2002.

Devers and Galer, "Topical Lidocaine Patch Relieves a Variety of Neuropathic Pain Conditions: An Open-Label Study," *Clinical Journal* 16(3): 205-208, Sep. 2000, obtained from URL=http://ovidsp.tx.ovid.com/spb/ovidweb.cgi, download date Apr. 18, 2008, 5 pages.

Dib-Hajj et al., "Genetics and Molecular Pathophysiology of $Na_v1.7$-Related Pain Syndromes," *Advances in Genetics* 63: 85-110, 2008.

Dib-Hajj et al., "NaN, a novel voltage-gated Na channel, is expressed preferentially in peripheral sensory neurons and down-regulated after axotomy," *Proc. Natl. Acad. Sci. USA* 95: 8963-8968, Jul. 1998.

Dib-Hajj et al., "Gain-of-function mutation in $Na_v1.7$ in familial erythromelalgia induces bursting of sensory neurons," *Brain* 128: 1847-1854, 2005.

Dierks et al., "A Method for the Simultaneous Evaluation of the Activities of Seven Major Human Drug-Metabolizing Cytochrome P450S Using an In Vitro Cocktail of Probe Substrates and Fast Gradient Liquid Chromatography Tandem Mass Spectrometry," *Drug Metabolism and Disposition* 29(1): 23-29, 2001.

Ding et al., "Structure-Based Design of Spiro-oxindoles as Potent, Specific Small-Molecule Inhibitors of the MDM2-p53 Interaction," *J. Med. Chem* 49(12): 3432-3435, 2006.

Diss et al., "A potential novel marker for human prostate cancer: voltage-gated sodium channel expression in vivo," *Prostate Cancer and Prostatic Diseases* 8: 266-273, 2005.

Diss et al., "Expression Profiles of Voltage-Gated $Na^+$ Channel α-Subunit Genes in Rat and Human Prostate Cancer Cell Lines," *The Prostate* 48:165-178, 2001.

Diss et al., "Identification and characterization of the promoter region of the Nav1.7 voltage-gated sodium channel gene (SCN9A)," *Mol. Cell. Neurosci.* 37: 537-547, 2008.

Do and Bean, "Subthreshold Sodium Currents and Pacemaking of Subthalamic Neurons: Modulation by Slow Inactivation," *Neuron* 39: 109-120, Jul. 3, 2003.

Domingo et al., "Studies on the Biosynthesis of Paraherquamide A and VM99955. A Theoretical Study of Intramolecular Diels—Alder Cycloaddition," *J. Org. Chem.* 68(7): 2895-2902, 2003.

Doyle et al., "Rhodium (II) Acetate and Nafion-H Catalyzed Decomposition of N-Aryldiazoamides. An Efficient Synthesis of 2(3H)-Indolinones," *J. Org. Chem* 53(5): 1017-1022, 1988.

Drenth et al., "SCN9A Mutations Define Primary Erythermalgia as a Neuropathic Disorder of Voltage Gated Sodium Channels," *J. Invest. Dermatol.* 124: 1333-1338, 2005.

Dubinsky et al., "Practice Parameter: Treatment of postherpetic neuralgia—An evidence-based report of the Quality Standards Subcommittee of the American Academy of Neurology," *Neurology* 63: 959-965, 2004.

Dubuisson and Dennis, "The Formalin Test: A Quantitative Study of the Analgesic Effects of Morphine, Meperidine, and Brain Stem Stimulation in Rats and Cats," *Pain* 4: 161-174, 1977.

Dutton et al., "A Total Synthesis of Gelsemine: Oxindole Spiroannelation," *J. Chem. Soc., Chem. Commun.* 765-766, 1994.

Dutton et al., "Synthesis of Hindered Spiro-Oxindoles by Photolysis of 1-(1-Alkenyl)benzotriazoles," *Tetrahedron* 55: 11927-11942, 1999.

Dworkin et al., "Pregabalin for the treatment of postherpetic neuralgia—A randomized, placebo-controlled trial," *Neurology* 60: 1274-1283, 2003.

El-Ahl, "Three-Component 1,3-Dipolar Cycloaddition Reactions in Synthesis of Spiro[pyrrolidine-2,3'-oxindoline] Derivatives," *Heteroatom Chemistry* 13(4): 324-329, 2002.

El-Gendy and Ahmedy, "Synthesis and Antimicrobial Activity of some New 2-Indolinone Derived Oximes and Spiro-Isoxazolines," *Arch. Pharm. Res.* 23(4): 310-314, 2000.

Ettinger and Argoff, "Use of Antiepileptic Drugs for Nonepileptic Conditions: Psychiatric Disorders and Chronic Pain," *Neurotherapeutics: The Journal of the American Society for Experimental NeuroTherapeutics* 4:75-83, Jan. 2007.

Faber et al., "Gain of Function $Na_v1.7$ Mutations in Idiopathic Small Fiber Neuropathy," *Ann. Neurol.* 71: 26-39, 2012.

Feldman and Karatjas, "Extending Pummerer Reaction Chemistry. Asymmetric Synthesis of Spirocyclic Oxindoles via Chiral Indole-2-sulfoxides," *Org. Lett.* 8(18): 4137-4140, 2006.

Feldman et al., "Extending Pummerer Reaction Chemistry. Development of a Strategy for the Regio- and Stereoselective Oxidative Cyclization of 3-(ω-Nucleophile)-Tethered Indoles," *J. Org. Chem.* 70(16): 6429-6440, 2005.

Feldman and Vidulova, "Extending Pummerer Reaction Chemistry. Application to the Oxidative Cyclization of Indole Derivatives," *Organic Letters* 6(11): 1869-1871, 2004.

Felson, "Osteoarthritis of the Knee," *N. Engl. J. Med.* 354: 841-848, 2006.

Fertleman et al., "SCN9A Mutations in Paroxysmal Extreme Pain Disorder: Allelic Variants Underlie Distinct Channel Defects and Phenotypes," *Neuron* 52: 767-774, Dec. 7, 2006.

Fishman et al., "Intravenous Lidocaine for Treatment-resistant Pruritus," *American Journal of Medicine* 102: 584-585, Jun. 1997.

Flanagan et al., "Radical cyclisation reactions with indoles," *Tetrahedron Letters* 44: 1795-1798, 2003.

Fokas et al., "Solution Phase Synthesis of a Spiro[pyrrolidine-2,3'-oxindole] Library via a Three Component 1,3-Dipolar Cycloaddition Reaction," *Tetrahedron Letters* 39: 2235-2238, 1998.

Foster et al., "457. Furano-compounds. Part VII. A Synthesis of 2 : 3-Dihydropsoralene," *J. Chem. Soc.* 2254-2260, 1948.

(56) References Cited

OTHER PUBLICATIONS

Fraser et al., "Voltage-Gated Sodium Channel Expression and Potentiation of Human Breast Cancer Metastasis," *Clin. Cancer Res.* 11(15): 5381-5389, Aug. 1, 2005.

Fuchs and Funk, "Indol-2-one Intermediates: Mechanistic Evidence and Synthetic Utility. Total Syntheses of (±)-Flustramines A and C," *Org. Lett.* 7(4): 677-680, 2005.

Fuchs and See, "Basolateral amygdala inactivation abolishes conditioned stimulus- and heroin-induced reinstatement of extinguished heroin-seeking behavior in rats," *Psychopharmacology* 160: 425-433, 2002.

Fuji et al., "Direct Asymmetric Synthesis of Quaternary Carbon Centers via Addition-Elimination Process: Nitroolefination of α-Substituted δ-Lactones," *J. Am. Chem. Soc.* 111: 7921-7925, 1989.

Fujita et al., "The Beckmann Rearrangement by Means of Phosphoryl Chloride/$N,N$-Dimethylacetamide; A Novel and Convenient Method for Preparing Benzoxazoles," *Synthesis* 68-69, Jan. 1982.

Gálvez and García, "Synthesis of Isomeric β-Haloethylthienopyrroles," *J. Heterocyclic Chem.* 21: 393-395, Mar.-Apr. 1984.

Ganguly et al., "Solution- and solid-phase synthesis of enantiomerically pure spiro oxindoles," *Tetrahedron Letters* 43: 8981-8983, 2002.

Ganguly et al., "Synthesis of heterocyclic compounds using radical reactions and evidence for the formation of spiro radical intermediates," *Tetrahedron Letters* 45: 883-886, 2004. See also Ganguly et al., "Corrigendum to 'Synthesis of heterocyclic compounds using radical reactions and evidence for the formation of spiro radical intermediates,'" [*Tetrahedron Letters* 45: 883-886, 2004], *Tetrahedron Letters* 45: 3835, 2004.

Garden et al., "A versatile synthetic methodology for the synthesis of tryptophols," *Tetrahedron* 58: 8399-8412, 2002.

Garden et al., "Investigation of the selective reduction of isatin derivatives. Synthesis of α-hydroxyacetophenone derivatives and ethyl *spiro*-3,3-(ethylenedioxy)-2-hydroxyindoline carboxylates," *Tetrahedron Letters* 44: 7617-7621, 2003.

Goldberg et al., "Loss-of-function mutations in the $Na_v1.7$ gene underlie congenital indifference to pain in multiple human populations," *Clin. Genet.* 71: 311-319, 2007.

Goldberg, "The Significance of Molecular Type, Shape and Complementarity in Clathrate Inclusion," *Topics in Current Chemistry* 149: 1-44, 1988.

González-López De Turiso and Curran, "Radical Cyclization Approach to Spirocyclohexadienones," *Organic Letters* 7(1): 151-154, 2005.

Grigg et al., "Palladium Catalysed Ter- and Tetra-molecular Queuing Processes. One-pot Routes to 3-Spiro-2-Oxindoles and 3-Spiro-2(3H)-Benzofuranones," *Tetrahedron Letters* 37(5): 695-698, 1996.

Grigg et al., "Spiro-oxindoles via bimetallic [Pd(0)/Ag(I)] catalytic intramolecular Heck-1,3-dipolar cycloaddition cascade reactions," *Tetrahedron Letters* 43: 2605-2608, 2002.

Grigoryan et al., "Synthesis and antispasmodic activity of spiro[β-carbolineindolones] and spiro[indoleindolo[2,3-c]azepinones]," *Hayastani Kimiakan Handes* 58(3): 100-104, 2005, CAPLUS Database Accession No. 2005:876436, 4 pages, Abstract only.

Guillaumet et al., "Synthese d'un analogue dioxinique du psoralene," *Tetrahedron Letters* 29(22): 2665-2666, 1988.

Hains et al., "Upregulation of Sodium Channel $Na_v1.3$ and Functional Involvement in Neuronal Hyperexcitability Associated with Central Neuropathic Pain after Spinal Cord Injury," *Journal of Neuroscience* 23(26): 8881-8892, Oct. 1, 2003.

Hamann et al., "Motor disturbances in mice with deficiency of the sodium channel gene *Scn8a* show features of human dystonia," *Experimental Neurology* 184: 830-838, 2003.

Haufe et al., "The promiscuous nature of the cardiac sodium current," *Journal of Molecular and Cellular Cardiology* 42: 469-477, 2007.

Hiemstra et al., "Models of Folate Coenzymes—VIII: An Approach to Yohimbane Alkaloids Via Carbon-Fragment Transfer From $N^5$, $N^{10}$-Methylenetetrahydrofolate Models," *Tetrahedron* 39(23): 1981-1986, 1983.

Hille, "Local Anesthetics: Hydrophilic and Hydrophobic Pathways for the Drug-Receptor Reaction," *The Journal of General Physiology* 69: 497-515, 1977.

Hille, "The pH-Dependent Rate of Action of Local Anesthetics on the Node of Ranvier," *The Journal of General Physiology* 69: 475-496, 1977.

Hoffman, *Organic Chemistry: An Intermediate Text—Second Edition*, John Wiley & Sons, Inc., Hoboken, New Jersey, 2004, 124, 138-144.

Hoyt et al., "Benzazepionone $Na_v1.7$ blockers: Potential treatments for neuropathic pain," *Bioorganic & Medicinal Chemistry Letters* 17: 6172-6177, 2007.

Hurst et al., "Assessing the Clinical Significance of Change Scores Recorded on Subjective Outcome Measures," *Journal of Manipulative and Physiological Therapeutics* 27(1): 26-35, Jan. 2004.

Ikoma et al., "The neurobiology of itch," *Nature Reviews Neuroscience* 7: 535-547, Jul. 2006.

Ikoma et al., "Neuronal Sensitization for Histamine-Induced Itch in Lesional Skin of Patients With Atopic Dermatitis," *Arch Dermatol.* 139: 1455-1458, Nov. 2003.

Inan et al , "Inhibitory effect of lidocaine on pain and itch using formalin-induced nociception and 5′-guanidinonaltrindole-induced scratching models in mice: Behavioral and neuroanatomical evidence," *European Journal of Pharmacology* 616: 141-146, 2009.

Iranpoor et al., "A novel method for the highly efficient synthesis of 1,2-benzisoxazoles under neutral conditions using the $Ph_3P/DDQ$ system," *Tetrahedron Letters* 47: 8247-8250, 2006.

Ishiyama et al., "Synthesis of Arylboronates via the Palladium(0)-Catalyzed Cross-Coupling Reaction of Tetra(alkoxo)diborons with Aryl Triflates," *Tetrahedron Letters* 38(19): 3447-3450, 1997.

Islip and White, "236. Some Reactions of 2-(3-Oxindolyl)ethylamines," *Journal of the Chemical Society* 1201-1204, 1964.

Itoh et al., "Introduction of a Hydroxy Group at the Para Position and $N$-Iodophenylation of $N$-Arylamides Using Phenyliodine(III) Bis(Trifluoracetate)," *J. Org. Chem.* 67: 7424-7428, 2002.

Jarvis et al., "A-803467, a potent and selective $Na_v1.8$ sodium channel blocker, attenuates neuropathic and inflammatory pain in the rat," *PNAS* 104(20): 8520-8525, May 15, 2007.

Jensen et al., "Cognitive Testing and Revision of the Pain Quality Assessment Scale," *Clin.J. Pain* 29(5): 400-410, May 2013.

Jorgensen and Berteau, "Thyroxine Analogs. 21. *o*- and *m*-L-Thyroxine and Related Compounds," *Journal of Medicinal Chemistry* 14(12): 1199-1202, 1971.

Julian et al., "Studies in the Indole Series. VI. On the Synthesis of Oxytryptophan and Further Studies of 3-Alkylation of Oxindoles," *Journal of the American Chemical Society* 57: 2026-2029, Nov. 1935.

Julian et al., "Studies in the Indole Series. VIII. Yohimbine (Part 1). The Mechanism of Dehydrogenation of Yohimbine and Related Compounds," *Journal of the American Chemical Society* 70: 174-179, Jan. 1948.

Kaila et al., "Synthesis and Biological Evaluation of Quinoline Salicylic Acids as P-Selectin Antagonists," *J. Med. Chem.* 50: 21-39, 2007.

Kamara et al., "The First Direct Transformation of 2,2′-Dihydroxychalcones into Coumestans,", *Tetrahedron* 55: 861-868, 1999.

Kamiya et al., "A Nonsense Mutation of the Sodium Channel Gene *SCN2A* in a Patient with Intractable Epilepsy and Mental Decline," *Journal of Neuroscience* 24(11): 2690-2698, Mar. 17, 2004.

Kang et al., "Pteropodine and isopteropodine positively modulate the function of rat muscarinic $M_1$ and $5-HT_2$ receptors expressed in *Xenopus* oocyte," *European Journal of Pharmacology* 444: 39-45, 2002.

Karp et al., "Preparation of 4-Hydroxy-2-trifluoromethylthiophene: A Novel Bioisostere of α,α,α-Trifluoro-*m*-cresol," *Synthesis* 8: 1078-1080, 2000.

(56) References Cited

OTHER PUBLICATIONS

Kellgren et al., "Radiological Assessment of Osteo-Arthrosis," *Ann. Rheum. Dis.* 16: 494-502, 1957.
Kende et al., "Intramolecular Radical Cyclization of Phenolic Enolates," *J. Am. Chem. Soc.* 110: 2210-2218, 1988.
Kim et al., "BACE1 regulates voltage-gated sodium channels and neuronal activity," *Nature Cell Biology* 9(7): 755-764, Jul. 2007.
Kim et al., "Design, synthesis, and evaluation of dioxane-based antiviral agents targeted against the Sindbis virus capsid protein," *Bioorganic & Medicinal Chemistry Letters* 15: 3207-3211, 2005.
King et al., "Hydroxy-quinoxalines and -phenazines, and Experiments on the Preparation of Hydroxyquinoxaline Di-$N$-oxides," *J. Chem. Soc.* 3012-3016, 1949.
Kirmse et al., "Intramolecular Reactivity of Arylcarbenes: Derivatives of $o$-Tolylcarbene," *J. Org. Chem.* 59: 3821-3829, 1994.
Kis-Toth et al., "Voltage-Gated Sodium Channel Nav1.7 Maintains the Membrane Potential and Regulates the Activation and Chemokine-Induced Migration of a Monocyte-Derived Dendritic Cell Subset," *The Journal of Immunology* 187: 1273-1280, 2011.
Klugbauer et al., "Structure and functional expression of a new member of the tetrodotoxin-sensitive voltage-activated sodium channel family from human neuroendocrine cells," *EMBO J.* 14(6): 1084-1090, 1995.
Kobayashi and Furukawa, "Studies on Indole Derivatives. I. Synthesis of 3-Phenyl-9$H$-pyridazino-[3,4-$b$]indole Derivatives," *Chemical & Pharmaceutical Bulletin* 12(10): 1129-1135, Oct. 1964.
Kollmar et al., "2-Amino-3-Fluorobenzoic Acid [Benzoic acid, 2-amino-3-fluoro-]," *Organic Syntheses, Coll.* 79: 196, 2002, 5 pages.
Kornet and Thio, "Oxindole-3-spiropyrrolidines and -piperidines. Synthesis and Local Anesthetic Activity," *Journal of Medicinal Chemistry* 19(7): 892-898, 1976.
Kost et al., "Postherpetic Neuralgia—Pathogenesis, Treatment, and Prevention," *The New England Journal of Medicine* 335(1): 32-42, Jul. 4, 1996.
Kotha et al., "Recent applications of the Suzuki-Miyaura cross-coupling reaction in organic synthesis," *Tetrahedron* 58: 9633-9695, 2002.
Kubo et al., "Michael Additions of Indoles to 2-oxoindolin-3-ylidene Ketones," *Heterocycles* 4(10), 1675-1680, 1976.
Kumar et al., "A New Route to Spiropyrrolidinyl-oxindole Alkaloids via Iodide Ion Induced Rearrangement of [($N$-Aziridinomethylthio)methylene]-2-oxindoles," *Organic Letters* 3(26): 4193-4196, 2001.
Kuzma et al., "Progress in the Development of Ultra-Long-Acting Local Anesthetics," *Regional Anesthesia* 22(6): 543-551, Nov.-Dec. 1997.
Lackey and Sternbach, "Synthesis of Substituted Quinoline-4-carboxylic Acids," *Synthesis*: 993-997, Oct. 1993.
Lai et al., "The role of voltage-gated sodium channels in neuropathic pain," *Current Opinion in Neurobiology* 13:291-297, 2003.
Lange et al., "Regioselective Aminomethylations of Bicyclic Phenols," *Heterocycles* 53(1): 197- 204, 2000.
Laniado et al., "Short Communication: Expression and Functional Analysis of Voltage-Activated NA$^+$ Channels in Human Prostate Cancer Cell Lines and their Contribution to Invasion in Vitro," *American Journal of Pathology* 150(4): 1213-1221, Apr. 1997.
Laus et al., "Analysis of the kinetics of isomerization of spiro oxindole alkaloids," *J. Chem. Soc., Perkin Trans.* 2: 1931-1936, 1996.
Laus, "Kinetics of isomerization of tetracyclic spiro oxindole alkaloids," *J. Chem. Soc., Perkin Trans.* 2: 315-317, 1998.
Le Bourdonnec et al., "Medicinal Chemistry Strategies to Reduce CYP2D6 Inhibitory Activity of Lead Candidates," *Current Medicinal Chemistry* 16: 3093-3121, 2009.
Lee-Son et al., "Stereoselective Inhibition of Neuronal Sodium Channels by Local Anesthetics," *Anesthesiology* 77: 324-335, 1992.

Lerchner and Carreira, "Synthesis of (±)-Strychnofoline via a Highly Convergent Selective Annulation Reaction," *Chem. Eur. J.* 12: 8208-8219, 2006.
Leuwer et al., "An improved model for the binding of lidocaine and structurally related local anaesthetics to fast-inactivated voltage-operated sodium channels, showing evidence of cooperativity," *British Journal of Pharmacology* 141(1): 47-54, 2004.
Li et al., "A case of primary erythermalgia with prurigo," *Clinical and Experimental Dermatology* 34: e313-e314, 2009.
Li et al., "Emerging drug targets for pain treatment," *European Journal of Pharmacology* 681: 1-5, 2012.
Lima, "Disclosure: Drugs and chirality: a brief approach," *Química Nova* 20(6): 657-663, 1997 (with translation), 19 pages.
Lindemann et al., "Zur Kenntnis der Indoxazene," *Justus Liebigs Annalen der Chemie* 456: 284-311, 1927.
Lindwall and Maclennan, "A Condensation of Acetophenone with Isatin by the Knoevenagel Method," *Journal of the American Chemical Society* 54: 4739-4744, Dec. 1932.
Liu et al., "Mutations in Cardiac Sodium Channels: Clinical Implications," *Am. J. Pharmacogenomics* 3(3): 173-179, 2003.
Lorenz et al., "Binary and ternary phase diagrams of two enantiomers in solvent systems,", *Thermochimica Acta* 382: 129-142, 2002.
Lossin et al., "Molecular Basis of an Inherited Epilepsy," *Neuron* 34: 877-884, Jun. 13, 2002.
Loudon and Ogg, "2:3-Dihydro-3-oxobenz-1:4-oxazines,"*J. Chem. Soc.*: 739-744, 1955.
Lund et al., *Surgery—Gynecology and Obstetrics—An International Journal of Surgery* vol. 79, The Surgical Publishing Company of Chicago, 1944, "The Estimation of Areas of Burns", 352-358.
Lutz and Clark, "Acid-Catalyzed Rearrangements of the γ-(Methylanilino)lactone of cis-β-(p-Bromobenzoyl)-β-methylacrylic Acid, and of trans-β-(p-Bromobenzoyl)acrylic Methylanilide, to Oxindoles," *J. Org. Chem.* 25: 193-196, Feb. 1960.
Lyalin et al., [title unavailable], *Zhurnal Organicheskoi Khimii* 20(4): 846-849, 1984.
Ma and Cai, "$N,N$-Dimethyl Glycine-Promoted Ullmann Coupling Reaction of Phenols and Aryl Halides," *Organic Letters* 5(21): 3799-3802, 2003.
MacNicol, "Clathrates and Molecular Inclusion Phenomena," *Chemical Society Reviews* 7(1): 65-87, 1978.
Maercker and Theysohn, "Versuche zur Umlagerung von 2-Cyclopropyl-äthyl-Anionen," *Liebigs Ann. Chem.* 759: 132-157, 1972.
Maginnity and Gaulin, "Derivatives of $o$-, $m$- and $p$-Aminobenzotrifluoride," *J. Am. Chem. Soc.* 73: 3579-3580, Aug. 1951.
Majumdar et al., "1-Alkylisatins via Aldol-Retro-aldol Condensation," *J. Chem. Research (S)*, 460-461, 1996.
Mann et al., "The Synthesis of Lignans and Related Structures using Quinodimethanes and Isobenzofurans: Approaches to the Podophyllins," *J. Chem. Soc. Perkin Trans. I*: 2081-2088, 1984.
Mannaioni et al., "Tryptophan Metabolism and Hepatic Encephalopathy. Studies on the Sedative Properties of Oxindole," *Advances in experimental medicine and biology* 467: 155-167, 1999.
Mao and Baldwin, "New Spirocyclic Oxindole Synthesis Based on a Hetero Claisen Rearrangement," *Organic Letters* 6(14): 2425-2428, 2004.
Mao and Chen, "Systemic lidocaine for neuropathic pain relief," *Pain* 87: 7-17, 2000.
Marcantonio et al., "An Investigation into Causes and Effects of High Cyanide Levels in the Palladium-Catalyzed Cyanation Reaction," *Organic Letters* 6(21): 3723-3725, 2004.
Marti and Carreira, "Construction of Spiro[pyrrolidine-3,3'-oxindoles]—Recent Applications to the Synthesis of Oxindole Alkaloids," *Eur. J. Org. Chem.* 2209-2219, 2003.
Marti and Carreira, "Total Synthesis of (—)-Spirotryprostatin B: Synthesis and Related Studies," *J. Am. Chem. Soc.* 127(32): 11505-11515, 2005.
McGowan et al., "A Peripherally Acting Na$_v$1.7 Sodium Channel Blocker Reverses Hyperalgesia and Allodynia on Rat Models of Inflammatory and Neuropathic Pain," *Anesthesia & Analgesia* 109(3): 951-958, Sep. 2009.

(56) References Cited

OTHER PUBLICATIONS

McMurtrey and Daves, Jr., "König's Adducts of N-Alkyl(aryl)aminoethanols and Quinones. 3,4-Dihydro-4-alkyl(aryl)-8a-hydroxy-2H-1,4,benzoxazin-6(8aH)-ones," *J. Org. Chem.* 35(12): 4252-4253, 1970.

McNeal et al., "[$^3$H]Batrachotoxinin a 20α-Benzoate Binding to Voltage-Sensitive Sodium Channels: A Rapid and Quantitative Assay for Local Anesthetic Activity in a Variety of Drugs," *J. Med. Chem.* 28(3): 381-388, 1985.

Meisler et al., "Sodium channel gene family: epilepsy mutations, gene interactions and modifier effects," *J. Physiol.* 588.11: 1841-1848, 2010.

Messier et al., "Exercise and Dietary Weight Loss in Overweight and Obese Older Adults With Knee Osteoarthritis," *Arthritis & Rheumatism* 50(5): 1501-1510, May 2004.

Miyake et al., "Preparation and Synthetic Applications of 2-Halotryptamines: Synthesis of Elacomin and Isoelacomine," *Organic Letters* 6(5): 711-713, 2004.

Miyamoto et al., "Highly Diastereoselective One-Pot Synthesis of Spirocyclic Oxindoles through Intramolecular Ullmann Coupling and Claisen Rearrangement," *Angew. Chem. Int. Ed.* 45: 2274-2277, 2006.

Miyaura and Suzuki, "Palladium-Catalyzed Cross-Coupling Reactions of Organoboron Compounds," *Chem. Rev.* 95: 2457-2483, 1995.

Morie et al., "Asymmetric Synthesis of the Enantiomers of 2-Aminomethyl-4-(4-Fluorobenzyl)morpholine, an Intermediate of Mosapride, a Gastroprokinetic Agent," *Heterocycles* 38(5): 1033-1040, 1994.

Morinville et al., "Distribution of the Voltage-Gated Sodium Channel $Na_v1.7$ in the Rat: Expression in the Autonomic and Endocrine Systems," *Journal of Comparative Neurology* 504: 680-689, 2007.

Morton et al., "Novel solid-phase synthesis of 1,5-benzothiazepine-4-one derivatives," *Tetrahedron Letters* 41: 3029-3033, 2000.

Muci and Buchwald, "Practical Palladium Catalysts for C—N and C—O Bond Formation," *Topics in Current Chemistry* 219: 131-209, 2002.

Muhammad et al., "Two stereoisomeric pentacyclic oxindole alkaloids from *Uncaria tomentosa*; uncarine C and uncarine E," *Acta Cyst.* C57: 480-482, 2001.

Nagakura et al., "Allodynia and Hyperalgesia in Adjuvant-Induced Arthritic Rats: Time Course of Progression and Efficacy of Analgesics," *The Journal of Pharmacology and Experimental Therapeutics* 306(2): 490-497, 2003, obtained from URL=http://jpet.aspetjournals.org, download date Aug. 14, 2009.

Nagamura and Saito, "Antitumor Antibiotics: Duocarmycins," *Chemistry of Heterocyclic Compounds* 34(12): 1386-1405, 1998.

Nagamura et al., "Wagner-Meerwein Rearrangement of Duocarmycins," *Chem. Pharm. Bull.* 44(5): 933-939, May 1996.

Nair et al., "Formal dipolar cycloaddition of allylsilanes to o-quinonoid compounds: a convenient route to benzofused and spirofused heterocycles," *Tetrahedron Letters* 43: 5349-5351, 2002.

Nair et al., "N-Heterocyclic Carbene Catalyzed Reaction of Enals and 1,2-Dicarbonyl Compounds: Stereoselective Synthesis of Spiro γ-Butyrolactones," *Org. Lett.* 8(3): 507-509, 2006.

Nakamura et al., "Cancer preventive agents, Part 2: Synthesis and evaluation of 2-phenyl-4-quinolone and 9-oxo-9,10-dihydroacridine derivatives as novel antitumor promoters," *Bioorganic & Medicinal Chemistry* 13: 4396-4401, 2005.

Namer et al., "Separate Peripheral Pathways for Pruritus in Man," *J. Neurophysiol.* 100: 2062-2069, 2008.

Newkome et al., "α-Methyl Functionalization of Electron-Poor Heterocycles: Free Radical Chlorination," *Synthesis* 676-679, Aug. 1984.

Nicolaus, *Decision Making in Drug Research*, Raven Press, New York, 1983, Franz Gross (ed.), "Symbiotic Approach to Drug Design," pp. 173-186.

Niemann et al., "The Synthesis of 3'-Fluoro-*dl*-thyronine and Some of its Iodinated Derivatives," *J. Am. Chem. Soc.* 63: 609-611, Feb. 1941.

Oaklander et al., "Intractable postherpetic itch and cutaneous deafferentation after facial shingles," *Pain* 96: 9-12, 2002.

Oguri et al., "Amino Acids and Peptides. XXVIII. A New Synthesis of α-Amino Acid Derivatives by Alkylation of Schiff Bases derived from Glycine and Alanine," *Chem. Pharm. Bull.* 25(9): 2287-2291, 1977.

Okita and Isobe, "Synthesis of the Pentacyclic Intermediate for Dynemicin A and Unusual Formation of Spiro-oxindole Ring," *Tetrahedron* 50(38): 11143-11152, 1994.

Onishi et al., "Concise, Asymmetric Total Synthesis of Spirotryprostatin A," *Organic Letters* 5(17): 3135-3137, 2003.

Onishi et al., "Concise, asymmetric total synthesis of spirotryprostatin A," *Tetrahedron* 60: 9503-9515, 2004.

Ooi and Maruoka, "Recent Advances in Asymmetric Phase-Transfer Catalysis," *Angew. Chem. Int. Ed.* 46: 4222-4266, 2007.

Orlova et al., "Synthesis of 2,3,4,5-Tetrahydro-1,5-Benzox(and Thi)azepines and Their Utilization for the Preparation of Condensed Indoles," Translated from *Khimiya Geterotsiklicheskikh Soedinenii* 9: 1262-1266, Sep. 1975, 5 pages.

Overman and Watson, "Diastereoselection in the Formation of Spirocyclic Oxindoles by the Intramolecular Heck Reaction," *J. Org. Chem.* 71: 2587-2599, 2006.

Papale et al., "Heterozygous mutations of the voltage-gated sodium channel *SCN8A* are associated with spike-wave discharges and absence epilepsy in mice," *Human Molecular Genetics* 18(9): 1633-1641, 2009.

Patani and LaVoie, "Bioisosterism: A Rational Approach in Drug Design," *Chem. Rev.* 96(8): 3147-3176, 1996.

Pearn, "Neurology of ciguatera," *J.Neurol. Neurosurg. Psychiatry* 70: 4-8, 2001.

Peat et al., "Knee pain and osteoarthritis in older adults: a review of community burden and current use of primary health care," *Ann. Rheum. Dis.* 60: 91-97, 2001.

Pereira et al., "Severe epilepsy, retardation, and dysmorphic features with a 2q deletion including *SCN1A* and *SCN2A*," *Neurology* 63: 191-192, 2004.

Pham et al., "Outcome Variables for Osteoarthritis Clinical Trials: The OMERACT-OARSI Set of Responder Criteria," *J. Rheumatol.* 30: 1648-1654, 2003.

Pietra and Tacconi, "α-Alkyl- and α-aryl-N-methyltryptamines," *Farmaco, Edizione Scientifica* 14: 854-866, 1959, CAPLUS Database Accession No. 1960:50362, 1 page, Abstract only.

Popp and Pajouhesh, "Potential Anticonvulsants IV: Condensation of Isatin with Benzoylacetone and Isopropyl Methyl Ketone," *Journal of Pharmaceutical Sciences* 71(9): 1052-1054, Sep. 1982.

Popp et al., "Synthesis of Potential Anticonvulsants: Consensation of Isatins with Acetone and Related Ketones," *Journal of Pharmaceutical Sciences* 69(10): 1235-1237, Oct. 1980.

Popp, "Potential Anticonvulsants. V. The Condensation of Isatins with C-Acetyl Heterocyclic Compounds," *J. Heterocyclic Chem.* 19: 589-592, May-Jun. 1982.

Pouton, "Lipid formulations for oral administration of drugs: non-emulsifying, self-emulsifying and 'self-microemulsifying' drug delivery systems," *European Journal of Pharmaceutical Sciences* 11(Suppl 2): S93-S98, 2000.

Priest, "Future potential and status of selective sodium channel blockers for the treatment of pain," *Current Opinion in Drug Discovery & Development* 12(5): 682-692, 2009.

Puopolo et al., "Roles of Subthreshold Calcium Current and Sodium Current in Spontaneous Firing of Mouse Midbrain Dopamine Neurons," *Journal of Neuroscience* 27(3): 645-656, Jan. 17, 2007.

Raj and Raghunathan, "A Novel Entry into a New Class of Spiro Heterocyclic Framework: A Facile Synthesis of Dispiro[oxindole-1,2,3,4-tetrahydro-naphthalen-1-one]pyrrolidines and Spiro [1,2,3,4-tetrahydro-naphthalen-1-one]pyrrolidines," *Synthetic Communications* 33(7): 1131-1139, 2003.

Raj and Raghunathan, "A novel entry into a new class of spiroheterocyclic framework: regioselective synthesis of dispiro[oxindole-cyclohexanone]-pyrrolidines and dispiro[oxindole-hexahydroindazole]pyrrolidines," *Tetrahedron* 57: 10293-10298, 2001.

(56) References Cited

OTHER PUBLICATIONS

Raj et al., "Synthesis, Antimicrobial and Antifungal Activity of a New Class of Spiro Pyrrolidines," *Bioorganic & Medicinal Chemistry* 11: 407-419, 2003.

Raymond et al., "Expression of Alternatively Spliced Sodium Channel α-Subunit Genes," *Journal of Biological Chemistry* 279(44): 46234-46241, Oct. 29, 2004.

Reddy et al., "Synthesis and Pharmacological Evaluation of N,N-Diarylguanidines as Potent Sodium Channel Blockers and Anticonvulsant Agents," *J. Med. Chem.* 41(17): 3298-3302, 1998.

Rehn et al., "The Three-Component Reaction between Isatin, α-Amino Acids, and Dipolarophiles," *Eur. J. Org. Chem.* 413-418, 2004.

Reimann et al., "Pain perception is altered by a nucleotide polymorphism in SCN9A," *PNAS* 107(11): 5148-5153, Mar. 16, 2010.

Ren and Dubner, "Enhanced Descending Modulation of Nociception in Rats With Persistent Hindpaw Inflamation," *Journal of Neurophysiology* 76(5): 3025-3037, Nov. 1996.

Rhodes et al., "Noninactivating voltage-gated sodium channels in severe myoclonic epilepsy of infancy," *PNAS* 101(30): 11147-11152, Jul. 27, 2004.

Rivalle and Bisagni, "Ethyl (4-N-Acylaminopyridin-3-yl)glyoxylate and 5-Azaisatin as New Synthons for a Route to Various New Polyheterocycles," *J. Heterocyclic Chem.* 34: 441-444, Mar.-Apr. 1997.

Rosevear and Wilshire, "Cyclization Reactions in Azole Chemistry: The Reaction of Some Azoles with o-Fluoro-acetophenone, o-Fluorobenzaldehyde and o-Fluorobenzophenone," *Aust. J. Chem.* 44: 1097-1114, 1991.

Ross et al., "Loss of Inhibitory Interneurons in the Dorsal Spinal Cord and Elevated Itch in Bhlhb5 Mutant Mice," *Neuron* 65: 886-898, Mar. 25, 2010.

Rossiter, "A convenient synthesis of 3-methyleneoxindoles: cytotoxic metabolites of indole-3-acetic acids," *Tetrahedron Letters* 43: 4671-4673, 2002.

Rowbotham et al., "Zoster-associated pain and neural dysfunction," *Pain* 93: 1-5, 2001.

Ruan et al., "Sodium channel mutations and arrhythmias," *Nature Reviews Cardiology* 6: 337-348, May 2009.

Sadler, "Separation of Isomeric Isatins," *J. Org. Chem.* 21(2): 169-170, 1956.

Saenger, "Cyclodextrin Inclusion Compounds in Research and Industry," *Angew. Chem. Int. Ed. Engl* 19: 344-362, 1980.

Saishin Souyaku-Kagaku, 1st volume, Chapter 21, Yakubutsu no Sayou no Rittai-Kagaku II: Enantiomer, Ken-ichiro Otsuka, Technomics Corporation, 1998, 1st edition, pp. 475-501, 28 pages.

Sakaki et al., "Discovery of IRL 3461: A Novel and Potent Endothelin Antagonist With Balanced $ET_A/ET_B$ Affinity," *Biooganic & Medicinal Chemistry Letters* 8: 2241-2246, 1998.

Sauviat et al., "Blockade of sodium channels by Bistramide A in voltage-clamped frog skeletal muscle fibres," *Biochimica et Biophysica Acta* 1103: 109-114, 1992.

Sawyer, "Recent Advances in Diaryl Ether Synthesis," *Tetrahedron* 56: 5045-5065, 2000.

Schmelz et al., "Specific C-Receptors for Itch in Human Skin," *The Journal of Neuroscience* 17(20): 8003-8008, Oct. 15, 1997.

Schnyder et al., "Synthesis of Primary Aromatic Amides by Aminocarbonylation of Aryl Halides Using Formamide as an Ammonia Synthon," *J. Org. Chem.* 66: 4311-4315, 2001.

Schulenburg and Archer, "An Unusual Base-catalyzed Cyclization," *Journal of the American Chemical Society* 83(14): 3091-3096, Jul. 20, 1961.

Sebahar et al., "Asymmetric, stereocontrolled total synthesis of (+) and (—)-spirotryprostatin B via a diastereoselective azomethine ylide [1,3]-dipolar cycloaddition reaction," *Tetrahedron* 58: 6311-6322, 2002.

Shin et al., "Potent inhibition of CYP2D6 by haloperidol metabolites: stereoselective inhibition by reduced haloperidol," *J. Clin. Pharmacol.* 51: 45-52, 2001.

Shin-Jikkenn Kagaku Koza I, Kihon-sosa, 1975, pp. 325-327, 4 pages.

Shoop et al., "Anthelmintic Activity of Paraherquamide in Sheep," *J. Parasitol.* 76(3): 349-351, Jun. 1990.

Simas et al., "Regioselective Lithiation of Resorcinol Derivatives: Synthesis of Mono O-MOM- and O-Benzylresorcinols Prenylated at C-2 or C-4 Positions," *Synthesis* 6: 1017-1021, 1999.

Singh et al., "Novel cAMP PDE III Inhibitors: Imidazo[4,5-b]pyridine-2(3H)-ones and Thiazolo[4,5-b]pyridin-2(3H)-ones and Their Analogs," *J. Med. Chem.* 37: 248-254, 1994.

Sircar et al., "Synthesis and SAR of N-Benzoyl-1-Biphenylalanine Dervatives: Discovery of TR-14035, A Dual $α_4β_7/α_4β_1$ Integrin Antagonist," *Bioorganic & Medicinal Chemistry Letters* 10: 2051-2066, 2002.

Smith et al., "Sodium channel protein expression enhances the invasiveness of rat and human prostate cancer cells," *FEBS Letters* 423: 19-24, 1998.

Sridhar and Raghunathan, "Rapid Access for the Synthesis of 1-N-Methyl-spiro[2.3']oxindole-spiro[3.7"] (3"-Aryl)-5"-methyl-3",3a",4",5",6",7"-hexahydro-2H-pyrazolo[4,3-c]pyridine-4-aryl-pyrrolidines Through Sequential 1,3-Dipolar Cycloaddition and Annulation," *Synthetic Communications* 36: 21-29, 2006.

Steinhoff et al., "Proteinase-Activated Receptor-2 Mediates Itch: A Novel Pathway for Pruritus in Human Skin," *Journal of Neuroscience* 23(15): 6176-6180, Jul. 16, 2003.

Stella and NTI-ADDAE, "Prodrug strategies to overcome poor water solubility," *Advanced Drug Delivery Reviews* 59: 677-694, 2007.

Subramaniyan et al., "A facile entry into a new class of spiroheterocycles: synthesis of dispiro[oxindolechromanone/flavanone/tetralone]pyrroloisoquinoline ring systems," *Tetrahedron* 58: 9075-9079, 2002.

Suchý et al., "Synthesis, Absolute Configuration, and Enantiomeric Enrichment of a Cruciferous Oxindole Phytoalexin, (S)-(—)-Spirobrassinin, and Its Oxazoline Analog," *J. Org. Chem.* 66: 3940-3947, 2001.

Swamy et al., "Mitsunobu and Related Reactions: Advances and Applications," *Chem. Rev.* 109: 2551-2651, 2009.

Tacconi et al., "Heterodiene Syntheses—V 1,2- versus 1,4-cycloaddition reactions of enamines to n-substituted 3-oxindolideneacetopheones," *Tetrahedron* 27: 561-579, 1971.

Takahashi et al., "Palladium(0)-Catalyzed Carbonylation on the Multipin™ System," *Tetrahedron Letters* 40: 7843-7846, 1999.

Tamaoka, "Paramyotonia Congenita and Skeletal Sodium Channelopathy," *Internal Medicine* 42(9): 769-770, Sep. 2003.

Tanelian and Brose, "Neuropathic Pain Can Be Relieved by Drugs That Are Use-dependent Sodium Channel Blockers: Lidocaine, Carbamazepine, and Mexiletine," *Anesthesiology* 74(5): 949-951, May 1991.

Ting et al., "Substituted 1,3-Dihydro-2H-pyrrolo[2,3-b]pyridin-2-ones as Potential Antiinflammatory Agents," *J. Med. Chem.* 33(10): 2697-2706, 1990.

Tokunaga et al., "Oxindole Derivatives as Orally Active Potent Growth Hormone Secretagogues," *J. Med. Chem.* 44(26): 4641-4649, 2001.

Trost and Brennan, "Palladium Asymmetric Allylic Alkylation of Prochiral Nucleophiles: Horsfiline," *Org. Lett.* 8(10): 2027-2030, 2006.

Trost and Frederiksen, "Palladium-Catalyzed Asymmetric Allylation of Prochiral Nucleophiles: Synthesis of 3-Allyl-3-Aryl Oxindoles," *Angew. Chem. Int. Ed.* 44: 308-310, 2005.

Twycross et al., "Itch: scratching more than the surface," *Q. J. Med.* 96: 7-26, 2003.

Usman et al., "1-Acetyl-3-(2-chloro-2,3-dihydrobenzofuran-3-yl)-1,2-dihydro-3-hydroxy-2-oxo-3H-indole," *Acta Cryst.* E58: o37-o39, 2002.

Venkatesan et al., "Total Synthesis of SR 121463 A, A Highly Potent and Selective Vasopressin $V_2$ Receptor Antagonist," *Journal of Organic Chemistry* 66(11): 3653-3661, Jun. 1, 2001.

Viaud et al., "Pyrrolo[2,3-b]pyridin-2(2H)-one Derivatives as Potential Non-opioid Analgesic Agents," *Pharmaceutical Sciences* 3: 283-287, 1997.

(56) References Cited

OTHER PUBLICATIONS

Viaud et al., "Acylation of Oxazolo[4,5-*b*]pyridin-2(3*H*)-ones, 2-Phenyloxazolo[4,5-*b*]pyridines and Pyrrolo[2,3-*b*]pyridin-2(2*H*)-ones," *Tetrahedron* 53(14): 5159-5168, 1997.

Villamil et al., "Efficacy of lidocaine in the treatment of pruritus in patients with chronic cholestatic liver diseases," *The American Journal of Medicine* 118: 1160-1163, 2005.

Vippagunta et al., "Crystalline solids," *Advanced Drug Delivery Reviews* 48: 3-26, 2001.

Walker et al., "Limitations in Ring Rearrangement of Fused γ-Lactams Imposed by a Quaternary Carbon Atom. Cyclization of Acid Lactams to Spiro Keto Lactams," *J. Org. Chem.* 30(9): 2973-2983, Sep. 1965.

Wang and Ganesan, "A Biomimetic Total Synthesis of (—)-Spirotryprostatin B and Related Studies," *J. Org. Chem.* 65(15): 4685-4693, 2000.

Wang and Yosipovitch, "New insights into the pathophysiology and treatment of chronic itch in patients with End-stage renal disease, Chronic liver disease and Lymphoma," *Int. J. Dermatol.* 49(1): 1-11, Jan. 2010.

Watanabe et al., "$Na_v2$/NaG Channel is Involved in Control of Salt-Intake Behavior in the CNS," *Journal of Neuroscience* 20(20): 7743-7751, Oct. 15, 2000.

Weaver et al., "Cytochrome P450 Inhibition Using Recombinant Proteins and Mass Spectrometry/Multiple Reaction Monitoring Technology in a Cassette Incubation," *Drug Metabolism and Disposition* 31(7): 955-966, 2003.

Weber and Czugler, "Functional Group Assisted Clathrate Formation—Scissor-Like and Roof-Shaped Host Molecules," *Topics in Current Chemistry* 149: 45-135, 1988.

Weidmann et al., "2-[(2-Pyridylmethyl)sulfinyl]-1*H*-thieno[3,4-*d*]imidazoles. A Novel Class of Gastric $H^+/K^+$-ATPase Inhibitors," *Med. Chem.* 35: 438-450, 1992.

Wolfe et al., "Preference for Nonsteroidal Antiinflammatory Drugs Over Acetaminophen by Rheumatic Disease Patients," *Arthritis & Rheumatism* 43(2): 378-385, Feb. 2000.

Wolff (ed.), *Burger's Medicinal Chemistry and Drug Discovery*, Fifth Edition, vol. I: Principles and Practice, John Wiley & Sons, Inc., New York, New York, 1994, pp. 975-977.

Wood et al., "Voltage-Gated Sodium Channels and Pain Pathways," *J. Neurobiol.* 61: 55-71, 2004.

Wrona et al., "Hydroxyl Radical-Mediated Oxidation of Serotonin: Potential Insights into the Neurotoxicity of Methamphetamine," *J. Neurochem.* 64(3): 1390-1400, 1995.

Wu et al., "The Effect of Hypercholesterolemia on the Sodium Inward Currents in Cardiac Myocyte," *J. Mol. Cell. Cardiol.* 27: 1263-1269, 1995.

Xiao and Bennett, "C-fiber spontaneous discharge evoked by chronic inflammation is suppressed by a long-term infusion of lidocaine yielding nanogram per milliliter plasma levels," *Pain* 137: 218-228, 2008.

Yang and Williams, "Palladium-Catalyzed Cyanation of Aryl Bromides Promoted by Low-Level Organotin Compounds," *Organic Letters* 6(17): 2837-2840, 2004.

Yang et al., "Nucleophilic-Type Radical Cyclizations of Indoles: Conversion of 2-Cyano 3-Substituted Indoles to Spiro-Annelated Indolines and Tetrahydrocarbazolones," *J. Org. Chem.* 58: 3100-3105, 1993.

Zhang et al., "Crystal structure of *syn*-1-acetyl-9'aH-8'-methoxyspiro[indole-3,2'-oxeto [3',2': 4,5]furo[3,2-*g*][1]benzopyran]2,6'-dione," *Journal of Chemical Crystallography* 33(3): 165-168, Mar. 2003.

Zhang et al., "Photoinduced [2+2] cycloadditions (the Paterno-Büchi reaction) of 1-acetylisatin with enol ethers—regioselectivity, diastereo-selectivity and acid catalysed transformations of the spirooxetane products," *J. Chem. Soc., Perkin Trans.* 1: 345-353, 2002.

Zhao et al., "Voltage-gated sodium channel expression in rat and human epidermal keratinocytes: Evidence for a role in pain," *Pain* 139: 90-105, 2008.

Zinser et al., "Anthelmintic paraherquamides are cholinergic antagonists in gastrointestinal nematodes and mammals," *J. vet. Pharmacol. Therap.* 25: 241-250, 2002.

International Search Report and Written Opinion, mailed Apr. 30, 2015, for PCTAN PCT/US2015/0146270, 11 pages.

Fetell et al., entitled Methods of Treating Pain Associated With Osteoarthritis of a Joint With a Topical Formulation of a Spiro-Oxindole Compound, Office Action, mailed Sep. 18, 2015, for U.S. Appl. No. 14/614,895, 29 pages.

International Search Report and Written Opinion, mailed Apr. 28, 2016, for PCTAN PCT/US2016/016800, 9 pages.

International Search Report and Written Opinion mailed Apr. 28, 2016, for PCTAN PCT/US2016/016800, 9 pages.

METHODS OF TREATING POSTHERPETIC NEURALGIA WITH A TOPICAL FORMULATION OF A SPIRO-OXINDOLE COMPOUND

FIELD OF THE INVENTION

The present invention is directed to methods of treating postherpetic neuralgia in a mammal, preferably a human, wherein the methods comprise administering, preferably periodically administering, to an affected skin area of the mammal a topical pharmaceutical composition comprising one or more excipients and a therapeutically effective amount of a spiro-oxindole compound.

BACKGROUND OF THE INVENTION

Postherpetic neuralgia (PHN) is a complication of herpes zoster (commonly known as shingles) in which pain persists for more than 3 months after resolution of the rash (three months is the most commonly identified duration, although definitions of duration for postherpetic neuralgia vary from more than 1 month to less than 6 years). Postherpetic neuralgia affects between 10% to 15% of people who have herpes zoster and increases with age, affecting up to 70% of those infected who are more than 70 years old (Davies, P. S. and Galer, B. S., *Drugs* 2004, Vol. 64, No. 9, pp. 937-47; Dubinsky, R. M. et al., *Neurology* 2004, Vol. 63, No. 6, pp. 959-65; Kost, R. G. and Staus, S. E., *N. Eng. J. Med.* 1996, Vol. 335, No. 1, pp. 32-42). Elderly patients tend to have more severe and longer lasting postherpetic neuralgia.

Despite the numerous compounds available for treating postherpetic neuralgia, 40% to 50% of postherpetic neuralgia patients do not respond to any treatment (Rowbotham, M. C. and Petersen, K. L., *Pain* 2001, Vol. 93, pp. 1-5). Antiviral therapy for acute herpes zoster has been shown to accelerate clearing of the rash, but a recent meta-analysis showed that it does not reduce the likelihood of the development of postherpetic neuralgia (Chen, N et al., *Cochrane Database Syst. Rev.* 2009 Apr. 15(2):CD006866). Antivirals also have no demonstrable benefit after the rash has cleared and are of no use once postherpetic neuralgia is established. Tricyclic antidepressants were the first analgesic agents that showed efficacy in randomized controlled trials of postherpetic neuralgia, and, subsequently, anticonvulsant agents, strong opioids, and topical analgesics have also demonstrated efficacy.

A topical patch containing 5% lidocaine, a nonselective sodium channel blocker (LIDODERM®, Endo Pharmaceuticals Inc), was approved by the United States (US) Food and Drug Administration (FDA) for the treatment of PHN. In 2004, a subcommittee of the American Academy of Neurology determined that there was solid Class I evidence of efficacy for the lidocaine patch in postherpetic neuralgia (Dubinsky et al. 2004). The lidocaine patch, if perhaps less effective than other approved treatments such as gabapentin and pregabalin (Dworkin, R. H. et al., *Neurology* 2003, Vol. 60, No. 8, pp. 1274-83), is considered highly efficacious in postherpetic neuralgia, although there have been no head-to-head comparisons with other agents and the number-needed-to-treat (NNT) varies from study to study (Davies and Galer 2004). The safety and tolerability of the lidocaine patch has probably contributed most to its widespread use in postherpetic neuralgia. Safety and the reduced risk of drug-drug interactions (DDIs) with a topical formulation are particularly relevant, given the elderly age of most patients affected by postherpetic neuralgia and their need for concomitant medications.

The difficulty of treating postherpetic neuralgia adequately, with many patients refractory to available therapies, indicates that there is an ongoing medical need for new treatment options providing effective topical pain relief of postherpetic neuralgia with a good safety profile with minimal or negligible or systemic exposure of the therapeutic agent.

SUMMARY OF THE INVENTION

The present invention is directed to methods of treating postherpetic neuralgia in a mammal, preferably a human, wherein the methods comprise administering, preferably periodically administering, to an affected skin area of the mammal a topical pharmaceutical composition comprising one or more excipients and a therapeutically effective amount of a spiro-oxindole compound.

Accordingly, one aspect of the invention is a method of treating postherpetic neuralgia in a mammal, wherein the method comprises administering, preferably periodically administering, to an affected skin area of the mammal a topical pharmaceutical composition comprising one or more excipients and a therapeutically effective amount of a spiro-oxindole compound having the following formula:

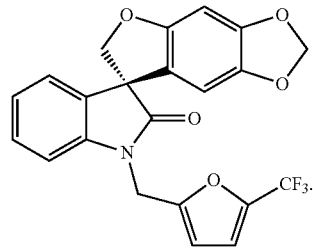 [SMILES: O=C1N(Cc2ccc(C(F)(F)F)o2)c2ccccc2[C@]12COc1cc3c(cc12)OCO3]

Another aspect of the invention is a method of locally treating postherpetic neuralgia in a mammal with minimal or negligible systemic exposure of a spiro-oxindole compound, wherein the method comprises increasing the concentration of the spiro-oxindole compound defined above to a therapeutically effective amount in the affected skin area of the mammal by administering, preferably periodically administering, to the affected skin area a topical pharmaceutical composition comprising one or more excipients and a therapeutically effective amount of the spiro-oxindole compound.

Another aspect is a method of treating postherpetic neuralgia in a mammal, wherein the method comprises administering, preferably periodically administering, to an affected skin area of the mammal a topical pharmaceutical composition comprising one or more excipients and a therapeutically effective amount of the spiro-oxindole compound and a therapeutically effective amount of one or more other therapeutic agents.

Specific embodiments of these aspects of the invention are described in more detail below.

DETAILED DESCRIPTION OF THE INVENTION

As described above in the Summary of the Invention, the present invention is directed to methods of treating postherpetic neuralgia in a mammal, preferably a human, wherein the methods comprise administering, preferably periodically administering, to an affected skin area of the mammal a topical pharmaceutical composition comprising one or more excipients and a therapeutically effective amount of a spiro-oxindole compound. These methods provide minimal to negligible systemic exposure of the spiro-oxindole compound while effectively reducing the severity of the postherpetic neuralgia or alleviating the postherpetic neuralgia due to the increased concentration of the spiro-oxindole compound in the affected dermatome after the administration of the pharmaceutical composition to the affected skin area.

Definitions

Unless defined otherwise in the specification, the following terms and phrases shall have the following meaning:

"A spiro-oxindole compound" or "the spiro-oxindole compound" refers to the compound having the following formula:

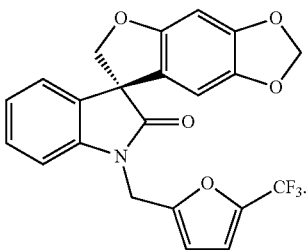 [SMILES: O=C1N(Cc2ccc(C(F)(F)F)o2)c2ccccc2[C@]12COc1cc3c(cc12)OCO3]

A chemical name for this compound is 1'-{[5-(trifluoromethyl)furan-2-yl]methyl}spiro[furo[2,3-f][1,3]benzodioxole-7,3'-indol]-2'(1'H)-one.

"Active ingredient" refers to the substance in a pharmaceutical composition which is biologically active. The active ingredient in the pharmaceutical compositions utilized in the methods of the invention is the spiro-oxindole compound.

"Adverse Event" refers to any untoward medical occurrence in a patient administered a pharmaceutical product, regardless of whether it has a causal relationship with the treatment. An adverse event can therefore be any unfavorable and unintended physical sign, symptom or laboratory parameter that develops or worsens in severity during the course of the study, or significant worsening of the disease under study or of any concurrent disease, whether or not considered related to the study drug. A new condition or the worsening of a pre-existing condition will be considered an adverse event. Stable chronic conditions that are present before study entry and do not worsen during the study will not be considered adverse events.

"Affected skin area" refers to the area of the skin of an affected dermatome of the mammal, preferably a human, where the postherpetic neuralgia is present.

"Affected dermatome" refers to a dermatome of the mammal, preferably a human, which has had a herpes zoster skin rash and where postherpetic neuralgia is present. A dermatome is an area of skin supplied by sensory neurons that arise from a spinal nerve ganglion. The term "affected dermatome" may include more than one dermatome, preferably a dermatome contiguous with the original affected dermatome. Viruses, such as the varicella zoster virus, that lie dormant in nerve ganglia, often cause rash and/or co-existing pain and, after the rash as abated, postherpetic neuralgia in a pattern defined by a dermatome. Such symptoms may not appear across the entire dermatome.

The term "about" when placed before a numerical value "X" herein refers to an interval extending from X minus 10% of X to X plus 10% of X and preferably to an interval extending from X minus 5% of X to X plus 5% of X.

The expression "% w/w" refers to a percentage by weight compared to the total weight of the composition being considered.

"Baseline" refers to that information which is gathered at the beginning of a study from which variations found in the study are measured. Baseline can also be described as a known value or quantity with which an unknown is compared when measured or assessed.

"Postherpetic neuralgia" is a classical neuropathic pain condition in which damage to peripheral sensory nerves (and the dorsal horn regions of the spinal cord) by the varicella zoster virus is believed to generate spontaneous peripheral neural discharges that lead secondarily to hyperexcitability of dorsal horn sensory neurons and result in exaggerated central nervous system (CNS) responses to all input, a condition known as central sensitization (Kost and Straus 1996). Typically, patients with postherpetic neuralgia have both a zone of loss of sensation and zones of altered sensation to light touch and temperature in the dermatome which exhibited the herpes zoster rash. Pain is described as deep aching or burning in quality and may be triggered by non-painful stimulus (mechanical allodynia) or temperature change (warm or cold allodynia). It may last for years, although there is a tendency for it to wane over time. In those patients whose pain is persistent and severe, postherpetic neuralgia becomes debilitating, markedly restricting the patient's activity and quality of life. For purposes of this invention, postherpetic neuralgia is defined as pain present for more than 3 months and less than 6 years after the onset of herpes zoster skin rash affecting a single dermatome (i.e., primary dermatome), pain present more than 6 months and less than 6 years after the onset of herpes zoster skin rash, pain present more than 6 months and less than 5 years after the onset of herpes zoster skin rash, pain present more than 6 months and less than 4 years after the onset of herpes zoster skin rash, pain present more than 6 months and less than 3 years after the onset of herpes zoster skin rash, pain present more than 6 months and less than 2 years after the onset of herpes zoster skin rash, pain present more than 6 months and less than 1 year after the onset of herpes zoster skin rash, or pain present more than 3 months and less than 1 year after the onset of herpes zoster skin rash, or pain present for any length of time more than 3 months and less than 6 years after the onset of herpes zoster skin rash. For treatment purposes, more than one dermatome may be included, provided the affected dermatome is contiguous with the primary dermatome. Allodynia (pain due to a stimulus that does not usually provoke pain) and/or hyperalgesia (increased pain from a stimulus that usually provokes pain) may be present with postherpetic neuralgia.

"Excipient" includes, without limitation, any inactive material that is combined with a spiro-oxindole compound of the invention in order to produce a pharmaceutical composition of the invention for topical administration. The term "excipient" is intended to include, but is not limited to, any solvents, penetration enhancing agents, antioxidants, stiffening agents (i.e., thickeners), ointment bases, antioxidants, adsorbents, demulcents, emollients, preservatives, moisturizers, buffers, adjuvants, carriers, diluents, dye/colorants, solubilizers (including surfactants), wetting agents, dispersing agents, suspending agents, sunscreen agents and stabilizers. "Pharmaceutically acceptable excipient" refers to an excipient, as defined above, which has been approved by a regulatory agency, such as for example, but is not limited to, the United States Food and Drug Administration, the European Medicines Agency or Health Canada, as being acceptable for use in a formulation for the topical administration of a pharmacologically active ingredient, and/or are considered as Generally Recognized As Safe materials (GRAS materials), and/or are listed in the Inactive Ingredients Guide published by the United States Food and Drug Administration. "Pharmaceutically acceptable excipients" can also comprise the acceptable excipients listed in *Remington: The Science and Practice of Pharmacy*, Fox, 21$^{st}$ ed. 2005. Exemplary excipients include, but are not limited to, the following:

- ascorbic acid and esters;
- benzyl alcohol;
- benzyl benzoate;
- butylated hydroxytoluene ("BHT");
- butylated hydroxyanisole ("BHA");
- caprylic/capric triglyceride;
- cetyl alcohol;
- chelating agents (e.g., EDTA and citric acid);
- cholesterol;
- cross-linked acrylic acid based polymers (e.g., Carbopol®);
- decyl methyl sulfoxide;
- diethyl sebacate;
- dimethylamine ("DMA");
- dimethicone;
- dimethyl sulfoxide;
- diethylene glycol monoethyl ether (e.g., Transcutol® P);
- diisopropyl adipate (e.g., Ceraphyl® 230);
- ethanol;
- flavinoid;
- glutathione;
- glycerine;
- glycerol oleate/propylene glycol (e.g., Arlacel 186);
- glycerol monooleate;
- polyoxyl glycerides (glyceryl caprylate/caprate and PEG-8 (polyethylene glycol) caprylate/caprate complex; carpylocaproyl macrogolglycerides (e.g., Labrasol®));
- glyceryl monocaprylate (e.g., Capmul® MCM C8);
- glyceryl monolinoleate (e.g., Maisine™ 35-1);
- glyceryl monooleate (e.g., Peceol™);
- glyceryl monostearate;
- hexylene glycol;
- hydroxypropyl-β-cyclodextrin (HP-β-CD);
- isopropyl alcohol;
- isopropyl myristate;
- laurocapram; (e.g., Azone®);
- lauroyl macrogol-32 glycerides (e.g. Gelucire® 44/14);
- macrogol-15 hydroxystearate (e.g., Solutol® HS15);
- medium chain triglycerides (e.g., Miglyol® 810, Miglyol® 840 or Miglyol® 812);
- methyl laurate;
- N-methyl-2-pyrrolidine (e.g., Pharmasolve®);
- mineral oil;
- mono diglycerides (e.g., Capmul® MCM);
- octyldodecanol;
- oleic acid;
- oleyl alcohol;
- peanut oil;
- 1,2-pentanediol;
- polysorbates (e.g., Tween® 80);
- polyethylene glycol (e.g., PEG-8, PEG 400, PEG1000, PEG 3350, PEG 6000, or Lutrol® E 400);
- polyoxyl 35 castor oil (e.g., Cremophor® EL);
- polyoxyl 40 hydrogenated castor oil (e.g., Cremophor® RH 40);
- propylene glycol;
- propylene glycol diacetate;
- propylene glycol laurate;
- propylene glycol monocaprylate (e.g., Capmul PG-8, Capryol 90);
- propylene glycol monolaurate (e.g., Capmul PG-12);
- propylene glycol monooleate;
- 2-pyrrolidone;
- soybean oil;
- stearyl alcohol;
- sulfobutylether-β-cyclodextrin (e.g., Capitsol®);
- tocopherols (e.g., Vitamin E acetate);
- α-tocopherol polyethylene glycol succinate (TPGS);
- water; and
- white petrolatum.

"Periodically administering" or "periodic administration" as used herein refers to the initial application of a topical pharmaceutical composition of the invention to the affected skin area of the mammal, preferably a human, and then subsequent applications at pre-determined periods of time after the initial application to reduce the severity of the postherpetic neuralgia and/or to alleviate the postherpetic neuralgia.

"Systemic effect" refers to a medical treatment effect that affects the body as a whole, rather than just one part.

"Minimal or negligible systemic exposure" refers to an insignificant concentration of the spiro-oxindole compound in the plasma and tissues of a mammal when compared to the concentration of the spiro-oxindole compound in the affected skin area after the administration of a pharmaceutical composition of the invention comprising the spiro-oxindole to the affected skin area. The affected skin area includes the affected dermatome and the muscle and nerve tissues within the affected dermatome. For purposes of this invention, minimal or negligible systemic exposure occurs when the concentration of the spiro-oxindole compound in the plasma and tissues of the mammal, excluding the affected skin area, is from about 5-fold to about 100-fold less, preferably from about 5-fold to about 50-fold less, more preferably from about 10-fold to about 40-fold less, even more preferably from about 15-fold to about 25-fold less, and most preferably about 20-fold less than the concentration of the spiro-oxindole compound in the affected skin area after administering a pharmaceutical composition of the invention comprising the spiro-oxindole compound to the affected skin area.

"Therapeutically effective amount" as used herein refers to that amount of a topical pharmaceutical composition of the invention or that amount of the spiro-oxindole compound in the topical pharmaceutical compositions of the invention, when administered, preferably periodically administered, to a mammal, preferably a human, is sufficient to effect treatment, as defined below, of postherpetic neuralgia in the mammal and with minimal or negligible systemic exposure of the spiro-oxindole compound to the mammal. The amount of the topical pharmaceutical composition of the invention or the spiro-oxindole compound which constitutes a "therapeutically effective amount" will vary depending on the nature of the postherpetic neuralgia and its severity, other conditions (e.g., sex, age, weight, general health) affecting the health of the human to be treated, and the manner of administration, as well as upon the effectiveness of the pharmaceutical composition used, but can be determined routinely by one of ordinary skill in the art having regard to his own knowledge and to this disclosure.

"Treating" or "treatment" as used herein refers to the treatment of postherpetic neuralgia in a mammal, preferably a human, having postherpetic neuralgia and includes reducing the severity of the postherpetic neuralgia and/or alleviating the postherpetic neuralgia for a period of time following the administration, preferably periodic administration of a topical pharmaceutical composition of the invention.

As described above in the Summary of the Invention, the present invention provides methods of treating postherpetic neuralgia in a mammal, preferably a human, wherein the methods comprise administering, preferably periodically administering, to the affected skin area of the mammal a topical pharmaceutical composition comprising one or more excipients and a therapeutically effective amount of a spiro-oxindole compound. These methods provide excellent penetration of the spiro-oxindole compound into the affected skin area and the affected dermatome, thereby providing a localized reduction of the severity of the postherpetic neuralgia or alleviation of the postherpetic neuralgia with minimal or negligible systemic exposure.

The topical pharmaceutical compositions of the invention are suitable for application to the skin of a mammal, preferably a human, and can be in the form of an ointment, a foam, a cream, a lotion, a gel, a liniment or other spreadable semi-liquid preparation. In one embodiment, a topical pharmaceutical composition of the invention is in the form of an ointment. In another embodiment, a topical pharmaceutical composition of the invention is in the form of a cream. In another embodiment, a topical pharmaceutical composition of the invention is in the form of a liniment. In another embodiment, a topical pharmaceutical composition of the invention is in the form of a lotion. In another embodiment, a topical pharmaceutical composition of the invention is in the form of a gel. In another embodiment, a topical pharmaceutical composition of the invention is in the form of a spreadable semi-liquid preparation.

The topical pharmaceutical compositions utilized in the methods of the invention are prepared as disclosed in U.S. Published Patent Application No. 2013/0143941 A1, the relevant disclosure of which is incorporated in full by reference herein.

Accordingly, one embodiment of the topical pharmaceutical compositions utilized in the methods of the invention is a topical pharmaceutical composition comprising a therapeutically effective amount of the spiro-oxindole compound, and one or more excipients, preferably pharmaceutically acceptable excipients, wherein the excipients are selected from one or more solvents, optionally from one or more penetration enhancing agents, optionally from one or more stiffening agents, optionally from one or more ointment bases, and optionally one or more antioxidants.

Another embodiment of the topical pharmaceutical compositions utilized in the methods of the invention is a topical pharmaceutical composition comprising a therapeutically effective amount of the spiro-oxindole compound, and two or more excipients, preferably pharmaceutically acceptable excipients, wherein the excipients are selected from one or more solvents, optionally from one or more penetration enhancing agents, optionally from one or more stiffening agents, optionally from one or more ointment bases, and optionally from one or more antioxidants.

Another embodiment of the topical pharmaceutical compositions utilized in the methods of the invention is a topical pharmaceutical composition comprising a therapeutically effective amount of the spiro-oxindole compound, and two or more excipients, preferably pharmaceutically acceptable excipients, wherein the excipients are selected from one or more solvents, from one or more penetration enhancing agents, from one or more stiffening agents, from one or more ointment bases, and optionally from one or more antioxidants.

Another embodiment of the topical pharmaceutical compositions utilized in the methods of the invention is a topical pharmaceutical composition comprising a therapeutically effective amount of the spiro-oxindole compound, and one or more excipients, preferably pharmaceutically acceptable excipients, wherein one of the excipients is a solvent selected from polyethylene glycol, diethylene glycol monoethyl ether, polysorbates, alcohols, carpylocaproyl macrogolglycerides, caprylic/capric triglyceride, fatty acid esters, diethyl sebacate, propylene glycol monocaprylate, propylene glycol laurate, mono diglycerides, glyceryl monocaprylate, medium chain triglycerides, hexylene glycol, glyceryl monooleate, 1,2-pentanediol, octyldodecanol, glyceryl mono-linoleate, glycerol oleate/propylene glycol, mineral oil, water, or glycerine.

Another embodiment of the topical pharmaceutical compositions utilized in the methods of the invention is a topical pharmaceutical composition comprising a therapeutically effective amount of the spiro-oxindole compound, and one or more excipients, preferably pharmaceutically acceptable excipients, wherein one of the excipients is a penetration enhancing agent selected from polyoxyl glycerides (Labrasol®), ethanol, propylene glycol laurate, diethyl sebacate, dimethyl sulfoxide, decylmethylsulfoxide, laurocapram, pyrrolidones, surfactants, alcohols, oleic acid, polyethylene glycol, diethylene glycol monoethyl ether, fatty acid esters or Transcutol® P.

Another embodiment of the topical pharmaceutical compositions utilized in the methods of the invention is a topical pharmaceutical composition comprising a therapeutically effective amount of the spiro-oxindole compound, and one or more excipients, preferably pharmaceutically acceptable excipients, wherein one of the excipients is a stiffening agent selected from stearyl alcohol, carbopols, dimethicone or polymers.

Another embodiment of the topical pharmaceutical compositions utilized in the methods of the invention is a topical pharmaceutical composition comprising a therapeutically effective amount of the spiro-oxindole compound, and one or more excipients, preferably pharmaceutically acceptable excipients, wherein one of the excipients is an ointment base selected from polyethylene glycols.

Another embodiment of the topical pharmaceutical compositions utilized in the methods of the invention is a topical pharmaceutical composition comprising a therapeutically effective amount of the spiro-oxindole compound, and one or more excipients, preferably pharmaceutically acceptable excipients, wherein one of the excipients is optionally an antioxidant selected from butylated hydroxytoluene, butylated hydroxyanisole, tocopherols, flavinoid, glutathione, ascorbic acid and esters, dimethyl sulfoxide, or chelating agents.

Another embodiment of the topical pharmaceutical compositions utilized in the methods of the invention is a topical pharmaceutical composition comprising a therapeutically effective amount of the spiro-oxindole compound, and one or more excipients, preferably pharmaceutically acceptable excipients, wherein each excipient is present in a concentration of from about 0.01% w/w to about 99% w/w.

Another embodiment of the topical pharmaceutical compositions utilized in the methods of the invention is a topical pharmaceutical composition comprising a therapeutically effective amount of the spiro-oxindole compound, and one or more excipients, preferably pharmaceutically acceptable excipients, wherein a first excipient is a solvent present at a concentration of from about 30% w/w to about 70% w/w, a second excipient is a penetration enhancing agent present in a concentration of from about 2% w/w to about 25% w/w, a third excipient is a penetration enhancing agent present in a concentration of from about 1% w/w to about 10% w/w, a fourth excipient is a penetration enhancing agent present in a concentration of from about 1% w/w to about 25% w/w, a fifth excipient is a stiffening agent present in a concentration of from about 0.1% w/w to about 10% w/w, a sixth excipient is an antioxidant present in a concentration of from about 0.01% w/w to about 2% w/w, and a seventh excipient is an ointment base present in a concentration of from about 10% w/w to about 50% w/w.

Another embodiment of the topical pharmaceutical compositions utilized in the methods of the invention is a topical pharmaceutical composition comprising a therapeutically effective amount of the spiro-oxindole compound, and one or more excipients, wherein a first excipient is a solvent present at a concentration of from about 45% w/w to about 55% w/w, a second excipient is a penetration enhancing agent present in a concentration of from about 5% w/w to about 15% w/w, a third excipient is a penetration enhancing agent present in a concentration of from about 2.5% w/w to about 7.5% w/w, a fourth excipient is a penetration enhancing agent present in a concentration of from about 2.5% w/w to about 7.5% w/w, a fifth excipient is a stiffening agent present in a concentration of from about 0.1% w/w to about 7.5% w/w, a sixth excipient is optionally an antioxidant present in a concentration of from about 0.05% w/w to about 1% w/w, and a seventh excipient is an ointment base present in a concentration of from about 15% w/w to about 30% w/w.

Another embodiment of the topical pharmaceutical compositions utilized in the methods of the invention is a topical pharmaceutical composition comprising a therapeutically effective amount of the spiro-oxindole compound, and one or more excipients selected from a solvent selected from PEG 400 or PEG 3350; one or more penetration enhancing agents selected from Transcutol® P, oleyl alcohol or isopropyl myristate; a stiffening agent selected from stearyl alcohol; an ointment base selected from PEG 400 or PEG 3350; and optionally an antioxidant selected from butylated hydroxytoluene.

Of this embodiment, a further embodiment is a topical pharmaceutical composition comprising a therapeutically effective amount of the spiro-oxindole compound, wherein PEG 400 is present in a concentration from about 30% w/w to about 70% w/w, Transcutol® P is present in a concentration from about 2% w/w to about 25% w/w, oleyl alcohol is present in a concentration from about 1% w/w to about 10% w/w, isopropyl myristate is present in a concentration from about 1% w/w to about 25% w/w, stearyl alcohol is present in a concentration from about 0.1% w/w to about 10% w/w, BHT is optionally present in a concentration from about 0.01% w/w to about 2% w/w, and PEG 3350 is present in a concentration from about 10% w/w to about 50% w/w.

Of this embodiment, a further embodiment is a topical pharmaceutical composition comprising a therapeutically effective amount of the spiro-oxindole compound, wherein PEG 400 is present in a concentration from about 45% w/w to about 55% w/w, Transcutol® P is present in a concentration from about 5% w/w to about 15% w/w, oleyl alcohol is present in a concentration from about 2.5% w/w to about 7.5% w/w, isopropyl is myristate present in a concentration from about 2.5% w/w to about 7.5% w/w, stearyl alcohol is present in a concentration from about 0.1% w/w to about 7.5% w/w, BHT is optionally present in a concentration from about 0.05% w/w to about 1% w/w, and PEG 3350 is present in a concentration from about 15% w/w to about 30% w/w.

Of all of the above embodiments, a further embodiment is wherein the spiro-oxindole compound is present in the topical pharmaceutical composition at a concentration from about 0.1% w/w to about 10% w/w.

Of this embodiment, a further embodiment is wherein the spiro-oxindole compound is present in the topical pharmaceutical composition at a concentration from about 2% w/w to about 8% w/w.

Test Pharmaceutical Compositions of the Invention

In one embodiment of the invention, the topical pharmaceutical compositions utilized in the methods of the invention comprise 2% to 8% (w/w) of the spiro-oxindole compound; 45% to 55% (w/w) PEG 400; 5% to 15% (w/w) Transcutol® P; 2.5% to 7.5% (w/w) oleyl alcohol; 2.5% to 7.5% (w/w) isopropyl myristate; 0.1% w/w to 7.5% (w/w) stearyl alcohol; 0.05% to 1% (w/w) butylated hydroxytoluene; and 15% to 30% (w/w) PEG 3350. Preferably, the topical pharmaceutical compositions are in ointment form.

Of this embodiment, a topical pharmaceutical composition utilized in the methods of the invention comprises 2.0% (w/w) of the spiro-oxindole compound; 52.9% (w/w) PEG 400; 10% (w/w) Transcutol® P; 5% (w/w) oleyl alcohol; 5% (w/w) isopropyl myristate; 5% (w/w) stearyl alcohol; 0.1% (w/w) butylated hydroxytoluene; and 20% (w/w) PEG 3350. This pharmaceutical composition is referred to herein as the "2% ointment", the "2% pharmaceutical composition of the invention" or the "2% Test Pharmaceutical Composition".

Of this embodiment, another topical pharmaceutical composition utilized in the methods of the invention comprises 4.0% (w/w) of the spiro-oxindole compound; 50.9% (w/w) PEG 400; 10% (w/w) Transcutol® P; 5% (w/w) oleyl alcohol; 5% (w/w) isopropyl myristate; 5% (w/w) stearyl alcohol; 0.1% (w/w) butylated hydroxytoluene; and 20% (w/w) PEG 3350. This pharmaceutical composition is referred to herein as the "4% ointment", the "4% pharmaceutical composition of the invention" or the "4% Test Pharmaceutical Composition".

Of this embodiment, another topical pharmaceutical composition utilized in the methods of the invention comprises 8.0% (w/w) of the spiro-oxindole compound; 46.9% (w/w) PEG 400; 10% (w/w) Transcutol® P; 5% (w/w) oleyl alcohol; 5% (w/w) isopropyl myristate; 5% (w/w) stearyl alcohol; 0.1% (w/w) butylated hydroxytoluene; and 20% (w/w) PEG 3350. This pharmaceutical composition is referred to herein as the "8% ointment", the "8% pharmaceutical composition of the invention" or the "8% Test Pharmaceutical Composition".

Spiro-Oxindole Compound

The active ingredient of the topical pharmaceutical compositions utilized in the methods of the invention is the spiro-oxindole compound having the following formula:

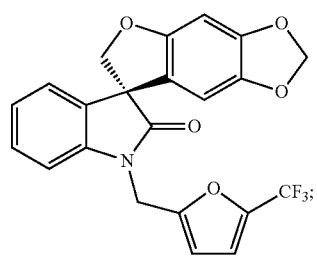 [SMILES: O=C1N(Cc2ccc(C(F)(F)F)o2)c2ccccc2[C@]12COc1cc3c(cc12)OCO3]

which is named as (S)-1'-{[5-(trifluoromethyl)furan-2-yl]methyl}spiro[furo[2,3-f][1,3]benzodioxole-7,3'-indol]-2'(1'H)-one. This spiro-oxindole compound is prepared as disclosed in U.S. Pat. No. 8,450,358, the relevant disclosure of which is incorporated by reference in full.

The above spiro-oxindole compound is a potent, voltage-gated sodium channel ($Na_V$) blocker developed for the treatment of various pain indications, including neuropathic and nociceptive pain. The block of certain neuronal $Na_V$s has been demonstrated as a means for treating pain and continues to offer an approach for developing novel analgesics. In particular, the block of $Na_V1.3$, $Na_V1.7$ and $Na_V1.8$ have the most clinical and/or non-clinical evidence to date in supporting analgesic use.

$Na_V1.3$ is expressed primarily in the central nervous system in neonatal animals and at low levels throughout the body in adults (Raymond, C. K., et al., *J. Biol. Chem.* (2004), 279(44):46234-41). It has been demonstrated to have its expression upregulated in the dorsal horn sensory neurons of rats after nervous system injury (Hains, B. D., et al., *J. Neurosci.* (2003), 23(26):8881-92). Many experts in the field have considered $Na_V1.3$ as a suitable target for pain therapeutics because its expression is induced by nerve injury (Lai, J., et al., *Curr. Opin. Neurobiol.* (2003), (3): 291-72003; Wood, J. N., et al., *J. Neurobiol.* (2004), 61(1): 55-71; Chung, J. M., et al., *Novartis Found Symp.* (2004), 261:19-27; discussion 27-31, 47-54; Priest, B. T., *Curr. Opin. Drug Discov. Devel.* (2009) 12:682-693).

$Na_V1.7$ is expressed primarily in the peripheral nervous system in both sensory and sympathetic neurons (Raymond, C. K., et al., op. cit.). Loss-of-function mutations in SCN9A (the gene encoding the alpha subunit of the $Na_V1.7$ sodium channel) cause a human condition known as congenital indifference to pain characterized by an inability to perceive pain (Cox, J. J., et al., *Nature* (2006), 444:894-98; Goldberg, Y. P., et al., *Clin Genet* (2007), 71:311-9). Gain-of-function mutations in SCN9A are associated with inherited erythromelalgia (IEM) (Drenth, J. P., et al., *J Invest Dermatology* (2005), 124:1333-8), which is characterized by spontaneous or easily evoked severe pain. Furthermore, up to 29% of biopsy-proven cases of idiopathic small-fiber neuropathy manifesting mainly as distal severe pain (Faber, C. G., et al., *Ann Neurol* (2012), 71:26-39) are associated with gain-of-function $Na_V1.7$ channel mutations. The spiro-oxindole compound utilized in the methods of the invention displays a potent blocking effect on $Na_V1.7$. In particular, the potency of the block of the spiro-oxindole compound against $Na_V1.7$ has been shown to be approximately 220-fold greater for the inactivated state ($IC_{50}$=0.05 μM) compared with the resting state ($IC_{50}$=11.3 μM).

The expression of $Na_V1.8$ is predominately in the dorsal root ganglia (DRG) (Raymond, C. K., et al., op. cit.). The upstroke of the action potential in sensory neurons from DRG is primarily carried by current through $Na_V1.8$, so that block of this current is likely to block pain responses (Blair, N. T. and Bean, B. P., *J. Neurosci.* 22: 10277-90). Consistent with this finding, knock-down of $Na_V1.8$ in rats has been achieved by using antisense DNA or small interfering RNAs and virtually complete reversal of neuropathic pain was achieved in the spinal nerve ligation and chronic constriction injury models. A selective blocker of $Na_V1.8$ has been reported and it is effective at blocking both neuropathic and inflammatory pain (Jarvis, M. F. et al., *Proc. Natl. Acad. Sci. USA* (2007), 104 (20), 8520-5).

Topical formulations comprising the spiro-oxindole compound of the invention have demonstrated activity in a variety of nonclinical pain models including the chronic sciatic nerve constriction (chronic constriction injury [CCI]) or Bennett model of neuropathic pain, and the complete Freund's adjuvant (CFA) model of inflammatory pain.

For example, in vivo studies in neuropathic and inflammatory pain models in the rat demonstrated that topical administration of a pharmaceutical composition of the invention provided analgesic relief superior to current marketed topical therapeutics such as lidocaine and diclofenac. In the CFA model of inflammatory pain, the analgesic effects of the topical 8% pharmaceutical composition of the invention comprising the spiro-oxindole compound were obtained at a mean plasma concentration (0.32 ng/mL) that was 120-fold lower than the mean plasma concentration observed at the minimum effective dose of an oral pharmaceutical composition comprising the spiro-oxindole compound in this same model.

A dose-response was observed and the dose associated with pain relief ranged from a minimum effective dose of 2% (w/w) of the spiro-oxindole compound with the greatest effect seen at the highest dose tested of 8% (w/w) of the spiro-oxindole compound. In the CCI model of neuropathic pain, a topical 8% pharmaceutical composition exhibited a degree of efficacy comparable to 25 mg/kg of the spiro-oxindole compound by oral administration, despite systemic plasma exposure of the spiro-oxindole compound (maximum observed concentration, $C_{max}$=3.6 ng/mL) being significantly lower (approximately 20-fold) than that of the oral treatment group. Based on these data, the analgesic effect of a topical formulation of the spiro-oxindole compound in these animal models is considered to be due to a local effect rather than a systemic effect.

A study in minipigs was conducted to investigate the plasma pharmacokinetics, tissue distribution, and accumulation of the spiro-oxindole compound of the invention following 21 days of repeated dermal dosing, as described in more detail below in the Biological Examples. Overall, low systemic exposure was observed (mean maximum observed concentration [$C_{max}$]=11.7 ng/mL) with an apparent steady state achieved between Days 14 and 21. Relatively low concentrations of the spiro-oxindole compound of the invention were found in the tissues in which the spiro-oxindole compound of the invention was measured except for the skin at the drug administration site. Furthermore, in a domestic pig study, following topical administration of pharmaceutical compositions of the invention to a joint, as described in more detail below in the Biological Examples, micromolar concentrations of the spiro-oxindole compound of the invention were detected, surprisingly, in the synovial membrane tissue of the joint, despite very low (i.e., nanomolar) plasma concentrations. The results of this study were surprising in that they demonstrated that the spiro-oxindole compound of the invention, when topically administered, has an excellent ability to penetrate into the target joint tissue, particularly the synovial membrane of the joint, at concentration levels higher than expected with minimal or negligible systemic exposure after administration.

Without being bound by theory, the fact that the spiro-oxindole compound of the invention was previously found to be highly protein bound in human, monkey, dog, minipig, rat and mouse plasma at the 0.1, 1.0 and 10 μM concentrations (97.4% to 99.8%) may explain its ability to penetrate into joint tissue, particularly the synovial membrane of the joint, at concentration levels higher than expected with minimal or negligible systemic exposure.

As a topical sodium channel blocker, the spiro-oxindole compound may have potent local effects in terms of treating postherpetic neuralgia, like the nonselective sodium channel blocker lidocaine. Unlike lidocaine, the spiro-oxindole compounds has been designed to selectively block activity in the $Na_V1.7$ channel, which is believed to be the most important sodium channel contributing to spontaneous and hyperactive discharges emanating from peripheral nociceptive neurons. As noted above, nonclinical studies have demonstrated that the spiro-oxindole compounds has efficacy in several classical neuropathic pain models, with comparable efficacy to gabapentin in the chronic constriction injury (CCI) model and superior efficacy to 5% lidocaine in a topical streptozotocin-induced diabetic neuropathic pain model.

Topical formulations comprising the spiro-oxindole compound have been studied in a 2-period crossover trial (each period lasting 3 weeks) in 70 postherpetic neuralgia patients who received one or more doses of the compositions as described in more detail below in the Biological Examples. Although the trial did not meet the primary endpoint (change in mean daily pain score during the last week compared to baseline as measured by the Likert Numeric Rating Scale (NRS)), a significantly larger percentage of patients with 50% reduction in pain were seen during the treatment period in the efficacy evaluable and per protocol (PP) analysis groups. A further clinical trial, designed to further evaluate the efficacy of pharmaceutical compositions of the spiro-oxindole compound in treating postherpetic neuralgia in a larger parallel-group study design, is described in more detail below in the Biological Examples.

A topical formulation of the spiro-oxindole compound of the invention has also been tested in a clinical study for erythromelalgia and was well tolerated by the patients.

Methods of the Invention

The methods of the invention are directed to the administration, preferably periodic administration, of a topical pharmaceutical composition of the invention comprising one or more excipients and a therapeutically effect amount of the spiro-oxindole compound to a mammal, preferably a human, as needed to reduce the severity of postherpetic neuralgia and/or to alleviate postherpetic neuralgia with minimal or negligible systemic exposure.

The topical pharmaceutical compositions of the invention may be administered as one-time single dose. Preferably, the topical pharmaceutical compositions of the invention are periodically administered. Typically, a periodic administration of a topical pharmaceutical composition of the invention will include an initial application of a topical pharmaceutical composition of the invention followed by a pre-determined time period and then the topical pharmaceutical composition of the invention is applied a second time to the same area and then followed by the same pre-determined time period and so forth for a specified duration of time. The pre-determined time period can be from about 4 hours to about 24 hours. In general, a topical pharmaceutical composition utilized in the methods of the invention is periodically administered to a mammal, preferably a human, having postherpetic neuralgia to the affected skin area once (qd), twice (bid), three (tid) or four (qid) times a day as needed to reduce the severity of the postherpetic neuralgia and/or to alleviate the postherpetic neuralgia. In one embodiment, a pharmaceutical composition of the invention is periodically administered once a day (every 24 hours) as needed (i.e., an effective amount of the pharmaceutical composition is topically applied to the affected skin area when postherpetic neuralgia is present). In another embodiment, the pharmaceutical composition is topically administered twice a day (every 12 hours) as needed. In another embodiment, the pharmaceutical composition is topically administered three times a day (every 8 hours) as needed. In another embodiment, the pharmaceutical composition is topically administered four times a day (every 6 hours) as needed. Preferably, the pharmaceutical composition is topically administered once or twice a day.

The specified duration of time for the periodic administration of a topical pharmaceutical composition of the invention is intended to be as long as needed to alleviate or substantially relieve the pain. Preferably, the duration of the periodic administration of a topical pharmaceutical compositions of the invention is from about 1 week to about 6 months, more preferably from about 1 month to 4 months, even more preferably about 3 months.

In general, the dose volume of a pharmaceutical composition utilized in the methods of the invention which is topically administered to the affected skin area of the mammal, preferably a human, is from about 1.0 $\mu L/cm^2$ to about 9.0 $\mu L/cm^2$, preferably from about 1.0 $\mu L/cm^2$ to about 4.0 $\mu L/cm^2$ of skin, more preferably about 3.0 $\mu L/cm^2$.

The therapeutically effective amount of each dose of a topical pharmaceutical composition of the invention is from about 500 mg to about 2000 mg, preferably from about 500 mg to about 1500 mg, more preferably from about 750 mg to about 1200 mg, most preferably about 1200 mg per each administration to the affected skin area.

The therapeutically effective amount of the spiro-oxindole compound in each dose of a topical pharmaceutical composition of the invention is from about 10 mg to about 160 mg, preferably about 24 mg in a 2% pharmaceutical composition of the invention at 3.0 $\mu L/cm^2$ dose volume, 48 mg in a 4% pharmaceutical composition of the invention at 3.0 $\mu L/cm^2$ dose volume, or 96 mg in a 8% pharmaceutical composition of the invention at 3.0 $\mu L/cm^2$ dose volume.

Topical administration of a pharmaceutical composition of the invention can be effected by any method commonly known to those skilled in the art. These methods include, but are not limited to, incorporation of a pharmaceutical composition of the invention into foams, creams, gels, ointments, liniments, transdermal patches or other topical formulations and delivery systems.

Topical administration of a pharmaceutical composition of the invention may be performed by a medical professional or by the patient. In certain embodiments, for maximum effectiveness and increased absorption, the affected skin area to which the pharmaceutical composition of the invention is to be administered is first cleansed, for example using an astringent, such as a standard commercial antiseptic or alcohol, or water, preferably sterile water. The affected skin area is then allowed to dry, and the pharmaceutical composition of the invention is applied onto the affected skin area and rubbed until all the pharmaceutical composition has been absorbed or no residue remains on the skin.

The recipients of topical administration of a pharmaceutical composition of the invention can be any vertebrate animal, such as mammals. Among mammals, the preferred recipients are mammals of the Orders Primate (including humans, apes and monkeys), Arteriodactyla (including horses, goats, cows, sheep, and pigs), Rodenta (including mice, rats, rabbits, and hamsters), and Carnivora (including cats, and dogs). Among birds, the preferred recipients are turkeys, chickens and other members of the same order. The most preferred recipients are humans.

Embodiments of the Invention

The following embodiments of the Invention are in addition to or inclusive of the embodiments disclosed above.

As noted above in the Summary of the Invention, one aspect of the invention is a method of treating postherpetic neuralgia in a mammal, wherein the method comprises administering, preferably periodically administering, to the affected skin area of the mammal a topical pharmaceutical composition comprising one or more excipients and a therapeutically effective amount of the spiro-oxindole compound described above in the Summary of the Invention.

In one embodiment of this aspect, the method results in minimal or negligible systemic exposure of the spiro-oxindole compound.

In another embodiment of this aspect, the method results in a greater concentration of the spiro-oxindole compound in the affected skin area than the concentration of the spiro-oxindole compound in the plasma of the mammal.

As noted above in the Summary of the Invention, another aspect of the invention is a method of locally treating postherpetic neuralgia in a mammal with a minimal or negligible systemic exposure, wherein the method comprises increasing the concentration of the spiro-oxindole compound described above in the Summary of the Invention to a therapeutically effective amount in the affected skin area in the mammal by administering, preferably periodically administering, to the affected skin area a topical pharmaceutical composition comprising one or more excipients and a therapeutically effective amount of the spiro-oxindole compound.

In one embodiment of both aspects of the invention described above, the pharmaceutical composition comprises 2% to 8% (w/w) of the spiro-oxindole compound.

In one embodiment of both aspects of the invention described above, the pharmaceutical composition comprises 2% to 8% (w/w) of the spiro-oxindole compound; 45% to 55% (w/w) PEG 400; 5% to 15% (w/w) Transcutol® P; 2.5% to 7.5% (w/w) oleyl alcohol; 2.5% to 7.5% (w/w) isopropyl myristate; 0.1% w/w to 7.5% (w/w) stearyl alcohol; 0.05% to 1% (w/w) butylated hydroxytoluene; and 15% to 30% (w/w) PEG 3350.

In one embodiment of both aspects of the invention described above, the pharmaceutical composition comprises 2.0% (w/w) of the spiro-oxindole compound; 52.9% (w/w) PEG 400; 10% (w/w) Transcutol® P; 5% (w/w) oleyl alcohol; 5% (w/w) isopropyl myristate; 5% (w/w) stearyl alcohol; 0.1% (w/w) butylated hydroxytoluene; and 20% (w/w) PEG 3350.

In one embodiment of both aspects of the invention described above, the pharmaceutical composition comprises 4.0% (w/w) of the spiro-oxindole compound; 50.9% (w/w) PEG 400; 10% (w/w) Transcutol® P; 5% (w/w) oleyl alcohol; 5% (w/w) isopropyl myristate; 5% (w/w) stearyl alcohol; 0.1% (w/w) butylated hydroxytoluene; and 20% (w/w) PEG 3350.

In one embodiment of both aspects of the invention described above, the pharmaceutical composition comprises 8.0% (w/w) of the spiro-oxindole compound; 46.9% (w/w) PEG 400; 10% (w/w) Transcutol® P; 5% (w/w) oleyl alcohol; 5% (w/w) isopropyl myristate; 5% (w/w) stearyl alcohol; 0.1% (w/w) butylated hydroxytoluene; and 20% (w/w) PEG 3350.

In one embodiment of both aspects of the invention described above, the periodic administration is once a day, twice a day, three times a day or four times a day.

In one embodiment of both aspects of the invention described above, the periodic administration is twice a day.

In one embodiment of both aspects of the invention described above, the periodic administration is once a day.

In one embodiment of both aspects of the invention described above, the topical pharmaceutical composition is administered to the affected skin area in a dose volume of from about 1.0 µL/cm$^2$ to about 9.0 µL/cm$^2$.

In one embodiment of both aspects of the invention described above, the topical pharmaceutical composition is administered to the affected skin area in a dose volume of from about 1.0 µL/cm$^2$ to about 4.0 µL/cm$^2$.

In one embodiment of both aspects of the invention described above, the topical pharmaceutical composition is administered to the affected skin area in a dose volume of 3.0 µL/cm$^2$ In one embodiment of both aspects of the invention described above, the therapeutically effective amount of a topical pharmaceutical composition of the invention is from about 500 mg to about 2000 mg per each administration, preferably each periodic administration, to the affected skin are.

In one embodiment of both aspects of the invention described above, the therapeutically effective amount of a topical pharmaceutical composition of the invention is about 1200 mg per each administration, preferably each periodic administration, to the affected skin area.

In one embodiment of both aspects of the invention described above, the therapeutically effective amount of the topical pharmaceutical composition of the invention is effective in reducing the severity of the postherpetic neuralgia or alleviating the postherpetic neuralgia.

In one embodiment of both aspects of the invention described above, the mammal is human.

In one embodiment of both aspects of the invention described above, the administration, preferably periodic administration, of the topical pharmaceutical composition is effective in reducing a daily average postherpetic neuralgia intensity or severity in the affected skin area in the human when compared to baseline postherpetic neuralgia intensity or severity.

In one embodiment of both aspects of the invention described above, the administration, preferably periodic administration, of the topical pharmaceutical composition of the invention is effective in reducing the postherpetic intensity or severity as assessed by a Linkert Numeric Rating Scale (NRS) score, a Neuropathic Pain Symptom Inventory (NPSI) score, a Daily Sleep Interference Scale (DSIS) score, a Neuropathic Pain Impact on Quality of Life (NePIQoL) score and/or a Patient Global Impression of Change (PGIC) score.

In one embodiment of both aspects of the invention described above, the administration, preferably periodic administration, of the topical pharmaceutical composition of the invention is effective in reducing the postherpetic neuralgia intensity or severity by 30% when compared to the baseline postherpetic neuralgia intensity or severity.

In one embodiment of both aspects of the invention described above, the topical pharmaceutical composition of the invention is effective in reducing the postherpetic neuralgia intensity or severity by 50% when compared to the baseline postherpetic neuralgia intensity or severity.

Combination Therapy

The methods of the invention may be usefully combined with the administration of one or more other therapeutic agents or as any combination thereof, in the treatment of postherpetic neuralgia. For example, the methods of the invention may be utilized in the treatment of postherpetic neuralgia simultaneously, sequentially or separately in combination with other therapeutic methods for the administration of other agents, including, but not limited to:

opioid analgesics, e.g., morphine, heroin, cocaine, oxymorphine, levorphanol, levallorphan, oxycodone, codeine, dihydrocodeine, propoxyphene, fentanyl, hydrocodone, hydromorphone, meripidine, methadone, buprenorphine, butorphanol, nalbuphine and pentazocine;

opioid analgesics in combination with opioid antagonists, e.g., nalorphine, naloxone, naltrexone and nalmefene;

non-opioid analgesics, e.g., acetaminophen, and salicylates (e.g., aspirin);

nonsteroidal antiinflammatory drugs (NSAIDs), e.g., ibuprofen (Advil®), naproxen, fenoprofen, ketoprofen, diclofenac, diflusinal, etodolac, fenbufen, flufenisal, flurbiprofen, indomethacin, ketorolac, meclofenamic acid, mefenamic acid, meloxicam, nabumetone, nimesulide, nitroflurbiprofen, olsalazine, oxaprozin, phenylbutazone, piroxicam, sulfasalazine, sulindac, tolmetin and zomepirac;

anticonvulsants, e.g., carbamazepine, oxcarbazepine, lamotrigine, gabapentin and pregabalin;

antidepressants such as tricyclic antidepressants, e.g., amitriptyline, clomipramine, despramine, imipramine, duloxetine and nortriptyline;

COX-2 selective inhibitors, e.g., celecoxib, rofecoxib, parecoxib, valdecoxib, deracoxib, etoricoxib, and lumiracoxib;

alpha-adrenergics, e.g., doxazosin, tamsulosin, clonidine, guanfacine, dexmetatomidine, modafinil, and 4-amino-6,7-dimethoxy-2-(5-methanesulfonamido-1,2,3,4-tetrahydroisoquinol-2-yl)-5-(2-pyridyl)quinazoline;

barbiturate sedatives, e.g., amobarbital, aprobarbital, butabarbital, butabital, mephobarbital, metharbital, methohexital, pentobarbital, phenobartital, secobarbital, talbutal, theamylal and thiopental;

tachykinin (NK) antagonist, particularly an NK-3, NK-2 or NK-1 antagonist, e.g., ($\alpha$R, 9R)-7-[3,5-bis(trifluoromethypenzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S);

paracetamol;

metabotropic glutamate receptor (mGluR) antagonists;

local anaesthetics such as mexiletine and lidocaine;

corticosteroids such as dexamethasone;

muscarinic antagonists, e.g., tolterodine, propiverine, tropsium t chloride, darifenacin, solifenacin, temiverine and ipratropium;

cannabinoids;

vanilloid receptor agonists (e.g., resinferatoxin) or antagonists (e.g., capsazepine);

topical agents (e.g., lidocaine, capsacin and resiniferotoxin);

muscle relaxants such as benzodiazepines, baclofen, carisoprodol, chlorzoxazone, cyclobenzaprine, methocarbamol and orphrenadine;

anti-histamines or H1 antagonists;

NMDA receptor antagonists;

Phosphodiesterase V inhibitors;

Tramadol®;

cholinergic (nicotinc) analgesics;

alpha-2-delta ligands;

prostaglandin E2 subtype antagonists;

leukotriene B4 antagonists; and 5-lipoxygenase inhibitors.

The one or other therapeutic agents utilized in the combination therapy of the invention may be administered to the mammal, preferably a human, by any route known to one skilled in the art, e.g., orally, topically, peripherally, intravenously, nasally, etc. and in any form.

A method of the invention may therefore be utilized in treating postherpetic neuralgia in a mammal by administering, preferably periodically administering, a topical pharmaceutical composition of the invention as defined above in the Summary of the Invention and one or more therapeutic agents. Preferably, the one or other therapeutic agent is a non-opioid analgesics, such as acetaminophen (e.g., TYLENOL®) and salicylates (e.g., aspirin).

Kits for the Methods of the Invention

The present invention also provides kits (i.e., packages) for using the methods of the invention. The kits contain a pharmaceutical composition of the invention and instructions for the use of the pharmaceutical composition for treating postherpetic neuralgia. Preferably, a commercial kit will contain one or more unit doses of the pharmaceutical composition of the invention. It will be evident to those of ordinary skill in the art that any such composition which is light and/or air sensitive may require additional special packaging and/or instructions. For example, packaging may be used which is opaque to light, and/or sealed from contact with ambient air.

The present invention may be even better understood by reference to the Biological Examples which follow, but those skilled in the art will readily appreciate that the specific studies detailed are only illustrative of the invention as described more fully in the claims which follow thereafter.

Biological Example 1

Absorption, Distribution, Metabolism and Excretion Study in the Minipig after Repeated Daily Dermal Dosing of Pharmaceutical Composition of the Invention The study was carried out on minipigs to obtain information on plasma pharmacokinetics, tissue distribution and accumulation, excretion and metabolic profile of the spiro-oxindole compound after daily dermal administration of a pharmaceutical composition of the invention for 20 consecutive days followed by a single dose of [$^{14}$C]-spiro-oxindole compound Day 21.

The animals also received an intravenous dose of midazolam on Day 0 and again on Day 20 and blood samples were collected for analysis of plasma midazolam concentrations for investigation of CYP3A4 induction or inhibition.

Concentrations of radioactivity were measured in plasma, tissues and excreta by liquid scintillation analysis, concentrations of unchanged spiro-oxindole compound in plasma and selected tissues were determined by an LC-MS/MS bioanalytical method. Attempts to separate radioactive components present in plasma, liver and excreta using HPLC with radioactivity detection were unsuccessful due to low radioactivity levels in these samples.

Male Göttingen minipigs were used for this study to best complement previous preclinical studies performed with the spiro-oxindole compound. The minipig is considered a suitable species for this study.

Objective of the Study

This study was carried out to obtain information during a 20-day period of repeated dermal administration of a pharmaceutical composition of the invention on the achieved concentrations of the spiro-oxindole compound in plasma (to indicate systemic accumulation), and after a final dermal dose (Day 21) of [$^{14}$C]-spiro-oxindole compound on (i) the time-course of plasma radioactivity and spiro-oxindole compound concentrations, (ii) the distribution of radioactivity in body tissues, including distribution into skin layers and of unchanged drug in liver, heart, fat and skin, (iii) the rates and routes of excretion of radioactivity, (iv) the metabolite profiles in plasma, urine, bile, faeces and selected tissues, (v) the chemical nature of metabolites. The animals also received an intravenous dose of midazolam on Day 0 and again on Day 20 and blood samples were collected for analysis of plasma midazolam concentrations.

Study Design

Midazolam was administered on Days 0 and 20 to 3 male minipigs by bolus intravenous injection at a dose level 0.5 mg/kg. On Day 1, a 8% test pharmaceutical composition of the invention was administered topically as an ointment to a clean shaven area of 209-259 cm$^2$ (6% of total body surface area) on the back of the male minipigs at a dose level of about 70 mg ointment/kg. The 8% test pharmaceutical composition comprised the following:

8% Test Pharmaceutical Composition 8.0% (w/w) of the spiro-oxindole compound (active ingredient);

46.9% (w/w) PEG 400 (solvent and ointment base);

10% (w/w) Transcutol® P (penetration enhancing agent);

5% (w/w) oleyl alcohol (penetration enhancing agent);

5% (w/w) isopropyl myristate (penetration enhancing agent);

5% (w/w) stearyl alcohol (ointment stiffening agent);

0.1% (w/w) butylated hydroxytoluene (antioxidant); and

20% (w/w) PEG 3350 (ointment base).

Administration of the 8% test pharmaceutical composition of the invention was repeated for a further 19 days and on Day 21 [$^{14}$C]-spiro-oxindole composition was administered topically as an ointment for a single dose at a dose level of ca 70 mg spiro-oxindole compound equivalents ointment/kg onto the same dose site area of skin. The [$^{14}$C]-spiro-oxindole composition was prepared as follows:

A suitable aliquot of [$^{14}$C]-spiro-oxindole ethanol solution (0.3 mL) was transferred to a weighed amount of non-radiolabelled 8% test pharmaceutical composition ointment (2.2 g). The volume of ethanol added was ca 14% of the total volume to give a target concentration of 8% spiro-oxindole compound/g ointment. The dosing solution was continuously mixed with a spatula for approximately 30 minutes prior to determination of radioactivity concentration and weighing the final dose to each animal, and was stored overnight at room temperature Male Gottingen minipigs were used in this study to best complement previous pre-clinical studies performed with the spiro-oxindole compound.

Concentrations of radioactivity were measured in plasma, tissues and excreta by liquid scintillation analysis, concentrations of unchanged drug in plasma and selected tissues were determined by an LC-MS/MS bioanalytical method. Attempts to separate radioactive components using HPLC with radioactivity detection present in plasma, liver and excreta were unsuccessful due to low radioactivity levels in samples submitted for further analysis.

Experimental Procedure

A. Materials

[$^{14}$C]-spiro-oxindole compound (specific activity 55 mCi/mmol≡128 µCi/mg) was supplied as a solution and stored at ca −20° C. in the absence of moisture and light. Non-radiolabelled spiro-oxindole compound was supplied as a solid and stored at room temperature. Non-radiolabelled 8% test pharmaceutical composition of the invention as an ointment was supplied and stored at room temperature. The radiochemical purity of [$^{14}$C]-spiro-oxindole compound was determined by high performance liquid chromatography (HPLC) with on-line radioactivity detection at the study center. As the radiochemical purity of the test substance provided was less then 97%, it was repurified at the study center prior to the start of the study and stored at ca −20° C. in the absence of moisture and light. The radiochemical purity of the repurified batch was 99.2% by HPLC prior to the start of the study.

All other chemicals used in this study were reagent grade or analytical grade, as appropriate, and were obtained from approved commercial suppliers. Purified water was produced on the premises.

B. Animal Management

Three (3) male Ellegaard Gottingen Minipigs having no previous history of any test xenobiotic treatment were obtained for use on this study. The estimated age of these animals was 19 weeks at the time of first administration and their body weights at the time of first administration were approximately 10 kg. After arrival at the test center, the minipigs were subjected to a suitable physical examination to accepted animal husbandry procedures to ensure their suitability for inclusion in the study. The minipigs were randomly allocated individual identification in the form of ear tags and the study schedule number combined with the animal number constituted a unique identification of each animal.

The minipigs were allowed an acclimatization period of approximately 3 weeks prior to treatment with the test substance. During the acclimatization period and for the duration of the study period, the animals were group-housed in indoor pens except during the period of sample collection following intravesical dose administration when they were housed individually in stainless-steel metabolism cages equipped with wire mesh floors and plastic netting below to allow the separate collection of urine from faeces. Whilst housed within the indoor pens, the animals were provided with cereal straw bedding and soiled bedding was changed daily.

The rooms in which the minipigs were housed were well ventilated with regular air changes, and lit using artificial light, which was controlled to provide an alternating 12-hour light/dark cycle. The ambient air temperature in the animal housing unit was in the range of 15-24° C., and the relative humidity between 40% and 70%; both temperature and humidity were continuously monitored and automatically recorded.

During the course of the study, the minipigs were routinely observed for behavioural changes, and any indications of ill health or reaction to treatment. On the day of dosing, the animals were observed immediately after dosing, again within 2 hours of completion of dosing the study group/phase and on at least one other occasion towards the end of the working day. On all other days post-dose, the animals were observed on at least one occasion, i.e., during the initial animal check procedure.

C. Dose Administration

Midazolam doses were administered by bolus intravenous administration at a target dose level of 0.5 mg/kg and were quantified using nominal concentration of midazolam provided and the volume administered to each animal.

On the day prior to the first dermal dose, the dorsum and flanks of each animal were carefully clipped using electric clippers and shaved using an electric rotary head shaver (Phillips). Clipping and shaving was as close as possible to the skin, whilst avoiding damage to the dose site. Photographs were taken to demonstrate the skin integrity on the clipped area. The corners of the treatment area (equivalent to about 6% body surface area, 11 cm×19 cm-12 cm×22 cm) were marked using an indelible pen. The process of hair removal was repeated periodically during the dose administration period as necessary.

Dosages of test formulations were applied with foil and spread using nitrile gloves to form a thin uniform layer to the treatment site. The dose site remained non-occluded during the 20 days of study composition applications (8% test pharmaceutical composition) but was semi-occluded immediately after the radiolabelled dose application on Day-21 using a tubular elastic net bandage secured in place with a dressing retention tape.

The 8% test pharmaceutical composition of the invention application was quantified from the weight of test formulation applied over the treatment area. [$^{14}$C]-spiro-oxindole composition doses were applied in the same manner over the same dose site area as the 8% test pharmaceutical composition and covered with dressings. The radioactive dose administered to each animal was calculated from the weight of radiolabelled composition supplied and the measured radioactivity concentration. Any residual radiolabelled material remaining on the treatment foil was not quantified so was not included in the calculation of dose administered to each animal.

D. Sample Collection

After intravenous administration of midazolam on Day 0, blood samples (ca 1 mL) were collected by venepuncture (not the vein used for dosing) at predose, 2, 30 minutes, and at 1, 2, 4 and 6 hours post dose and delivered into $K_2$EDTA anticoagulant tubes. Midazolam dosing and subsequent blood sampling were repeated on Day 20 (2 hours post dosing with the 8% test pharmaceutical composition of the invention). All midazolam blood samples were centrifuged (ca 2000×'g' for 10 minutes at ca 4° C.) to obtain the plasma which was transferred into clean polypropylene tubes and stored at ca −20° C.; blood cells were discarded.

Immediately prior to application of the $2^{nd}$, $7^{th}$, $14^{th}$ dose of 8% test pharmaceutical composition of the invention and immediately prior to the final dose of [$^{14}$C]-spiro-oxindole composition on Day 21, a blood sample (ca 2 mL) was collected by venepuncture from each minipig and delivered into $K_2$EDTA anticoagulant tubes. The blood was centrifuged (ca 2000×'g' for 10 minutes at ca 4° C.) to obtain the plasma which was transferred into clean polypropylene tubes, divided into two portions and stored at ca −20° C.; blood cells were discarded.

At the following times after the [$^{14}$C]-spiro-oxindole composition dermal application on Day 21: 0.5, 1, 2, 4, 8, 12 and 24 hours, blood (ca 3 mL) was collected by venepuncture from each minipig and delivered into $K_2$EDTA anticoagulant tubes. The blood was centrifuged (ca 2000×'g' for 10 minutes at ca 4° C.) to obtain the plasma which was transferred into clean polypropylene tubes and stored at ca −20° C. pending analysis; blood cells were discarded.

Urine was collected (into containers cooled in solid $CO_2$) from all minipigs overnight prior to dosing the first Midazolam dose and [$^{14}$C]-spiro-oxindole composition dose, and during 0-6 and 6-24 hours postdose. Feces were collected separately overnight prior to dosing and during 0-24 hours after the [$^{14}$C]-spiro-oxindole composition dose. After collection of the final excreta samples, cages were first washed with water (ca 1 Liter) and then methanol (ca 1 Liter), and the washings were retained for radioactivity analysis.

At 24 hours after application of the [$^{14}$C]-spiro-oxindole composition dose, the semi-occlusive dressings were removed and the dose area cleansed with copious volumes of warm dilute soap solution and dabbed dry with the minimum amount of paper medical wipe. All dressings, washings and wipes were retained for radioactivity measurement. The animals were then sacrificed (pentobarbitone overdose), the stratum corneum at the dose site were removed by tape-stripping (10-20 strips) and retained for radioactivity analysis. The dose site was then excised from the carcass and divided into two approximately equal portions. For one portion, the epidermis was separated from the underlying dermis by transferring each skin sample to a foil boat and heating in a waterbath at 60° C. for approximately 20 minutes. The second portion was immediately attached to cork discs with embedding medium and snap frozen in isopentane cooled with liquid nitrogen. These mounted and frozen samples were stored at ca −70° C. until taken for microautoradiography.

The following tissues/organs were removed from the remaining carcass:

| | |
|---|---|
| Adrenal gland | Pituitary |
| Aorta | Prostate |
| Bile (from the gall bladder) | Salivary gland |
| Bone | Sciatic nerve |
| Bone marrow | Synovial membrane (knee joint) |
| Brain | Skin (remote from the dose site) |
| CSF | Skin (from the dose site after washing and tape stripping) |
| Epididymis | |
| Eye | Spinal cord |
| Fat (white) | Spleen |
| Fat (brown) | Testis |
| Heart | Thymus |
| Kidney | Thyroid |
| Lacrimal gland | Urinary bladder |
| Liver | Vena cava |
| Lungs | Stomach wall |
| Lymph nodes | Stomach content |
| Muscle (remote from dose site) | Small intestine wall |
| Muscle (underlying dose site) | Small intestine content |
| Pancreas | Large intestine wall |
| | Large intestine content |

The urinary bladder from each animal was rinsed with saline and the washings discarded. Each section of the gastrointestinal tract wall was washed to remove contents (which were retained for analysis) prior to analysis. Remaining carcasses were discarded.

Results

Concentrations of radioactivity were measured in plasma, tissues and excreta by liquid scintillation analysis, concentrations of unchanged spiro-oxindole compound in plasma and selected tissues were determined by an LC-MS/MS bioanalytical method. Attempts to separate radioactive components present in plasma, liver and excreta using HPLC with radioactivity detection were unsuccessful due to low radioactivity levels in these samples.

The concentration of the spiro-oxindole compound in plasma (in ng/mL) prior to Days 2, 7 and 14 of 20 daily dermal doses of the 8% test pharmaceutical composition of the invention and following 20 daily dermal doses of the 8% test pharmaceutical composition of the invention followed by a single dermal administration of [$^{14}$C]-spiro-oxindole composition ointment (ca 70 mg ointment/kg/day) in male minipigs is shown below in Tables 1 and 2:

TABLE 1

PLASMA COLLECTED AFTER REPEAT ADMINISTRATION OF 8% TEST PHARMACEUTICAL COMPOSITION OF THE INVENTION

| Time | ng/mL | | | | |
|---|---|---|---|---|---|
| | 3M | 4M | 5M | Mean | sd |
| Predose Day 2 | 1.85 | 1.82 | 0.619 | 1.43 | 0.70 |
| Predose Day 7 | 2.89 | 1.32 | 1.28 | 1.83 | 0.92 |
| Predose Day 14 | 11.7 | 2.56 | 3.33 | 5.86 | 5.07 |
| Predose Day 21 | 4.64 | 2.94 | 2.40 | 3.33 | 1.17 |
| 24 h postdose Day 21 (Analogous to predose Day 22) | 12.7 | 3.86 | 1.63 | 6.06 | 5.85 |

TABLE 2

PLASMA COLLECTED AFTER REPEAT ADMINISTRATION OF 8% TEST PHARMACEUTICAL COMPOSITION OINTMENT FOLLOWED BY A SINGLE ADMINISTRATION OF [$^{14}$C]-SPIRO-OXINDOLE COMPOSITION

| Time after administration of [$^{14}$C]-spiro-oxindole composition | ng/mL | | | | |
|---|---|---|---|---|---|
| | 3M | 4M | 5M | Mean | sd |
| 30 min | 4.11 | 1.26 | 1.63 | 2.33 | 1.55 |
| 1 h | 2.64 | 1.67 | 2.55 | 2.29 | 0.54 |
| 2 h | 3.11 | 1.86 | 12.7 | 5.89 | 5.93 |
| 4 h | 4.75 | 2.97 | 4.02 | 3.91 | 0.89 |
| 8 h | 12.4 | 19.6 | 3.15 | 11.7 | 8.3 |
| 12 h | 5.14 | 5.03 | 3.19 | 4.45 | 1.10 |
| 24 h | 12.7 | 3.86 | 1.63 | 6.06 | 5.85 | sd Standard deviation

Concentrations of radioactivity in plasma following the 20 daily dermal does of the 8% test pharmaceutical composition of the invention followed by a single dermal administration of [$^{14}$C]-spiro-oxindole composition (ca 70 mg ointment/kg/day) to the male minipigs is shown below in Table 3:

TABLE 3

CONCENTRATIONS OF RADIOACTIVITY IN PLASMA FOLLOWING 20 DAILY DERMAL DOSES OF 8% TEST PHARMACEUTICAL COMPOSITION FOLLOWED BY A SINGLE DERMAL ADMINISTRATION OF [$^{14}$C]-SPIRO-OXINDOLE COMPOUND COMPOSITION(CA 70 MG OINTMENT/KG/DAY)

| Time | ng equivalents spiro-oxindole compound/mL | | | | |
|---|---|---|---|---|---|
| | 3M | 4M | 5M | Mean | sd |
| Plasma | | | | | |
| Predose | BLQ | BLQ | BLQ | BLQ | — |
| 30 min | BLQ | BLQ | BLQ | BLQ | — |
| 1 h | BLQ | BLQ | BLQ | BLQ | — |
| 2 h | BLQ | BLQ | BLQ | BLQ | — |
| 4 h | BLQ | 7.03 | BLQ | BLQ | — |
| 8 h | 7.82 | 11.7 | 10.3 | 9.94 | 1.96 |
| 12 h | 12.6 | 15.6 | 10.5 | 12.9 | 2.6 |
| 24 h | 17.9 | 22.3 | 15.9 | 18.7 | 3.3 | sd Standard deviation
BLQ Below the limit of quantification (<5.55-7.40 ng equivalents spiro-oxindole compound/mL)

Concentrations of the spiro-oxindole compound in plasma were above the limit of quantification (>0.5 ng/mL) at predose on Day 2 (i.e., approximately 24 hours after a single dermal dose of 8% test pharmaceutical composition of the invention) when they measured a mean of 1.43 ng/mL, then increased steadily until predose on Day 14 to a mean of 5.86 ng/mL. At predose on Day 21, mean spiro-oxindole compound concentrations were 3.33 ng/mL, which were similar to concentrations observed on Day 14, indicating that steady-state was achieved between Days 14 and 21. Following the last dose (on Day 21), mean plasma concentrations of spiro-oxindole compound increased and were maximal at 8 hours post dose, then declined and at 24 hours post dose, mean plasma concentrations were 6.06 mg/mL, which was significantly similar to concentrations observed at predose on Day 21.

Conversely, mean plasma radioactivity concentrations were generally below the limit of quantification until 8 hours after administration of the radiolabelled ointment on Day 21 when they measured 11.7 ng/mL. Thereafter, mean plasma radioactivity concentrations increased until the final sampling time (24 hours post dose).

Following a single dermal application of [$^{14}$C]-spiro-oxindole compound ointment to the male minipigs following 20 daily dermal applications of 8% test pharmaceutical composition of the invention, <1% of the administered dose was excreted during 24 hours post final dose. Approximately 33% of the administered dose was recovered following exhaustive solvent extraction of dose dressings and a further 21% recovered in dose site swabs. The proportions of the dose associated with the dressings and dose site swabs can be considered to consist entirely of unabsorbed drug. Exhaustive solvent extraction of tape strippings used to remove the stratum corneum from each animal yielded another 2% and a further 26% dose was associated with the epidermis and dermis of the excised dose site excised. The mean overall recovery of radioactivity in male minipigs was 82.36% of the administered dose.

Tissue radioactivity concentrations were generally below the limit of quantification (ca 12-25 ng equivalents spiro-oxindole compound/g) in the majority of tissues analysed. Of the tissues with radioactivity concentrations above the limit of quantification, mean radioactivity concentrations (ng equivalents spiro-oxindole compound/g) were maximal in skin from the dose site (25500), gall bladder contents (4870), fatty tissues (273 [abdominal], 100 [brown]), bone marrow (154), muscle underlying the dose site (142) and skin remote from the dose site (111). Concentrations of the spiro-oxindole compound were also measured in selected tissues and were maximal in skin from the dose site (1860 ng/g), white fat (53.8 ng/g), heart (17.5 ng/g) and liver (11.3 ng/g). The corresponding total radioactivity in these tissues were 25500, 273, 18.5 and 74.9 ng equiv spiro-oxindole compound/g, respectively.

Following UPLC analysis of urine and bile, two distinct peaks were observed in urine whilst in bile (gall bladder contents) another two peaks were observed. Radioactivity levels in these samples were too low for accurate quantification or identification but none were consistent with spiro-oxindole compound. Attempts to separate radioactive components using HPLC with radioactivity detection present in liver and excreta were unsuccessful due to low radioactivity levels in these samples.

Results of microautoradiography of skin samples removed from the dose site after the final dermal dose of [$^{14}$C]-spiro-oxindole compound ointment indicated localization of spiro-oxindole compound-related material in the epidermis, dermis and hair follicles. Greatest concentrations were found at the epidermis and dermo-epidermal junction, and at the hair follicles, particularly the hair follicle bulbs.

Overall in this study, low systemic exposure of the spiro-oxindole compound was observed along with relatively low concentration of the spiro-oxindole compound in the tissues examined except for the skin from the dose site.

Biological Example 2

Joint Penetration and Tissue Distribution Study in Domestic Pig Following Multiple-Dose Topical Administration of a Pharmaceutical Composition Comprising the Spiro-Oxindole Compound This study was conducted to evaluate the joint penetration, systemic plasma exposure and tissue distribution of the spiro-oxindole compound in domestic pigs following topical administration of a pharmaceutical composition utilized in the methods of the invention. Fifteen female pigs were used in this study with three pigs in each group. Beginning on Day 1, a pharmaceutical composition of the invention was topically applied to the left radiocarpal joint (carpus) and tibiotarsal joint (hock) twice daily (bid) for 17 days (34 applications) for Groups 1-4 and once daily (qd) for 17 days (17 applications) for Group 5. Pre-dose blood samples (prior to morning dosing) was collected on Days 2, 7, 10, 14 and 17. A full pharmacokinetic sampling was performed on Day 17 (post am dosing) at the following time points: 1, 2, 4, 8 and 12 hr. On the day of necropsy, Day 18, blood was collected prior to euthanasia, each pig was humanely euthanized and dorsal skin and muscle, liver, kidney, heart, lung, brain, intestine, fat, ovaries, urinary bladder, sciatic nerve, and skin, muscle, synovial membrane, and synovial fluid from all 4 joints (2 treated, left carpus and hock, and 2 untreated, right carpus and hock) was collected.

Dose

Doses were calculated by measuring the joint circumference and joint width (to include ~2 cm above and below the joint) to calculate the total surface area for each individual dose. Group 1 received a 2% pharmaceutical composition of the invention and the dose volume for Group 1 was calculated using the total surface area and the designated dose volume of 3 µL/cm². The total dose volume was then converted from µL to mL to estimate the dose weight in grams, based on the composition density of 1 g/cm³. Following is an example (not actual measurements) of calculating the dose:

| Joint | Total Dose width (cm)* | Joint circumference (cm) | Total Surface Area (cm²)** | Dose (µL/cm²) | Dose Volume (µL) | Dose Volume (mL) | Dose Weight (gm)*** |
|---|---|---|---|---|---|---|---|
| Left carpus | 8.0 | 15 | 120.0 | 3 | 360 | 0.36 | 0.36 |
| Left hock | 9.0 | 19 | 171.0 | 3 | 513 | 0.51 | 0.51 |

*Determined prior to dosing; joint was measured to include ~2 cm above and below the joint and a distance above and below the joint capsules was determined for dose administration.
**Joint width × joint circumference.
***Assuming 1 mL = 1 gm for dosing purposes.

For Groups 2-5, the dose volume was calculated using the total surface area and the designated dose volume of 3 µL/cm² (Groups 2, 3 and 5) or 1 µL/cm² (Group 4). The total dose volume was then converted from µL to mL to estimate the dose length in centimeters of a ribbon of the pharmaceutical composition when squeezed from a glaminate tube onto a metal metric ruler, based on the composition length-weight relationship of 1 cm of pharmaceutical composition being equal to 0.5 g of the composition (diameter of the tube opening was 0.87 cm).

Test Pharmaceutical Compositions and Administration

The hair on the left carpus and hock of each animal was clipped approximately 3 days prior to treatment to allow for any razor burn or skin scrapes to heal before administration of a test pharmaceutical composition. The test pharmaceutical compositions were comprised as follows:

2% Test Pharmaceutical Composition
  2.0% (w/w) of the spiro-oxindole compound (active ingredient);
  52.9% (w/w) PEG 400 (solvent and ointment base);
  10% (w/w) Transcutol® P (penetration enhancing agent);
  5% (w/w) oleyl alcohol (penetration enhancing agent);
  5% (w/w) isopropyl myristate (penetration enhancing agent);
  5% (w/w) stearyl alcohol (ointment stiffening agent);
  0.1% (w/w) butylated hydroxytoluene (antioxidant); and
  20% (w/w) PEG 3350 (ointment base).

4% Test Pharmaceutical Composition
  4.0% (w/w) of the spiro-oxindole compound (active ingredient);
  50.9% (w/w) PEG 400 (solvent and ointment base);
  10% (w/w) Transcutol® P (penetration enhancing agent);
  5% (w/w) oleyl alcohol (penetration enhancing agent);
  5% (w/w) isopropyl myristate (penetration enhancing agent);
  5% (w/w) stearyl alcohol (ointment stiffening agent);
  0.1% (w/w) butylated hydroxytoluene (antioxidant); and
  20% (w/w) PEG 3350 (ointment base).

8% Test Pharmaceutical Composition
  8.0% (w/w) of the spiro-oxindole compound (active ingredient);
  46.9% (w/w) PEG 400 (solvent and ointment base);
  10% (w/w) Transcutol® P (penetration enhancing agent);
  5% (w/w) oleyl alcohol (penetration enhancing agent);
  5% (w/w) isopropyl myristate (penetration enhancing agent);
  5% (w/w) stearyl alcohol (ointment stiffening agent);
  0.1% (w/w) butylated hydroxytoluene (antioxidant); and
  20% (w/w) PEG 3350 (ointment base).

The 2% Test Pharmaceutical Composition was topically administered to the animals of Group 1.
The 4% Test Pharmaceutical Composition was topically administered to the animals of Group 2.
The 8% Test Pharmaceutical Composition was topically administered to the animals of Group 3, Group 4 and Group 5.

The test compositions were topically applied an equal distance above and below the center of the joint, i.e., inter-carpal joint space (carpus) and inter-tarsal joint space (hock) of each animal to allow for complete coverage of the joint, including approximately 2 cm above and below the edges of the joint. The test composition was applied to the entire circumference of the designated area. All animals were dosed using the same distance above and below each joint center for consistency.

The dose volume (μL/cm²) for the test pharmaceutical compositions was 3.0 μL/cm² for Groups 1, 2, 3 and 5 and 1.0 μL/cm² for Group 4.

Pharmacokinetic Samples

Approximately 2 mL of whole blood was collected prior to the morning dose administration on Days 2, 7, 10, 14 and 17. A full pharmacokinetic profile sampling was performed on Day 17 after the morning dose administration at the following time points: 1, 2, 4, 8 and 12 hr. On the day of necropsy, Day 18, blood was collected prior to euthanasia.

Tissue Collection

The following tissue samples were collected after euthanasia:

Dorsal skin and muscle (from the mid-back)

Liver—Left Medial Lobe

Kidney—Right

Heart

Lung—Right diaphragmatic lobe

Brain—Right cerebral hemisphere

Intestine—mid-jejunum

Duodenum (10-15 cm length) from all 6 animals in Groups 1 and 2

Fat

Ovary—Right

Urinary bladder

Sciatic nerve from both legs

Skin, muscle underlying site of administration and synovial membrane of all 4 joints (treated left carpus and hock and untreated right carpus and hock)

Results

The concentration of the spiro-oxindole compound in the synovial membrane of the treated joints of the test animals is shown below in Table 4:

TABLE 4

SPIRO-OXINDOLE COMPOUND CONCENTRATION IN SYNOVIAL MEMBRANE TISSUE

| Group | Untreated Test Animal No. and Joint | ng/g | Treated Test Animal No. and Joint | ng/g |
|---|---|---|---|---|
| G1 | #1 right carpus | 44.47 | #1 left carpus | 105.89 |
|  | #1 right hock | 41.19 | #1 left hock | 54.04 |
|  | #2 right carpus | 70.83 | #2 left carpus | 126.88 |
|  | #2 right hock | 97.22 | #2 left hock | 152.13 |
|  | #3 right carpus | 84.97 | #3 left carpus | 56.86 |
|  | #3 right hock | 33.16 | #3 left hock | 38.86 |
| G2 | #4 right carpus | 114.15 | #4 left carpus | 72.14 |
|  | #4 right hock | 92.75 | #4 left hock | 132.05 |
|  | #5 right carpus | 100.42 | #5 left carpus | 269.82 |
|  | #5 right hock | 69.80 | #5 left hock | 95.93 |
|  | #6 right carpus | 129.30 | #6 left carpus | 183.72 |
|  | #6 right hock | 98.28 | #6 left hock | 131.87 |
| G3 | #7 right carpus | 54.19 | #7 left carpus | 708.62 |
|  | #7 right hock | 82.74 | #7 left hock | 252.46 |
|  | #8 right carpus | 185.83 | #8 left carpus | 737.86 |
|  | #8 right hock | 737.82 | #8 left hock | 576.83 |
|  | #9 right carpus | 130.63 | #9 left carpus | 137.46 |
|  | #9 right hock | 167.55 | #9 left hock | 1917.93 |
| G4 | #10 right carpus | 34.85 | #10 left carpus | 49.99 |
|  | #10 right hock | 26.20 | #10 left hock | 291.56 |
|  | #11 right carpus | 1772.86 | #11 left carpus | 59.22 |
|  | #11 right hock | 0.00 | #11 left hock | 38.32 |
|  | #12 right carpus | 46.92 | #12 left carpus | 159.68 |
|  | #12 right hock | 45.29 | #12 left hock | 3171.10 |
| G5 | #13 right carpus | 11.61 | #13 left carpus | 702.22 |
|  | #13 right hock | 18.69 | #13 left hock | 31.44 |
|  | #14 right carpus | 25.25 | #14 left carpus | 150.00 |
|  | #14 right hock | 37.98 | #14 left hock | 100.00 |
|  | #15 right carpus | 79.58 | #15 left carpus | 35.31 |
|  | #15 right hock | 21.70 | #15 left hock | 55.90 |

The concentration of the spiro-oxindole compound (in ng/mL) in plasma of the test animals is shown below in Table 5:

TABLE 5

SPIRO-OXINDOLE COMPOUND CONCENTRATION IN PLASMA

| Animal Number | Day 2 Before dosing | Day 7 Before dosing | Day 10 Before dosing | Day 14 Before dosing | Day 17 Before dosing | Day 17 1 hour after dosing | Day 17 2 hour after dosing | Day 17 4 hour after dosing | Day 17 8 hour after dosing | Day 17 12 hour after dosing | Day 18 |
|---|---|---|---|---|---|---|---|---|---|---|---|
| #1 | 1.02 | 1.36 | 1.14 | 3.44 | 1.13 | 7.59 | 1.10 | 8.22 | 1.91 | 10.28 | 3.94 |
| #2 | 1.65 | 4.12 | 1.87 | 4.69 | 1.43 | 2.71 | 2.16 | 1.67 | 2.03 | 12.85 | 3.24 |
| #3 | 0.34 | 0.97 | 1.54 | 1.10 | 2.70 | 1.21 | 1.07 | 1.04 | 1.30 | 11.38 | 1.60 |
| #4 | 0.84 | 1.73 | 1.79 | 2.47 | 3.25 | 2.47 | 3.47 | 2.72 | 1.94 | 12.17 | 5.41 |
| #5 | 0.86 | 1.74 | 5.34 | 4.35 | 3.90 | 2.78 | 4.20 | 3.56 | 3.02 | 15.72 | 2.83 |
| #6 | 1.24 | 2.66 | 2.11 | 3.40 | 2.24 | 2.24 | 2.48 | 4.83 | 1.62 | 21.78 | 3.29 |
| #7 | 1.47 | 1.50 | 5.48 | 2.19 | 14.43 | 0.98 | 2.37 | 1.85 | 1.65 | 27.61 | 2.76 |
| #8 | 1.21 | 4.40 | 5.13 | 4.81 | 2.45 | 9.03 | 4.47 | 4.29 | 3.36 | 16.89 | 6.10 |
| #9 | 2.36 | 0.00 | 3.64 | 6.86 | 3.90 | 7.37 | 5.31 | 6.23 | 3.43 | 102.48 | 4.13 |
| #10 | 0.24 | 4.82 | 1.10 | 1.90 | 1.12 | 2.62 | 3.51 | 2.27 | 1.29 | 9.98 | 1.09 |
| #11 | 0.71 | 1.89 | 1.24 | 2.63 | 0.72 | 5.22 | 3.57 | 2.03 | 2.15 | 15.16 | 2.36 |
| #12 | 1.34 | 0.99 | 1.88 | 2.14 | 1.41 | 1.01 | 1.94 | 2.74 | 2.83 | 24.37 | 1.34 |
| #13 | 2.68 | 3.34 | 1.14 | 2.77 | 2.17 | 3.49 | 3.53 | 3.70 | 4.21 | 10.60 | 2.10 |
| #14 | 1.26 | 0.92 | 1.87 | 2.74 | 0.63 | 0.67 | 1.65 | 1.85 | 7.22 | 4.97 | 0.96 |
| #15 | 0.43 | 1.29 | 1.07 | 1.53 | 0.99 | 2.49 | 2.56 | 1.28 | 1.00 | 8.47 | 4.94 |

The concentration of the spiro-oxindole compound (in ng/g) in liver tissue of the test animals is shown in Table 6 below:

TABLE 6

SPIRO-OXINDOLE COMPOUND CONCENTRATION IN LIVER TISSUE

| Group | Animal No. | ng/g |
|---|---|---|
| G1 | #1 | 17.0 |
|  | #2 | 2.2 |
|  | #3 | 14.0 |
| G2 | #4 | 0/0 |
|  | #5 | 49.1 |
|  | #6 | 29.3 |
| G3 | #7 | 47.2 |
|  | #8 | 48.2 |
|  | #9 | 21.6 |
| G4 | #10 | 0.0 |
|  | #11 | 39.1 |
|  | #12 | 13.0 |
| G5 | #13 | 3.6 |
|  | #14 | 25.1 |
|  | #15 | 0.0 |

The above results indicate that periodic administration of the topical pharmaceutical compositions of the invention provided an unexpectedly high concentration of the spiro-oxindole compound in the synovial membrane of the treated joints of the test animals with minimal or negligible systemic exposure of the spiro-oxindole compound to plasma or to liver tissue.

Biological Example 3

A Randomized, Double-Blind, Placebo-Controlled, Two-Period Crossover Study to Evaluate the Safety, Tolerability, Preliminary Efficacy, and Systemic Exposure of the Topical 8% Test Pharmaceutical Composition of the Invention in Subjects with Postherpetic Neuralgia Study Objectives The objectives of this study were to compare the safety and efficacy of a pharmaceutical composition of the invention to that of placebo for the relief of postherpetic neuralgia in subjects with postherpetic neuralgia (PHN) and to evaluate the extent of systemic exposure of the spiro-oxindole compound following topical application of the pharmaceutical composition in subjects with postherpetic neuralgia.

Methodology

This was a randomized, placebo-controlled, 2-period crossover study consisting of an up to 3-week screening/washout period; two 1-week, single-blind, placebo run-in periods; a 1-week inter-treatment washout period; and two 3-week, double-blind treatment periods.

Subjects who qualified for the study after the screening/washout period entered into the first single-blind, placebo run-in period. During the placebo run-in periods, subjects applied placebo ointment twice daily (bid) for 7 days. The area of application was to cover the most painful skin segments up to 400 cm². Subjects recorded their pain score at 4 specific times each day (upon waking, at 12:00 noon±1 hour, at 4:00 p.m.±1 hour, and at 8:00 p.m.±1 hour) and reported these scores using the Medpace ClinTrak Interactive Voice Response System (CTIVRS). The use of any rescue medication (1000 mg acetaminophen every 4 to 6 hours, up to 4000 mg/day) was recorded in the rescue medication diary.

Subjects who reported average daily pain scores on an 11-point Likert Numerical Rating Scale (NRS) for at least 4 days during the first placebo run-in period were eligible for randomization to treatment and entered into Treatment Period 1. At the randomization visit (Visit 3), subjects were randomly assigned (in a 1:1 ratio) to one of the following treatment sequences: investigational product/placebo or placebo/investigational product. Subjects received the first specified treatment during Treatment Period 1 and the second specified treatment during Treatment Period 2.

During each 3-week, double-blind Treatment Period, subjects applied study medication bid to cover the most painful skin segments up to 400 cm². As in the placebo run-in period, subjects continued to record their pain scores at 4 specific times each day and report their scores twice a day using the CTIVRS. The use of any rescue medication was recorded in the rescue medication diary. Subjects were assessed for safety, signs of local irritation, the presence of numbness (decreased sensitization), and the presence of allodynia (pain induced by a gentle brush touch) at the beginning and end of each Treatment Period. In addition, subjects provided a blood sample for pharmacokinetic (PK) analyses at each weekly study visit of the double-blind Treatment Periods and following the week of washout (Visits 7 and 12).

Upon completing Treatment Period 1, subjects began a 1-week washout prior to starting the second period of the crossover study. During the washout, subjects did not apply any study medication (placebo or investigational product), but continued to record pain scores using the CTIVRS. The use of any rescue medication was recorded in the rescue medication diary.

After the washout, subjects entered the second single-blind, placebo run-in period, which was followed by Treatment Period 2. Subjects returned for a follow-up visit 1 week after completing Treatment Period 2.

Duration of Treatment 42 days of randomized treatment (21 days of placebo and 21 days of investigational product) plus 14 days of placebo treatment (a 1-week, placebo run-in period prior to each Treatment Period).

Number of Subjects

Planned: 60 subjects

Screened: 129 subjects

Entered placebo run-in: 109 subjects

Randomized: 70 subjects

Completed: 54 subjects

Discontinued: 16 subjects

Diagnosis and Main Criteria for Inclusion

The population for this study included male and female subjects to 80 years of age with persistent pain for more than 6 months from the appearance of herpes zoster rash that was not located on the face, above the hairline of the scalp, and/or in proximity to mucous membranes.

Investigational Product and Placebo Information

The investigational product was the 8% Test Pharmaceutical Composition in ointment form as disclosed herein. The placebo composition had the same composition as the 8% Test Pharmaceutical Composition except that the spiro-oxindole compound is not present and the amount of PEG400 in the placebo composition is increased by the amount of the spiro-oxindole compound if it were present. The placebo composition was identical in appearance to 8% Test Pharmaceutical Composition ointment.

Treatments

Subjects applied 8% Test Pharmaceutical Composition or placebo composition twice a day (bid) topically to cover the most painful skin segments up to 400 cm². Each subject was assigned to 1 of 4 dose groups based on the size of the affected skin area. Subjects were then provided with an application-area specific dosing card, as shown below in Table 7, which clearly indicated the amount of the treatment composition which was to be measure out and applied on each dosing occasion.

TABLE 7

TREATMENTS ADMINISTERED BY AREA OF APPLICATION

| Area of Application (cm²) | 8% Test Pharmaceutical Composition Dose (mg) | 8% Test Pharmaceutical Composition Dose (mL) | Amount of Spiro-oxindole compound (mg) |
|---|---|---|---|
| ≤100 | 750 | 0.75 | 60 |
| 101 to 200 | 1500 | 1.50 | 120 |
| 201 to 300 | 2250 | 2.25 | 180 |
| 301 to 400 | 3000 | 3.00 | 240 |

Treatments were supplied as a 50 g supply in 60 mL plastic laminate tubes with a tamper-proof seal.

Treatments were provided as single tubes of placebo composition for each single-blind, placebo run-in period and in cartons of 3 tubes containing either the 8% Test Pharmaceutical Composition or the placebo composition for each of the 2 Treatment Periods.

Criteria for Evaluation

The primary efficacy parameter was change in mean daily pain score from baseline, measured on an 11-point Likert Numeric Rating Scale (NRS), between the last week of 8% Test Pharmaceutical Composition treatment and the last week of placebo treatment for each subject.

The secondary efficacy parameters included the following:
1. The change in mean daily pain score, measured on an 11-point Likert NRS, from baseline to the first, second, and third week of the Treatment Period;
2. The proportion of subjects achieving 1-point improvement on the 11-point Likert NRS during 8% Test Pharmaceutical Composition treatment compared to placebo;
3. The proportion of subjects achieving at least 50% improvement in mean daily pain score during 8% Test Pharmaceutical Composition treatment compared to placebo;
4. The proportion of subjects achieving at least 30% improvement in mean daily pain score during 8% Test Pharmaceutical Composition treatment compared to placebo;
5. The proportion of subjects using rescue analgesic medications and the amount and number of doses per day during 8% Test Pharmaceutical Composition treatment compared to placebo;
6. The change in Neuropathic Pain Symptom Inventory (NPSI) score from baseline to the end of 8% Test Pharmaceutical Composition treatment compared to placebo;
7. The changes in allodynia scores of NPSI (Q8, Q9, and Q10) from baseline to the end of 8% Test Pharmaceutical Composition treatment compared to placebo;
8. The Patient Global Impression of Change (PGIC) score from baseline to the end of 8% Test Pharmaceutical Composition treatment compared to placebo;
9. The proportion of subjects withdrawing from the study due to lack of efficacy in the target area during 8% Test Pharmaceutical Composition treatment compared to placebo;
10. The change in Daily Sleep Interference Scale (DSIS) score from baseline to the end of 8% Test Pharmaceutical Composition treatment compared to placebo; and
11. The change in mean daily pain score, measured on an 11-point Likert NRS, from baseline to Week 3 with last observation carried forward (LOCF), adjusted for rescue medication utilization.

Safety assessments included adverse events, clinical laboratory measurements, electrocardiograms (ECGs), vital signs (including body weight), and physical examinations.

Statistical Methods

The primary efficacy variable was the change in mean daily pain score from baseline to the last week (Week 3) of the Treatment Period. Baseline for Treatment Period 1 was the average of the 7 mean daily pain measurements prior to randomization (Visit 3), and baseline for Treatment Period 2 was the average of the 7 mean daily pain measurements prior to Visit 8.

The primary efficacy analysis was based on the Efficacy Evaluable Population. Supportive and exploratory analyses were carried out for the primary efficacy variable based on the Intent-to-Treat and Per-Protocol Populations.

The primary efficacy hypothesis was that the mean change in mean daily pain scores from baseline to the end of the Treatment Period would differ between the 8% Test Pharmaceutical Composition treatment and the placebo treatment. This hypothesis was tested using a mixed effects analysis of covariance (ANCOVA) model with treatment, period, and treatment sequence as fixed effects, subject within treatment sequence as a random effect, and the baseline pain score as a covariate. The least-squares means, standard errors, and the 2-tailed 95% confidence intervals for each treatment group were presented.

The secondary efficacy parameter of change in mean daily pain scores from baseline to Week 1, Week 2, Week 2 with LOCF, Week 3, and over the entire Treatment Period (Weeks 1-3 combined) was analyzed in a similar manner as the primary efficacy variable.

All other efficacy variables were summarized using similar methods as for the primary efficacy variable. Efficacy variables were summarized by area of application (≤100 cm², 101 cm² to 200 cm², 201 cm² to 300 cm², and 301 cm² to 400 cm²). Other subgroup analyses (such as demographic variables, disease duration, concomitant medication, etc.) for efficacy variables were performed, as needed. An additional analysis was performed in which all pain scores collected during weeks when subject study medication utilization was <80% or >125% were excluded.

Blood samples taken at Visits 3 through 12 were assayed for concentration levels of the spiro-oxindole compound using a validated bioanalytical method. These values were summarized for each visit during the Treatment Period in which the subject was treated with the 8% Test Pharmaceutical Composition.

All safety analyses were performed for the safety population. Safety variables were summarized using descriptive statistics for continuous variables and frequency and percentage for categorical variables. No formal hypothesis testing was performed to compare safety parameters.

One interim analysis was performed to assess the adequacy of the sample size. Although differences between treatment groups were not analyzed formally, summaries of the primary efficacy variable were prepared. As a result, the significance level for the final analysis was adjusted to $\alpha=0.049$.

Summary of Results
A. Efficacy and Pharmacokinetic Results:

The planned efficacy analysis of the primary endpoint of change in mean daily pain score, measured on an 11-point Likert NRS, did not result in statistically significant or clinically meaningful differences between the 8% Test Pharmaceutical Composition and the placebo treatments at any time point. However, the planned secondary analyses of the proportions of subjects achieving at least 50% improvement in mean daily pain score demonstrated a statistically significant difference between the 8% Test Pharmaceutical Composition and the placebo treatment. In the Efficacy Evaluable Population, more subjects achieved at least 50% improvement with the 8% Test Pharmaceutical Composition treatment than with the placebo treatment at Week 3 with LOCF ($p=0.0039$). A similar trend was seen in the proportion of subjects achieving at least 30% improvement at Week 3 with LOCF ($p=0.0784$). In addition, the difference between treatments in the proportion of subjects achieving at least 30% improvement overall was statistically significant ($p=0.0213$). Results were similar for the Per-Protocol Population, with the proportions of subjects achieving at least 30% and at least 50% improvement at Week 3 with LOCF achieving statistical significance ($p=0.0490$ and $p=0.0078$, respectively). The differences between treatments in the proportion of subjects achieving 1-point improvement in mean daily pain score were not statistically significant for either population.

In addition, post hoc responder analyses were produced to assess the effect of the Treatment Period on improvement in mean daily pain score. Although there were no clear differences between treatments during Treatment Period 1, subjects receiving the 8% Test Pharmaceutical Composition treatment showed greater improvement in mean daily pain score compared to subjects receiving the placebo treatment during Treatment Period 2. Similarly, during Treatment Period 2, more subjects achieved at least 30% ($p=0.0154$) and at least 50% ($p=0.0122$) improvement in pain score after 3 weeks of the 8% Test Pharmaceutical Composition treatment compared to the placebo treatment.

Overall, there was less rescue medication usage with the 8% Test Pharmaceutical Composition treatment than with the placebo treatment. The mean total number of pills of rescue medication taken was lower with the 8% Test Pharmaceutical Composition treatment compared with the placebo treatment (24.8 pills versus 29.2 pills).

NPSI score analysis showed greater decreases in the overall score with the 8% Test Pharmaceutical Composition treatment than with the placebo treatment, but the difference between treatments was not statistically significant.

Only 1 subject discontinued due to worsening of pain at the site of postherpetic neuralgia.

There were no apparent differences between treatments in change from baseline to Week 3 with LOCF in mean DSIS score and PGIC score. However, results of exploratory subgroup analyses indicated a trend towards more favorable outcomes on the 8% Test Pharmaceutical Composition treatment.

As expected, pharmacokinetics (PK) analyses demonstrated a low systemic exposure with the 8% Test Pharmaceutical Composition and the dosing regimen of the 8% Test Pharmaceutical Composition. Throughout the 8% Test Pharmaceutical Composition treatment, approximately 70% of subjects had concentration levels of the spiro-oxindole compound above the detectable limit, but these levels were significantly lower than those previously shown to mediate a systemic analgesic effect. Low residual plasma concentrations were measured during placebo treatment for some subjects whose first treatment was the 8% Test Pharmaceutical Composition. However, the clinical efficacy data do not indicate that these very low levels interfered with the pain intensity results of the study. The placebo response was minimal for those subjects who were dosed with placebo in Treatment Period 2 (the investigational product/placebo sequence) with only 1 subject demonstrating a 50% or greater improvement and 3 subjects demonstrating a 30% or greater improvement.

B. Safety Results:

The 8% Test Pharmaceutical Composition was safe and well tolerated in subjects with postherpetic neuralgia. The overall incidence of treatment-emergent adverse events (TEAEs) was 50.8% with placebo treatment and 53.2% with 8% Test Pharmaceutical Composition treatment. The overall incidence of study medication-related TEAEs was 30.2% with the placebo treatment and 17.7% with the 8% Test Pharmaceutical Composition treatment. The majority of subjects experienced TEAEs that were considered by the Investigator to be mild in severity. Only 3 subjects (4.4%) experienced at least one severe TEAE (2 subjects (3.2%) during placebo treatment and 1 subject (1.6%) during 8% Test Pharmaceutical Composition treatment).

In general, application site reactions were more common with placebo treatment than with the 8% Test Pharmaceutical Composition treatment, suggesting that the presence of the spiro-oxindole compound in the 8% Test Pharmaceutical Composition may have some local protective or relieving effect.

There were no fatal events reported during the study. Two serious adverse events (SAEs) were reported: an SAE of tooth abscess, which occurred during placebo treatment, and an SAE of worsening coronary artery disease, which occurred during the 8% Test Pharmaceutical Composition treatment. Neither SAE was considered by investigators to be related to study medication. Eight subjects discontinued from the study due to an adverse event: 5 subjects during placebo treatment and 3 subjects during the 8% Test Pharmaceutical Composition treatment. For 7 of these 8 subjects, the adverse events leading to discontinuation were local skin reactions. The eighth subject was withdrawn due to the SAE of worsening coronary artery disease.

The review of changes in chemistry, hematology, urinalysis, ECG, and vital signs parameters indicated no safety concerns.

Conclusions

This clinical study demonstrated that treatment with the 8% Test Pharmaceutical Composition for 3 weeks was safe and well tolerated in subjects with postherpetic neuralgia. No new safety issues were identified in this study compared to the previous study in healthy volunteers. Local application site reactions were the most common adverse events and were more common with placebo treatment than with the 8% Test Pharmaceutical Composition treatment. Pharmacokinetic analyses demonstrated a low systemic exposure of the spiro-oxindole compounds, with low residual levels measured during placebo treatment in some subjects who received the 8% Test Pharmaceutical Composition in Treatment Period 1. The planned responder analyses demonstrated that the 8% Test Pharmaceutical Composition treatment resulted in statistically significant proportions of subjects achieving at least 50% improvement in mean pain score compared to the placebo treatment. However, the primary endpoint of the change in mean pain score from baseline to Week 3 with LOCF failed to show a statistically significant difference between the 8% Test Pharmaceutical Composition treatment and the placebo treatment. A larger, parallel-design study of longer duration targeting a more homogenous group of subjects is to be conducted to further evaluate the efficacy of a topical pharmaceutical composition of the invention in treating postherpetic neuralgia.

Biological Example 4

A Randomized, Double-Blind, Placebo-Controlled Study to Evaluate the Safety and Efficacy of the 4% Test Pharmaceutical Composition and the 8% Test Pharmaceutical Composition of the Invention in Patients with Postherpetic Neuralgia This study is designed to evaluate the efficacy of 4 weeks of topical administration of the 4% Test Pharmaceutical Composition and the 8% Test Pharmaceutical Composition of the invention in ointment form compared with placebo for the relief of postherpetic neuralgia as assessed by the change from baseline to week 4 in the weekly average of the daily average Numeric Rating Scale (NRS) scores.
Nonclinical Studies Nonclinical studies have been completed to characterize the tolerability, toxicity, pharmacokinetics, and efficacy of pharmaceutical compositions comprising the spiro-oxindole compound following dermal application and oral administration.
Pharmacology Studies In vitro electrophysiological studies indicated that the spiro-oxindole compound is a potent $Na_V$ blocker active against several $Na_V$ subtypes, including those associated with pain signaling. The potency of blocking against $Na_V 1.7$ is approximately 220-fold greater for the inactivated state (50% inhibitory concentration [$IC_{50}$]=0.05 μM) compared with the resting state ($IC_{50}$=11.3 μM).

In vivo studies in neuropathic and inflammatory pain models in the rat demonstrated that topical administration of a pharmaceutical composition comprising the spiro-oxindole compound provides analgesic relief superior to current marketed topical therapeutics such as lidocaine and diclofenac. Topical 4% Test Pharmaceutical Composition was compared with lidocaine and diclofenac for relief of mechanical allodynia in the streptozotocin-induced neuropathic pain model in rats. A single application of 4% Test Pharmaceutical Composition significantly increased the paw withdrawal threshold for the treated paw compared with application of the vehicle. At 30 minutes after the dose, the 4% Test Pharmaceutical Composition treatment group showed reversal of mechanical hyperalgesia as assessed by measurement of paw withdrawal threshold for the drug-treated paw, with no significant increase in threshold observed for the diclofenac and lidocaine treatment groups.

In the complete Freund's adjuvant model of inflammatory pain, the topical analgesic effects of the 8% Test Pharmaceutical Composition were obtained at a mean plasma concentration (0.32 ng/mL) that was 120-fold lower than that observed at the minimum effective oral dose of a pharmaceutical composition comprising the spiro-oxindole compound in this model. A dose response was observed, and the dose associated with pain relief ranged from a minimum effective dose of 2% Test Pharmaceutical Composition, with the greatest effect seen at the highest dose tested of 8% Test Pharmaceutical Composition. In the CCI model of neuropathic pain, topical 8% Test Pharmaceutical Composition exhibited a degree of efficacy comparable with 25 mg/kg spiro-oxindole compound by oral administration despite systemic plasma exposure of the spiro-oxindole compound (maximum observed concentration [$C_{max}$] 3.6 ng/mL) being significantly lower (approximately 20-fold) than that of the oral treatment group. Based on these data, the analgesic effect of topical pharmaceutical composition comprising the spiro-oxindole compound in these animal models is considered to be due to a local rather than a systemic drug effect.
Pharmacokinetic Studies A study in minipigs (not conducted according to Good Laboratory Practice) was conducted to investigate the plasma pharmacokinetics, tissue distribution, and accumulation of the spiro-oxindole compound following 21 days of repeated dermal dosing. Overall, low systemic exposure was observed (mean $C_{max}$=15.0 ng/mL) with an apparent steady state achieved between days 14 and 21. Relatively low concentrations of the spiro-oxindole compound were found in the tissues in which the spiro-oxindole compound was measured, except for the skin at the drug administration site.

The spiro-oxindole compound is highly protein bound in rat serum (99.6%) and dog (98.3%) and human (99.4%) plasma. In vitro metabolic stability and profiling of $^{14}$C-spiro-oxindole compound demonstrated that spiro-oxindole compound is more stable in human than in animal hepatocytes: human (80%)>dog (61%)>minipig (18%)≥rat (16%). A total of 8 metabolites were identified in samples (in vitro and in vivo) from rats, dogs, and humans. All metabolites found in humans were also found in the Good Laboratory Practice (GLP) toxicology species, the rat. Following oral administration of spiro-oxindole compound to humans, spiro-oxindole compound and 3 of its metabolites (M1, M5, and M6) were measurable. A similar metabolic profile was observed following topical administration to humans, albeit at much lower plasma concentrations, except metabolite M1 was not detected following human topical administration.

A reaction phenotyping study using recombinant human cytochrome P450 (CYP450) enzymes suggested that CYP450 2C19 (CYP2C19) and 3A4 (CYP3A4) are major contributors to the spiro-oxindole compound metabolism; CYP450 2D6 is likely to play a less extensive role, and CYP450 2C9 has limited or no involvement in the metabolism of the spiro-oxindole compound.

In vitro data showed that the spiro-oxindole compound may inhibit several CYP450 enzymes including CYP3A4 but may also be a strong inducer of CYP3A4 with an activation potency similar to rifampicin, a known inducer of CYP3A4. A drug-drug interaction (DDI) study conducted in dogs with oral administration of the spiro-oxindole compound using intravenous (iv) midazolam as a CYP3A4 substrate revealed no evidence of a DDI at the spiro-oxindole compound plasma concentrations up to 752 ng/mL (i.e., 1.8 μM).
Toxicology Studies and Toxicokinetics Repeat-dose dermal toxicity of a pharmaceutical composition comprising the spiro-oxindole compound was evaluated in minipigs in a 7-day (non-GLP) dermal study and in a 4-week (GLP) dermal study with a 2-week recovery period. In addition, a dose range-finding (DRF) dermal study in minipigs was conducted to aid in dose selection for a 39-week dermal toxicity study in minipigs.

Following 28 days of once-daily dermal application of 4% Test Pharmaceutical Composition and 8% Test Pharmaceutical Composition in ointment form in minipigs over 10% of body surface area (BSA) at dosages of 5, 10, and 30 mg/kg/day, no spiro-oxindole-related systemic toxicity or dermal irritation was observed. However, the vehicle ointment produced in all treatment groups transient, mild to moderate, and occasionally severe dermal irritation that returned to normal during the recovery period. This correlated with minimal epidermal hyperplasia observed microscopically in the treated skin across all groups. Relatively low systemic exposure was observed on day 28. For the highest treatment group (30 mg/kg/day), the $C_{max}$ was 21 and 20 ng/mL for male and female minipigs, respectively, and their corresponding area under the concentration-time curve from 0 to 24 hours ($AUC_{0-24\ h}$) values were 365 and 382 ng·h/mL, respectively.

Following 7 days of dermal application of 8% Test Pharmaceutical Composition 3 times daily over 10% BSA, similar dermal findings attributed to the vehicle ointment were observed, with no signs of systemic toxicity. In the DRF study in minipigs, the local toxicity of the vehicle or the 8% Test Pharmaceutical Composition ointments active were tested following dermal application at several dose volumes (ranging from 6 to 15 µL/cm$^2$), 2 different dosing frequencies (once and twice daily), and 2 different time intervals between daily doses (6 and 10 hours) for 40 to 79 days. Skin irritation was observed in animals dosed with both ointments, suggesting that the erythema was induced by the vehicle. In addition, females were found to be more sensitive than males. Overall, onset and severity of the skin reactions were similar in all dosing regimens regardless of active or vehicle, dose volume, dosing frequency, or dosing interval. Slight to well-defined erythema (grades 1 to 2) first appeared within the first week of treatment (on days 5, 6, or 7) and progressed to moderate/severe erythema (grades 3 to 4) usually about 2 weeks after dosing initiation. The erythema was reversible after a few days of cessation of treatment. When the vehicle ointment was applied in a dose titration manner, the severity of irritation appeared to be reduced and remained at a low grade until the end of treatment (day 47).

The spiro-oxindole compound was not genotoxic in the standard battery of genotoxicity tests (GLP), including a bacterial reverse mutation assay, an in vitro chromosome aberration assay in cultured human lymphocytes, and an in vivo rat bone marrow micronucleus test.

In a GLP fertility and early embryonic development study in rats, no significant effect on mating performance or fertility was observed following oral (gavage) administration of spiro-oxindole compound at 0 (vehicle), 15, 50, and 150 mg/kg/day. The no-observed-adverse-effect level (NOAEL) was determined to be 150 mg/kg/day in both males and females. In a GLP embryo-fetal developmental toxicity study in rats, there was no effect of treatment on embryo-fetal survival or morphological development following oral (gavage) administration of spiro-oxindole at 0 (vehicle), 15, 50, and 150 mg/kg/day. The NOAEL for maternal toxicity was 50 mg/kg/day. At this dose level, the corresponding $C_{max}$ and $AUC_{0-24\ h}$ values were 1435 ng/mL and 17966 ng·h/mL, respectively, on day gestation day (GD) 17. The NOAEL for embryo-fetal toxicity was 150 mg/kg/day. At this dose level, the corresponding $C_{max}$ and $AUC_{0-24\ h}$ values were 3378 ng/mL and 41545 ng·h/mL, respectively, on GD17.

8% Test Pharmaceutical Composition was found to be a mild skin irritant in an acute dermal irritation study in rabbits. However, it was not an irritant in an acute eye irritation study in rabbits. In addition, the spiro-oxindole compound was not a skin sensitizer in a mouse local lymph node assay and did not show phototoxicity potential in either in vitro or in vivo assays.

Clinical Studies

To date, topically administered spiro-oxindole compound has been evaluated in 3 clinical studies: a Phase 1 study in healthy subjects, a Phase 2a study in patients with postherpetic neuralgia, and a Phase 2a study in patients with inherited erythromelalgia (IEM). Eighty-nine subjects (20 healthy subjects, 70 PHN patients, and 7 IEM patients) received multiple applications of 8% Test Pharmaceutical Composition.

Additionally, evaluation of 8% Test Pharmaceutical Composition is currently underway in a Phase 2 study in patients with osteoarthritis (OA) of the knee, and in a Phase 1 dose-escalation study in healthy volunteers. Final data are not yet available from these ongoing studies.

Oral spiro-oxindole compound has been evaluated in 3 clinical studies: a Phase 1 single ascending dose (SAD) and multiple ascending dose (MAD) study, a Phase 2a study in patients with pain following third molar extractions, and a Phase 2a study in patients with IEM.

Clinical Pharmacology Studies

Topical administration of the spiro-oxindole compound results in minimal to negligible systemic exposure to the spiro-oxindole compound. The plasma concentrations of the spiro-oxindole compound disclosed in this paragraph are maximum individual (not group mean) values. 8% Test Pharmaceutical Composition was administered to 20 healthy subjects for 21 days in a Phase 1 study in which 8% Test Pharmaceutical Composition was shown to be safe and well tolerated with low plasma exposure (highest observed plasma spiro-oxindole concentrations <1 ng/mL). In a Phase 2a study conducted in 70 patients with postherpetic neuralgia, the patients were treated with 8% Test Pharmaceutical Composition for 21 days, and in a Phase 2a study conducted in 8 patients with IEM, 7 patients were treated with 8% Test Pharmaceutical Composition for 14 or 21 days. The amount of drug applied was calculated based on the patient's BSA and a pre-determined fixed-dose volume. The highest plasma spiro-oxindole concentration observed in any patient was approximately 14 ng/mL.

The highest (maximum individual) $C_{max}$ values observed in the 8% Test Pharmaceutical Composition studies were 100-fold lower than the mean $C_{max}$ at the oral maximum tolerated dose (MTD) for a single dose of the spiro-oxindole compound.

Known and Potential Risks and Benefits to Human Subjects

Following topical administration, no observed CNS adverse events were considered related to 8% Test Pharmaceutical Composition treatment by the investigator. Similarly, with the exception of 1 case of worsening coronary artery disease assessed as unrelated to study drug treatment, no significant ECG findings or cardiac arrhythmias were observed in studies of topical 8% Test Pharmaceutical Composition.

In nonclinical dermal toxicology studies performed in minipigs, skin irritation was seen frequently in animals dosed either with a spiro-oxindole compound pharmaceutical composition or vehicle ointment, most often within the first week of dosing. The skin reactions are predominantly erythema and appear to be due to the ointment vehicle itself. In prior clinical studies, however, local reactions at the site of topical application of a spiro-oxindole compound pharmaceutical composition or matching placebo were seen infrequently. These reactions usually consisted of erythema or skin dryness with scaling of skin, were generally mild to moderate, and were approximately the same in frequency and severity for patients treated with either the spiro-oxindole compound pharmaceutical composition or placebo. Although the skin reactions may appear within a couple of days of exposure, they more often occur after a delay of 2 to 3 weeks and resolve soon after cessation of dosing. Worsening skin reactions should be monitored closely.

Due to low systemic exposure following topical administration of 8% Test Pharmaceutical Composition in humans, the DDI risk due to effects on CYP450 enzymes is thought to be low following topical administration. In vitro data using human liver microsomes have shown that the spiro-oxindole compound is an inhibitor of several CYP450 enzymes. However, the compound is also highly bound to constituents in human plasma, so distribution into hepatocytes may be hindered, reducing the inhibition potential. In vitro data using human cryopreserved hepatocytes have also shown that the spiro-oxindole compound metabolite (M3) is an inhibitor of CYP3A4 and CYP2C19. Therefore, certain medications that undergo major metabolism by CYP3A4 and CYP2C19 are excluded as concomitant medications during this study.

In summary, topically administered pharmaceutical compositions comprising the spiro-oxindole compound showed a generally favorable safety profile in nonclinical and clinical studies. Overall, the data for both oral and topically administered pharmaceutical compositions comprising the spiro-oxindole compound support the continued evaluation of topical pharmaceutical compositions comprising the spiro-oxindole compound in clinical studies conducted in patients with chronic pain.

Selection of Drugs and Dosages

The dosage regimens selected for this study are the 4% Test Pharmaceutical Composition and the 8% Test Pharmaceutical Composition, both in ointment form and each administered twice daily.

The selected dosage regimens are based on results from animal pharmacology studies, safety information from previous toxicology and clinical studies, and clinical efficacy previously observed with topical pharmaceutical compositions comprising the spiro-oxindole compound.

Given that the planned dosage regimens in this study are similar or lower than those employed previously in the previous postherpetic neuralgia and IEM studies, and the amount applied per surface area is less than that used in previous studies (3 µL/cm$^2$ in this study compared with 7.5 and 4 µL/cm$^2$ in the previous postherpetic neuralgia and EM studies, respectively), the safety profile is anticipated to be similar to that observed previously in the postherpetic neuralgia and EM studies. In addition, signals of efficacy were observed in both the postherpetic neuralgia and EM studies in which 8% Test Pharmaceutical Composition was applied twice daily. Therefore, it is reasonable to include the 8% Test Pharmaceutical Composition dose as a high dose in this proof-of-concept study in postherpetic neuralgia.

Population to be Studied

The study population will comprise approximately 330 patients (men and women) 18 years of age or older and with chronic postherpetic neuralgia. Approximately 330 patients (110 per treatment group) will be randomly assigned to 4% Test Pharmaceutical Composition, 4% Test Pharmaceutical Composition, or placebo to ensure that approximately 88 patients per group complete the treatment period, i.e., have the week 4 visit (visit 5, day 29).

Patients must have chronic postherpetic neuralgia according to the definition of pain present for more than 6 months and less than 6 years after onset of herpes zoster skin rash affecting a single dermatome. Patients with more than 1 involved dermatome may also be included, provided the affected dermatomes are contiguous. The patient's average daily pain must be at least 4 on the 11-point NRS at screening and during the baseline pain assessment interval (days −7 to −1) immediately before study randomization. Patients with postherpetic neuralgia involving trigeminal dermatomes are excluded from the study.

Purpose of the Study

This is a Phase 2, multicenter, randomized, double-blind, parallel-group, placebo-controlled study to evaluate the safety and efficacy of 4% Test Pharmaceutical Composition and 8% Test Pharmaceutical Composition compared with placebo ointment applied topically and twice daily to the area of postherpetic neuralgia pain for 4 weeks in patients with postherpetic neuralgia.

Primary Objective

The primary objective of this study is to evaluate the efficacy of 4 weeks of topical administration of 4% Test Pharmaceutical Composition and 8% Test Pharmaceutical Composition of the invention compared with placebo for the relief of pain due to postherpetic neuralgia, as assessed by the change from baseline to week 4 in the weekly average of the daily average NRS scores. The daily average NRS score is the average of the 2 NRS scores (recorded in the morning and in the evening) of average pain, defined as the patient-reported average pain intensity over the prior 12 hours.

Secondary Objectives

The secondary objectives of the study are as follows:

1. to evaluate the efficacy of topical 4% Test Pharmaceutical Composition and 8% Test Pharmaceutical Composition compared with placebo by examining the following:
   a. change from baseline to week 4 in the weekly average of the average pain score recorded in the evening
   b. change from baseline to week 4 in the weekly average of the average pain score recorded in the morning
   c. change from baseline to week 4 in the weekly average of the worst pain score recorded in the evening (worst pain is defined as the patient-reported worst pain intensity over the prior 24 hours)
   d. percentage of patients with ≥30% improvement from baseline in the weekly average of the daily average NRS scores at week 4
   e. percentage of patients with ≥50% improvement from baseline in the weekly average of the daily average NRS scores at week 4
   f. change from baseline (randomization visit) to weeks 2 and 4 in the Neuropathic Pain Symptom Inventory (NPSI) score
   g. change from baseline (randomization visit) to week 4 in the Neuropathic Pain Impact on Quality of Life (NePIQoL) score
   h. patients' global assessment of treatment, as measured by the Patient Global Impression of Change (PGIC) scores, at weeks 2 and 4
   i. change from baseline (randomization visit) in the Daily Sleep Interference Scale (DSIS) at weeks 2 and 4
   j. time to reach ≥30% improvement from baseline in the weekly average of the daily average NRS scores
   k. change from baseline (randomization visit) in maximal intensity of patients' brush-evoked allodynia, as measured on 11-point NRS, at weeks 2 and 4
   l. change from baseline (randomization visit) in maximal intensity of patients' punctate-evoked hyperalgesia, as measured on 11-point NRS using a Medipin® (US Neurologicals, LLC/Medipin Ltd), at weeks 2 and 4
2. to characterize the pharmacokinetics of the spiro-oxindole compound in terms of the following:
   a. establishing the dose-exposure relationship of topical 4% Test Pharmaceutical Composition and 8% Test Pharmaceutical Composition under multiple-dose conditions in patients with postherpetic neuralgia)

b. estimating the apparent clearance (CL/F) and volume of distribution (V/F) of the spiro-oxindole compound by incorporating the concentration data of this study into an enriched spiro-oxindole compound pharmacokinetics database and performing population pharmacokinetic modeling
   c. identifying clinically relevant covariates (e.g., age, body weight, gender, and indication) affecting the pharmacokinetics of the spiro-oxindole compound using the population pharmacokinetics model
3. to evaluate the safety of topical 4% Test Pharmaceutical Composition and 8% Test Pharmaceutical Composition treatment compared with placebo, as assessed by the following at specific time points throughout the study based on the schedule of study procedures and assessments:
   a. occurrence of adverse events throughout the study
   b. clinical safety laboratory (serum chemistry, hematology, and urinalysis) test results
   c. vital signs (heart rate, respiratory rate, body temperature, and blood pressure) measurements
   d. ECG findings
   e. physical examination findings
   f. dermal irritation findings
   g. concomitant medication usage throughout the study Exploratory Objectives The exploratory objectives of the study are to evaluate topical 4% Test Pharmaceutical Composition and 8% Test Pharmaceutical Composition compared with placebo by examining the following:
   1. rescue pain medication usage for postherpetic neuralgia
   2. analyses of primary and secondary efficacy endpoints in patients stratified by their R1150W polymorphism status: homozygous minor allele (positive, AA) and heterozygous (positive, AG) versus homozygous common allele (negative, GG)
   3. analyses of genetic variables may be explored in association with response variables, including efficacy, safety, pharmacokinetics, and/or pain characteristics
   4. correlation between presence of measurable brush-evoked allodynia and treatment effect, as measured by change from baseline in the weekly average NRS score at week 4
   5. correlation between presence of punctuate-evoked hyperalgesia and treatment effect, as measured by change from baseline in the weekly average NRS score at week 4
   6. measurement of intraepidermal nerve fiber density in skin biopsies taken from the area of postherpetic neuralgia pain and correlation with response
   7. expression of the $Na_v1.7$ sodium channel in intraepidermal nerves and keratinocytes in skin biopsies taken from the area of postherpetic neuralgia pain and correlation with response General Design and Study Scheme This is a Phase 2, multicenter, randomized, double-blind, parallel-group, placebo-controlled study to evaluate the safety and efficacy of 4% Test Pharmaceutical Composition and 8% Test Pharmaceutical Composition in ointment form compared with placebo ointment applied topically and twice daily to the area of postherpetic neuralgia pain for 4 weeks (days 1 through 28) in patients with postherpetic neuralgia.

For each patient, there will be a total of 6 visits to the study center and 1 telephone contact as follows:
1. screening period
   a. visit 1: screening (up to 28 days before randomization/first administration of study drug)
   b. washout phone contact (approximately 1 week after visit 1 for screening)
   c. washout interval (if needed) of variable/flexible length during which the patient will discontinue oral analgesic therapy, topical pain therapy, and/or non-pharmacologic therapies before initiation of the baseline period
   d. visit 2: baseline visit (day −10)
   e. baseline pain assessment period (days −7 to −1; baseline pain score [average pain intensity score over this interval] obtained)
2. treatment period
   a. visit 3: randomization (day 1 [this is the day after day −1 and the first day of study drug application])
   b. visit 4: day 15±1, week 2
   c. visit 5: day 29, week 4
3. follow-up period
   visit 6: follow-up (day 57±3) or early termination (ET)

The screening period consists of a screening visit (informed consent and preliminary eligibility assessment are obtained); a washout phone contact during which eligibility based on laboratory test results will be reviewed and, as needed, patients will be given instructions to washout (discontinue) oral analgesic or topical pain therapy; a washout interval (if needed) of variable/flexible length during which appropriate patients will discontinue oral analgesic therapy, topical pain therapy, and/or non-pharmacologic therapies; and a baseline pain assessment interval, when each eligible patient will be given an electronic diary (eDiary) to record pain intensity from days −10 to −1. To allow for training in the use of eDiaries, patients will use eDiaries from day −10, but baseline pain assessment will be defined as the last 7 days prior to randomization, i.e., calculated from the values recorded from days −7 through −1. During the baseline pain assessment interval, rescue medications for postherpetic neuralgia pain will not be allowed. Rescue medication will also not be allowed during the last 7 days of treatment. Starting with the baseline pain assessment interval, patients will use eDiaries to record pain, using an 11-point NRS each morning (0700±2 hours) and evening (1900±2 hours), and any rescue pain medication usage. In addition, 3-mm skin punch biopsies will be taken from the area of postherpetic neuralgia pain and a contralateral homologous site at visit 3 (day 1, randomization).

At visit 3 (day 1, randomization), visit 4 (day 15±1, week 2), and visit 5 (day 29, week 4), the NPSI and the DSIS will be administered, and the results will be recorded. On the same visit days, the results of maximal intensity evoked allodynia and maximal intensity evoked hyperalgesia will be recorded. The NePIQoL will be evaluated at visit 3 (day 1, randomization) and visit 5 (day 29, week 4). The PGIC will be evaluated at visit 4 (day 15±1, week 2) and visit 5 (day 29, week 4). Efficacy measures are not collected at visit 6, except for ET visits.

At visit 1 (screening), the patient will identify the location of his/her most severe allodynia, and this location will be used for assessments at all subsequent visits. If allodynia or hyperalgesia is not present at screening, it will not be tested at subsequent visits. The investigator will establish normal sensation by using a standardized 1-inch foam brush (light pressure just sufficient to bend the tip of the brush) to stroke an area of skin that is unaffected by pain. The region of allodynia will then be mapped by applying brush strokes moving from normal skin toward the painful region. A felt-tip pen will be used to mark the point where sensation changes from normal to painful. This process will be repeated until 8 to 10 points are marked in a radial fashion to define the area of allodynia. The marks will then be connected with a continuous line. To assess the intensity of allodynia, the investigator will use the brush to perform 3 brush strokes within the mapped area of allodynia. The patient will then assess pain intensity using an 11-point NRS to answer the question "Please rate the intensity of pain caused by brushing the area of skin where 0=not painful at all and 10=worst pain possible." The pain will be rated for intensity (using the highest pain rating reported) both at prebrush testing and during application of the brush and recorded; additionally, the difference between the 2 scores will be calculated and recorded.

In addition, at visit 1 (screening), the patient will identify the location of his/her most severe hyperalgesia, and this location will be used for assessments at all subsequent visits. To assess the intensity of punctate hyperalgesia, a Medipin will be applied in 3 successive applications to the area of skin identified at screening. The tip of the Medipin rests upon a flange, and the examiner should apply the pin so that the flange rests upon the skin without indenting it. The patient will then assess the pain intensity using an 11-point NRS to answer the question "Please rate the intensity of pain caused by application of the Medipin where 0=not painful at all and 10=worst pain possible." The highest pain rating will be recorded.

Patients will be provided with acetaminophen (TYLENOL®, McNeil Consumer Healthcare Division of McNEIL-PPC, Inc) as 325-mg tablets in bottles of 100 tablets and allowed to take 1 to 2 tablets per dose every 6 hours, as needed, and up to 6 tablets or 1950 mg per day (over a 24-hour period) for rescue relief of postherpetic neuralgia pain. Rescue medication will be provided at the screening visit. Rescue medication compliance will be checked at all visits until used rescue medication is collected after the baseline pain assessment interval or at randomization for patients not continuing in the study, at visit 5 (day 29, week 4) for patients who complete the treatment period, or at the ET visit for patients who prematurely discontinue study drug.

No other rescue medications will be provided or allowed from the washout phone contact through visit 5 (day 29, week 4) or the ET visit. Patients will not be permitted to use rescue medication during the baseline pain assessment interval (days −10 through −1) and during the final week of treatment (the 7-day period before visit 5). During the washout interval, rescue medication use (dates of use and dose taken) will be recorded as concomitant medication. During the baseline period and the treatment period, rescue medication use will be recorded using the eDiary.

At the randomization visit (visit 3, day 1), eligible patients will be randomly assigned via interactive response technology (IRT) in a 1:1:1 fashion to 1 of 3 treatment groups: 4% Test Pharmaceutical Composition, 8% Test Pharmaceutical Composition or placebo ointment. Randomization will be stratified by test results of the pharmacogenomic sample collected at the screening visit (homozygous minor allele [positive, AA], heterozygous [positive, AG], and homozygous common allele [negative, GG]) for R1150W polymorphism in the SCN9A gene. The patient will be instructed on how to apply the study drug. Under study center staff supervision, the area affected by postherpetic neuralgia pain will be carefully defined by mapping the area of pain, and dosing will be prescribed to fully cover the affected area.

Efficacy assessments of pain NRS, NPSI, NePIQoL, and DSIS scores will be conducted at visit 3 (day 1) to establish baseline measurements. The site staff will apply the first dose of blinded study drug and the patient will record the date/time in the eDiary. Subsequent study drug applications will be performed by the patient at home. (If the affected area is not within reach of application by the patient [such as the posterior thoracic region], the patient's designated caregiver will apply the ointment, but the patient will record the time of application in the eDiary.)

During the 4-week treatment period, patients will apply double-blind study drug to the area of postherpetic neuralgia pain twice daily in the morning (0700±2 hours) and again in the evening (1900±2 hours). The first dose of study drug will be applied at the clinic on day 1 (visit 3). Regardless of the clock time of the first dose application at visit 3, the evening dose for day 1 should be applied at 1900±2 hours. The last dose of study drug will be applied at home on the evening of day 28, which is the day before visit 5. In the event that the patient cannot keep the scheduled appointment on day 29, it is nevertheless important for the patient to stop dosing on the evening of day 28. The morning and evening drug applications will be done after recording the response for the NRS pain score. At the start of the baseline pain assessment interval when the eDiary is provided, the eDiary will be used to record the NRS responses, postherpetic neuralgia rescue medication use, and then, after randomization, the dates/times of study drug administration.

Patients will return to the study center for visit 4 (day 15±1, week 2) and again for visit 5 (day 29, week 4). Routine efficacy evaluations (including pain NRS, NPSI, DSIS, and PGIC scores) and safety assessments will be obtained at visit 4 (day 15±1, week 2) and visit 5 (day 29, week 4).

At visit 4 (day 15±1, week 2), 2 blood samples will be taken from each patient for pharmacokinetics analysis: the first sample within approximately 1 to 4 hours after the dose of study drug in the morning and the second sample approximately 2 hours after collection of the first sample. The date and time of the morning dose and the date and exact time for each of the 2 pharmacokinetics samples will be recorded.

At visit 5 (day 29, week 4), the efficacy evaluation NePIQoL will also be performed, and the eDiary will be collected along with the tubes of study drug and bottles of rescue medication. Patients will be instructed to return to their primary care physician to resume therapy deemed appropriate for their postherpetic neuralgia.

Four weeks after visit 5 (day 29, week 4), the patients who completed the double-blind treatment period will return to the study center for a follow-up (visit 6, day 57±3). Activities will include safety assessments for all patients.

Patients who prematurely discontinue study drug will have an ET visit within 2 weeks after the last study drug administration. During the ET visit, the same activities will be conducted as those administered for follow-up at visit 6, the eDiary and any unused study drug/rescue medication will be collected, and compliance checks will be performed. Any treatment-emergent adverse event or serious adverse event will be monitored at suitable intervals until resolved, stabilized, or returned to baseline; until the patient is referred to the care of a health care professional; or until a determination of a cause unrelated to the study drug or study procedure is made during the study period. For adverse event recording, the study period is defined for each patient as that time period from signature of the Informed Consent Form (ICF) through the end of the follow-up period, day 57 (±3). For patients who prematurely discontinue study drug and do not have a treatment-emergent adverse event or serious adverse event, the ET visit will be the last study visit.

Primary Efficacy Measure and Endpoint

The primary efficacy endpoint for this study is the change from baseline to week 4 in the weekly average of the daily average NRS scores. The daily average NRS score is the average of the 2 NRS scores (recorded in the morning and in the evening) of average pain, defined as the patient-reported average pain intensity over the prior 12 hours.

Secondary Efficacy Measures and Endpoints

The secondary efficacy endpoints for this study are as follows:
1. change from baseline to week 4 in the weekly average of the average pain score recorded in the evening
2. change from baseline to week 4 in the weekly average of the average pain score recorded in the morning
3. change from baseline to week 4 in the weekly average of the worst pain score recorded in the evening (worst pain is defined as the patient-reported worst pain intensity over the prior 24 hours)
4. percentage of patients with ≥30% improvement from baseline in the weekly average of the daily average NRS scores at week 4
5. percentage of patients with ≥50% improvement from baseline in the weekly average of the daily average NRS scores at week 4
6. change from baseline (randomization visit) to weeks 2 and 4 in the NPSI score
7. change from baseline (randomization visit) to week 4 in the NePIQoL score
8. patients' global assessment of treatment, as measured by PGIC scores, at weeks 2 and 4
9. change from baseline (randomization visit) in DSIS scores at weeks 2 and 4
10. time to reach 30% improvement from baseline (randomization visit) in the weekly average of the daily average NRS scores
11. change from baseline to weeks 2 and 4 in maximal intensity of patients' brush-evoked allodynia, as measured on the 11-point NRS
12. change from baseline to weeks 2 and 4 in maximal intensity of patients' punctate-evoked hyperalgesia, as measured on the 11-point NRS using a Medipin Exploratory Efficacy Measures and Endpoints The exploratory efficacy endpoints for this study are as follows:
1. rescue pain medication usage for postherpetic neuralgia
2. analyses of primary and secondary efficacy endpoints with patients stratified by their R1150W polymorphism status: homozygous minor allele (positive, AA) and heterozygous (positive, AG) versus homozygous common allele (negative, GG)
3. analyses of genetic variables may be explored in association with response variables, including efficacy, safety, pharmacokinetics, and/or pain characteristics
4. correlation between presence of measurable brush-evoked allodynia and treatment effect, as measured by change from baseline in the weekly average NRS score at week 4
5. correlation between presence of punctuate-evoked hyperalgesia and treatment effect, as measured by change from baseline in the weekly average NRS score at week 4
6. measurement of intraepidermal nerve fiber density in skin biopsies taken from the area of postherpetic neuralgia pain and correlation with response
7. expression of $Na_v1.7$ in intraepidermal nerves and keratinocytes in skin biopsies taken from the area of postherpetic neuralgia pain and correlation with response Safety Measures and Endpoints The safety of 4% Test Pharmaceutical Composition and 8% Test Pharmaceutical Composition will be assessed throughout the study by evaluating adverse events, clinical safety laboratory test results, vital signs measurements, ECG and physical examination results, dermal irritation, and concomitant medication usage. Skin rashes or skin irritation in the area of ointment application will be evaluated using a dermal irritation scale (modified Draize scale) at day 1 (at 1 hour after application of study drug), week 2, week 4, and week 8 for follow-up.

Tolerability Measures and Endpoints

The tolerability of 4% Test Pharmaceutical Composition and 8% Test Pharmaceutical Composition will be assessed during the study using safety endpoints that also represent patients' experience of treatment, such as skin rashes and skin irritation.

Pharmacokinetic Measures and Endpoints

Two blood samples will be collected from each subject following 2 weeks of treatment with either 4% Test Pharmaceutical Composition or 8% Test Pharmaceutical Composition or matching placebo ointment, to quantitate the concentration of the spiro-oxindole in plasma. Patients will go to the study center after applying study drug at home so that the 2 pharmacokinetic samples can be taken. The first sample will be taken within approximately 1 to 4 hours of the morning dose of study drug and the second sample taken approximately 2 hours after collection of the first sample. The date and time of the morning dose and the date and exact time for each of the 2 pharmacokinetic samples will be recorded. Plasma samples will be analyzed for the spiro-oxindole compound. Population pharmacokinetic parameters, such as CL/F and V/F, following topical administration of the 4% Test Pharmaceutical Composition and 8% Test Pharmaceutical Composition to patients with postherpetic neuralgia will be estimated when the sparse data from this study are combined with enriched pharmacokinetic data from other studies with topical pharmaceutical compositions comprising the spiro-oxindole compound. Clinically relevant covariates affecting the pharmacokinetics of the spiro-oxindole compound will be identified as data permit. These results will be reported separately from the main study results.

Pharmacodynamic Measures and Endpoints

Pharmacodynamic endpoints assessed during the study are the following secondary efficacy endpoints: change from baseline in maximal intensity of patients' brush-evoked allodynia and maximal intensity of punctate-evoked hyperalgesia.

Pharmacogenomic Analyses

The objectives of the pharmacogenomic analyses in this study are as follows:
1. To genotype the underlying R1150W polymorphism in the SCN9A gene so as to stratify patients according to R1150W polymorphism status (homozygous minor allele [positive, AA], heterozygous [positive, AG], and homozygous common allele [negative, GG]) in the randomization
2. To investigate associations between DNA variation (within the SCN9A gene region as well as potentially other regions) and treatment responses to the spiro-oxindole compound, if variability in response measurements is observed and may be attributable to genomic parameters
3. To evaluate the relationship between DNA variation and tolerability and safety features of the spiro-oxindole compound, if adverse events are observed and may be considered attributable to genetic variables
4. To genotype polymorphisms of the CYP3A4 and CYP2C19 genes as potential covariates in the population pharmacokinetic analysis Two blood samples (approximately 10 mL total) for pharmacogenomic analyses will be taken from all patients at the screening visit (visit 1) at approximately the same time as the clinical safety laboratory samples are collected. Patients who refuse to give these blood samples will be excluded from the study. One sample will be analyzed to identify the nucleotide (G or A) underlying the R1150W polymorphism in the SCN9A gene and may identify whether there are any other sequence variants in the SCN9A gene region. All samples will be retained for a maximum of 15 years after completion of the study and may be analyzed for other genetic variations potentially associated with pain signaling or drug response, including efficacy, metabolism, and safety parameters. A pharmacogenomic blood sample may be used to assess the polymorphisms of the CYP3A4 and CYP2C19 genes. Depending on the distribution of allelic variations for CYP3A4 and CYP2C19, these results may be incorporated as covariates in the current or future population pharmacokinetic analyses. Pharmacogenomic results for the R1150W polymorphism will be included as appropriate as part of the analyses of primary and secondary efficacy endpoints stratified by R1150W polymorphism status: homozygous minor allele (positive, AA) and heterozygous (positive, AG) versus homozygous common allele (negative, GG). Exploratory analyses may be reported separately from the main study results.

Randomization and Blinding

This is a randomized, double-blind, placebo-controlled study. All tubes of the study drug will be identical, and the ointments will be indistinguishable. Patients, investigators, and all clinical study center staff will remain blinded to treatment assignment during the study. Eligible patients will be randomly assigned via interactive response technology (IRT) in a 1:1:1 ratio to 4% Test Pharmaceutical Composition, 8% Test Pharmaceutical Composition or placebo ointment. Randomization will be stratified by the R1150W underlying genotype in the SCN9A gene: homozygous minor allele (positive, AA), heterozygous (positive, AG), and homozygous common allele (negative, GG).

All patients will be provided with tubes of blinded study drug ointment (4% Test Pharmaceutical Composition, 8% Test Pharmaceutical Composition or placebo) to be applied twice daily to area of postherpetic neuralgia pain during the 4-week treatment period. Placebo ointment is a vehicle-only ointment with identical excipients, content (other than the active pharmaceutical ingredient), appearance, packaging, and labeling to the active treatments.

Study Drugs and Dosage

The study drug is a double-blind 4% Test Pharmaceutical Composition, 8% Test Pharmaceutical Composition or placebo ointment for topical administration. 4% Test Pharmaceutical Composition, 8% Test Pharmaceutical Composition and matching placebo ointments are unscented, off-white to yellowish, opaque ointments with a smooth texture. The ointments contain the same excipients and differ only in the amount of active pharmaceutical ingredient (the matching placebo ointment contains only the excipients). The study ointments will be supplied to the study centers as 50-g fills in 60-mL plastic laminate tubes with tamper-evident seals. The tubes will be stored at ambient room temperature (15° C. to 25° C.).

Blinded study drug will be given to the patients. Study drug will be applied twice daily to the painful area in the morning (0700±2 hours) and again in the evening (1900±2 hours) from days 1 through 28. Study drug will be applied at approximately 3 µL/cm$^2$ per application. The actual amount (mg of ointment) of study drug per application will be measured (as length of ointment) using one or more dosing cards based upon the area of pain determined at randomization (visit 3, day 1).

Patients will be provided with a laminated instruction sheet, including pictures, that will both describe and illustrate how the ointment is to be spread over the entire area of postherpetic neuralgia pain in a thin layer that fully covers the area. The ointment should be lightly massaged into the skin to cover the entire area of postherpetic neuralgia pain.

The first application of study drug will occur at the study center on the day of the randomization visit (visit 3, day 1). The study coordinator or designated site staff member will apply blinded study drug and will define the amount of ointment to be used for all subsequent treatment applications for that patient. Dosing cards and instructions will be provided on how to measure the appropriate amount of ointment for each application. Caretakers will be provided instructions at the randomization visit on how to apply ointment to areas inaccessible to the study patient.

The patients will apply blinded study drug twice daily (morning [0700±2 hours] and evening [1900±2 hours]) on the target area for 4 weeks from days 1 through 28. On day 1, the morning dose might not be applied at 0700±2 hours because the first dose of study drug will be applied at the randomization visit (visit 3, day 1). Regardless of the clock time of the first dose application at the randomization visit, the evening dose for day 1 should be applied at 1900±2 hours.

Compliance will be assessed by weighing tubes at visit 3 (baseline), visit 4 (day 15±1, week 2), and visit 5 (day 29, week 4), or ET visit. A patient will be considered compliant during the interval between the previous 2 visits if the tube weighs between 70% and 120% of the expected weight.

Duration of Patient Participation

This study will consist of a screening period of up to 4 weeks, including a variable-length washout of oral analgesic therapy or topical pain therapy if needed, a 4-week double-blind treatment period, and a 4-week follow-up period. Patients are expected to participate in this study for about 12 weeks.

Stopping Rules and Discontinuation Criteria

There are no formal rules for early termination of this study. During the conduct of the study, serious adverse events will be reviewed as they are reported from the investigational center to identify safety concerns.

In prior clinical studies with topical pharmaceutical compositions comprising the spiro-oxindole compound, skin irritation was seen in some patients exposed to either the spiro-oxindole compound or the vehicle. These skin reactions included pain, pruritus, exfoliation, rash, and erythema; were nearly all mild to moderate in severity; and showed complete resolution after cessation of dosing. Skin reactions are evaluated using the dermal irritation evaluation (modified Draize scale) at visits 2 (baseline visit), 3 (randomization visit, 1 hour after application of the ointment), 4 (day 15±1, week 2 visit), 5 (day 29, week 4 visit), and 6 (follow-up or ET visit). Good clinical judgment is advised in evaluating skin reactions. In the event that a patient develops progressive or severe skin reaction, the Investigator should carefully evaluate the patient and decide whether or not to stop dosing.

A patient may withdraw participation in the study at any time for any reason (e.g., lack of efficacy, consent withdrawn, or adverse event). The investigator and/or Sponsor can withdraw a patient from the study at any time for any reason.

Also, the Sponsor may terminate the study for any reason and at any time.

Study Procedures

Study procedures and assessments with their timing are summarized in Table 8.

TABLE 8

Study Procedures and Assessments

| | Study period | | | | | | |
|---|---|---|---|---|---|---|---|
| | Screening Period | | Randomization | Double-blind treatment period | | Follow-up/ET | |
| | Visit number | | | | | | |
| | Visit 1 | — | Visit 2 | Visit 3 | Visit 4 | Visit 5 | Visit 6 |
| | Visit day (window)[a] | | | | | | |
| | Day −28[b] Screening visit | Day −21[c] Washout[f] phone contact | Day −10[c,d] Baseline[g] visit | Day 1[d] Day of first dose | Day 15 (±1) Week 2 visit | Day 29[e] (±0) Week 4 visit | Day 57 (±3)/Not applicable |
| Procedures and assessments | | | | | | | Follow-up  ET |
| Informed consent | X | | | | | | |
| Inclusion and exclusion criteria | X | X | X | X[h] | | | |
| Medical history and demography | X | | | | | | |
| Adverse event inquiry | | X | X | X[h] | X | X | X  X |
| Prior/concomitant medications | X[i] | X | X | X[h] | X | X | X  X |
| Start washout of prior neuropathic pain therapy (if needed) | | X | | | | | |
| Clinical laboratory tests (serum chemistry, hematology, and urinalysis) | X | | | X[h] | X | X | X  X |
| Urine drug screen | X | | | X[h] | | X | |
| Vital signs measurements[j] | X | | X | X[h] | X | X | X  X |
| Physical examination | X[k] | | | X[h] | X | X | X[k]  X[k] |
| 12-lead ECG[l] | X | | | X[h] | X | X | X  X |
| Pregnancy test (urine)[m] | X | | | X[h] | X | X | X  X |
| Blood samples for pharmacogenomics assessments | X | | | | | | |
| NPSI | X | | | X[h] | X | X | X |
| DSIS | X | | | X[h] | X | | X |
| NePIQoL | X | | | X[h] | | X | X |
| Measure maximal intensity of brush-evoked allodynia[n] | X | | | X[h] | X | X | X |
| Measure maximal intensity of punctate-evoked hyperalgesia[n] | X | | | X[h] | X | X | X |
| Record average daily pain intensity (NRS) at study site | X | | | | | | |
| Record worst daily pain intensity (NRS) at study site | X | | | | | | |
| Dispense/collect rescue medication (review accountability) | X | | X[o] | | X | X (collect only) | X (collect only) |
| Record rescue pain medication usage for PHN as a concomitant medication (ie, not using eDiary) | | X | | | | | X |
| Provide/review/collect patient eDiary | | | X[p] | X[h,q] | X[q] | X[r] | X[r] |
| Record average daily pain intensity (over the previous 12 hours [NRS]) in the morning and in the evening using eDiary[s] | | | X[t] | X[h,u] | X[v] | X[v] | |
| Skin punch biopsy | | | | X[h,w] | | | |
| Randomization and instructions on application of drug | | | | X[h] | | | |
| Study drug compliance check | | | | X[h,x] | X | X | X |
| Rescue drug compliance check | | X | | X[h] | X | X | X |
| Dispense/collect study drug | | | | X[h] | X (dispense study drug only) | X (collect study drug only) | X (collect if prior to V5) |
| Apply study drug twice daily to area of PHN pain[y] | | | | X[z,aa] | X[bb] | | |
| Dermal irritation evaluation | | | X | X[cc,dd] | X | X | X | X |
| Record date/time of study drug application using eDiary | | | | X[aa,cc] | X[bb] | | X (if prior to V5) |
| Record rescue pain medication usage for PHN via eDiary[ee] | | | X[t] | X[cc] (at home) | X[ff] | X[gg] | X (if prior to V5) |
| Record worst daily pain intensity (NRS) in the evening using eDiary | | | X[t] | X[cc] (at home) | X[hh] | | X (if prior to V5) |

TABLE 8-continued

Study Procedures and Assessments

| | Study period | | | | | | |
|---|---|---|---|---|---|---|---|
| | Screening Period | | Randomization | | Double-blind treatment period | | Follow-up/ET |
| | Visit number | | | | | | |
| | Visit 1 | — | Visit 2 | Visit 3 | Visit 4 | Visit 5 | Visit 6 |
| | Visit day (window)$^a$ | | | | | | |
| Procedures and assessments | Day −28$^b$ Screening visit | Day −21$^c$ Washout$^f$ phone contact | Day −10$^{c,d}$ Baseline$^g$ visit | Day 1$^d$ Day of first dose | Day 15 (±1) Week 2 visit | Day 29$^e$ (±0) Week 4 visit | Day 57 (±3)/Not applicable Follow-up   ET |
| Blood samples (including recording of sampling dates/times) for PK assessments$^{ii}$ | | | | | X$^{jj}$ | | |
| PGIC | | | | | X | X | X |

$^a$There is no day 0 for this study. Day −1 is the day before study day 1. Day 1 is the day of both randomization and the first dose (application) of study drug.
$^b$The screening visit should occur no more than 28 days before randomization; day −28 is the earliest possible day for the screening visit.
$^c$Variable/flexible date, depending on the need for washout and the drug(s) to be washed out.
$^d$The baseline visit (day −10) and the randomization visit (baseline +10; day 1) must be confirmed as weekdays.
$^e$No time window (in days) is permitted for visit 5 (day 29, week 4).
$^f$The washout phone contact (approximately 1 week after the screening visit or day −21 at the earliest) will be the start of the washout interval (day of the phone contact through the day before the baseline visit) during which, if needed, the patient will discontinue medications used to treat PHN pain, including opioids (rescue medications [protocol-specified and provided acetaminophen only] permitted during the washout interval). The duration of the washout interval will vary from patient to patient depending on which (if any) medications need to be discontinued. For patients who do not need to washout medications, the other activities in this phone contact (review of eligibility based on laboratory test results and scheduling the baseline visit) will be performed.
$^g$The baseline visit (day −10) will be the start of the baseline period during which baseline information regarding pain will be collected while the patient refrains from all PHN rescue medications.
$^h$Performed prior to first dose of study drug.
$^i$Includes specific query regarding past use of topical therapy such as the 5% lidocaine patch or capsaicin.
$^j$Includes heart rate, respiration rate, body temperature, and blood pressure.
$^k$Includes body weight (screening and follow-up/ET visits only) and height (screening visit only).
$^l$All ECGs will be taken in triplicate and read by a central reader for the study. The central reader will be blinded (will not know the randomization assignment of the patients).
$^m$Only for women of child-bearing potential.
$^n$For brush or punctate mechanical hyperalgesia. If either is not present at screening, it will not be rechecked on subsequent visits.
$^o$Collect from patients not eligible to continue in the study.
$^p$Provide eDiary to eligible patients and instructions on using it to record daily pain (11-point NRS), date/time of study drug applications, and rescue medication usage.
$^q$Review eDiary and review eDiary data via website. Also, for patients not eligible to be randomly assigned to treatment, collect eDiary at the randomization visit (visit 3, day 1).
$^r$Review eDiary, review eDiary data via website, and collect eDiary.
$^s$The eDiary will be used to record responses to 11-point NRS each morning (0700 ± 2 hours) and each evening (1900 ± 2 hours) before applying the study drug.
$^t$At home after baseline visit until randomization visit.
$^u$At home before dosing and in the evening before dosing.
$^v$At home through the morning of day 29.
$^w$At visit 3 (day 1, randomization), 3-mm skin punch biopsies will be taken from the area of PHN pain and a contralateral homologous site.
$^x$Note that tubes must be weighed at visit 3, to obtain a baseline weight for checking study drug compliance at visit 4 (day 15 ± 1, week 2) and visit 5 (day 29, week 4) or ET visit.
$^y$Patients will apply study drug twice daily in the morning (0700 ± 2 hours) and again in the evening (1900 ± 2 hours). The morning applications should take place after recording the morning (0700 ± 2 hours) responses to the 11-point NRS, and the evening applications should take place after recording the evening (1900 ± 2 hours) responses to the 11-point NRS. On day 1, the morning dose might not be applied at 0700 ± 2 hours because this first dose of study drug will be applied at the randomization visit. Regardless of the clock time of the first dose application at the randomization visit, the evening dose for day 1 should be applied at 1900 ± 2 hours.
$^z$First dose will be applied by study site staff at randomization visit (visit 3, day 1).
$^{aa}$At visit and home on day 1; at home from day 2 onward.
$^{bb}$At home through the evening of day 28.
$^{cc}$Performed after first dose of study drug.
$^{dd}$At the randomization visit, dermal irritation will be assessed 1 hour after application of the study drug.
$^{ee}$Although rescue medication is not allowed during the baseline period and during the 7-day period before the week 4 visit (visit 5) of the treatment period, the eDiary will be used to record rescue medication usage, including usage when it is prohibited per protocol.
$^{ff}$At home on day 2 through the morning of day 29.
$^{gg}$At home on the morning of day 29.
$^{hh}$At home on day 2 through the evening of day 28.
$^{ii}$All patients will have blood samples drawn for pharmacokinetic assessments.
$^{jj}$For visit 4 (day 15 ± 1, week 2), patients will go to the study center after applying study drug at home so that 2 pharmacokinetics samples can be taken, with the first sample taken within approximately 1 to 4 hours of the morning dose of study drug and the second taken approximately 2 hours after collection of the first sample. The date and time of morning dose and the date and exact time for each of the 2 pharmacokinetics samples will be recorded.
DSIS = Daily Sleep Interference Scale; ECG = electrocardiogram; eDiary = electronic diary; ET = early termination; NePIQoL = Neuropathic Pain Impact on Quality of Life questionnaire; NPSI = Neuropathic Pain Symptom Inventory; NRS = Numeric Rating Scale; PGIC = Patient Global Impression of Change; PHN = postherpetic neuralgia; PK = pharmacokinetics; V5 = visit 5.

Screening Visit (Visit 1, Day −28)

The screening visit will be no more than 28 days before randomization/first dose of study drug. A signed and dated informed consent form will be obtained before screening procedures commence.

A patient who is screened and does not meet study entry criteria will not be considered for screening again. However, a patient taking prohibited concomitant medications may be allowed to continue with study procedures if the investigator or designee believes that the patient can discontinue the prohibited medications during the 4-week screening period and remain off the prohibited medications through the week 4 (visit 5, day 29) or the ET visit.

The screening visit (visit 1) will take place ≤28 days before the first dose (application) of study drug scheduled to be given in the clinic at the randomization visit (visit 3) on day 1. The following procedures to determine patient eligibility for the study will be performed at the screening visit:
1. obtain written informed consent before any other study-related procedures are performed
2. review inclusion/exclusion criteria
3. review medical history and demography 4. review prior medication history and concomitant medications
5. perform clinical laboratory tests (serum chemistry, hematology, and urinalysis)
6. perform urine drug screen
7. perform vital signs measurements
8. perform physical examination (including body weight and height)
9. perform 12-lead ECG (all ECGs taken in triplicate)
10. obtain urine pregnancy test (women of child-bearing potential only)
11. measure maximal intensity of brush-evoked allodynia and maximal intensity of punctate-evoked hyperalgesia
12. obtain NRS, NPSI, DSIS, and NePIQoL assessments
13. dispense rescue medication In addition, at visit 1 (screening), the patient will identify the location of his/her most severe hyperalgesia, and this location will be used for assessments at all subsequent visits.

Patients will also be informed of all study restrictions and compliance requirements at visit 1.

Two blood samples will be collected for pharmacogenomic analysis. A patient's refusal to provide the pharmacogenomic blood samples will disqualify the patient from participation in the study.

Washout Phone Contact (Approximately 1 Week After the Screening Visit)

The washout phone contact will be no more than 21 days before randomization/first dose of study drug, since it takes place 1 week after visit 1. During the washout phone contact, study eligibility based on laboratory test results will be reviewed, the initial adverse event inquiry will be performed, rescue medication use (if any) will be reviewed and recorded as concomitant medication, prior/concomitant medications will be reviewed, and as needed, patients will be given instructions to washout (discontinue) oral analgesic therapy, topical pain therapy, or non-pharmacologic therapy.

For patients who do not need medication washout, this phone contact will be used for other activities needed at this point in the study (review of eligibility based on laboratory test results, initial inquiry for adverse events, review and recording of any rescue medication use, review of prior/concomitant medications as needed, and scheduling the baseline visit).

Washout Period (Variable Duration Period Between the Washout Phone Contact and the Baseline Visit)

If needed, a washout period of variable/flexible length will take place, during which the patient will discontinue oral analgesic therapy, topical pain therapy, and/or non-pharmacologic therapies before initiation of the baseline period. The duration of the washout interval will vary from patient to patient, depending on which (if any) medications need to be discontinued.

Patients will be provided with acetaminophen (TYLENOL, McNeil Consumer Healthcare Division of McNEIL-PPC, Inc) as 325-mg tablets in bottles of 100 tablets and allowed to take 1 to 2 tablets per dose every 6 hours, as needed, and up to 6 tablets or 1950 mg per 24-hour day.

No other rescue medications will be provided or allowed from the washout phone contact through visit 5 (day 29, week 4) or the ET visit. During the washout interval, rescue medication use (dates of use and dose taken) will be recorded as concomitant medication.

Baseline Visit (Visit 2, Day −10, Weekday)

All patients who successfully complete the washout period or who did not need the washout period will return to the study center for a baseline visit (visit 2). The baseline visit marks the beginning of the baseline period, and must be confirmed as a weekday upon scheduling. Activities at this visit will include the following:
1. review inclusion/exclusion criteria
2. perform adverse event inquiry
3. review prior/concomitant medications
4. perform vital signs measurement
5. dispense/collect rescue medication (collect rescue medication from patients not eligible to continue in the study), perform accountability, and return unused portion to patients continuing in the study
6. provide eligible patient with an eDiary and instruct patient on its use
7. review rescue drug compliance
8. evaluate area of postherpetic neuralgia pain for dermal irritation A patient who does not meet study entry criteria on the basis of results of baseline assessments and is not randomly assigned to treatment/enrolled in the study will not be considered for screening again.

At the baseline visit, patients should be instructed to:
1. record average daily pain intensity (over the previous 12 hours [NRS]), in the morning and in the evening using eDiary
2. record rescue pain medication usage for postherpetic neuralgia via eDiary (patients will be reminded of the restrictions on rescue medication use during the baseline period, and will be instructed to record any use of rescue medications in the eDiary)
3. after the baseline visit, record worst daily pain intensity (NRS) in the evening using eDiary Randomization Visit (Visit 3, Day 1, Weekday)

Patients who continue to meet the inclusion/exclusion criteria will be assigned a permanent unique randomization number and a treatment number using an IRT. These 2 newly assigned numbers will be entered into the CRF, and study drug will be dispensed.

The randomization visit occurs on the same day as the start of study drug treatment. This visit must be confirmed as a weekday upon scheduling.

At the randomization visit (visit 3, day 1), eligible patients will be randomly assigned via IRT in a 1:1:1 fashion to 1 of 3 treatment groups: 4% Test Pharmaceutical Composition, 8% Test Pharmaceutical Composition or placebo ointment. Randomization will be stratified by test results of the pharmacogenomic sample collected at the screening visit (homozygous minor allele [positive, AA], heterozygous [positive, AG], and homozygous common allele [negative, GG]) for R1150W polymorphism in the SCN9A gene.

The following procedures/assessments will be performed at visit 3 prior to study drug dose:
1. review inclusion/exclusion criteria
2. perform adverse event inquiry
3. review prior/concomitant medications
4. perform clinical laboratory tests (serum chemistry, hematology, and urinalysis)
5. perform urine drug screen
6. perform vital signs measurements
7. perform physical examination
8. perform 12-lead ECG (all ECGs taken in triplicate)
9. obtain urine pregnancy test (women of child-bearing potential only)
10. obtain NPSI, DSIS, and NePIQoL assessments
11. measure maximal intensity of brush-evoked allodynia and maximal intensity of punctate-evoked hyperalgesia
12. review rescue drug compliance, perform accountability, and return unused portion to patient if continuing 13. review eDiary and review eDiary data via website (for patients not eligible to be randomly assigned to treatment, collect eDiary)
14. weigh tube of study drug ointment, to obtain baseline tube weight prior to study drug dispensing for study drug compliance checks at subsequent visits
15. obtain 3-mm skin punch biopsies from the area of postherpetic neuralgia pain and a contralateral homologous site The site of the skin biopsy will be covered with a small circular bandage that will be changed daily and may be removed when healed, typically within a few days.

At visit 3 (day 1), the area affected by postherpetic neuralgia pain will be carefully defined by the investigator and the patient by mapping the area of pain. Dosing of the test ointments will be prescribed to fully cover the affected area. The ointment should be applied to the margin of the biopsy site bandage but not covering the bandage. The following procedures/assessments will be performed at visit 3 immediately prior to or at the time of the first study drug dose:

1. instruct the patient to apply study drug twice daily to area of postherpetic neuralgia pain, with the first dose administered by center staff
2. provide patient with instructions on how to apply study drug
3. dispense study drug
4. record date and time of study drug application using eDiary The following procedures/assessments will be performed at visit 3 after the first study drug dose:

1. evaluate area of postherpetic neuralgia pain for dermal irritation 1 hour after first dose At the randomization visit, patients should be instructed to perform the following procedures in the evening at 1900±2 hours:

1. apply study drug
2. record date/time of study drug application using eDiary
3. record rescue pain medication usage for postherpetic neuralgia via eDiary
4. record worst daily pain intensity (NRS) in the evening using eDiary
5. record average daily pain intensity (over the previous 12 hours [NRS]) in the evening using eDiary Patients should also be instructed to record average daily pain intensity (over the previous 12 hours [NRS]) in the morning at 0700±2 hours using eDiary.

Procedures During Double-Blind Treatment Period (Day 1 Through Day 29 Visit)

The start of study drug treatment occurs on the randomization visit (visit 3, day 1). Study drug treatment continues until the evening of day 28.

Daily Routine

During this treatment period (and after the morning study drug application at the clinic on day 1), patients will self-administer topical study drug (4% Test Pharmaceutical Composition, 8% Test Pharmaceutical Composition or placebo) according to the instructions provided by the study center. Study drug will be applied twice daily (in the morning [0700±2 hours] and again in the evening [1900±2 hours]). The first dose of study drug will be applied at the clinic on day 1 during the randomization visit. Regardless of the clock time of the first dose application at the randomization visit, the evening dose for day 1 should be applied at 1900±2 hours. The last dose of study drug will be applied at home on the evening of day 28. No study drug will be applied on day 29, the day of visit 5 (week 4).

Patients who participate in the study in compliance with the protocol from the screening visit through the week 4 visit (visit 5, day 29) will be considered to have completed the study for statistical purposes.

Week 2 Visit (Visit 4, Day 15 [±1])

On day 15 (±1 day), patients will visit the study center (visit 4) in addition to the normal at-home routine. Activities at this visit will include the following:

1. perform adverse event inquiry
2. review prior/concomitant medications
3. perform clinical laboratory tests (serum chemistry, hematology, and urinalysis)
4. perform vital signs measurements
5. perform physical examination
6. perform 12-lead ECG (all ECGs taken in triplicate)
7. obtain urine pregnancy test (women of child-bearing potential only)
8. obtain NPSI, DSIS, and PGIC assessments
9. evaluate area of postherpetic neuralgia pain for dermal irritation
10. measure maximal intensity of brush-evoked allodynia and maximal intensity of punctate-evoked hyperalgesia
11. dispense/collect rescue medication, perform rescue medication accountability, and return unused portion to patients continuing in the study
12. review patient eDiary and review eDiary data via website
13. review study drug compliance and rescue drug compliance
14. dispense/collect study drug
15. obtain 2 blood samples (with recording of sampling dates/times) for pharmacokinetics assessments (the first sample taken within approximately 1 to 4 hours after morning study drug and the second sample taken approximately 2 hours after collection of the first sample)

At visit 4, patients should be instructed to continue to:

1. record average daily pain intensity (over the previous 12 hours [NRS]) in the morning and in the evening using eDiary
2. apply study drug twice daily to area of postherpetic neuralgia pain
3. record date/time of study drug application using eDiary
4. record rescue pain medication usage for postherpetic neuralgia via eDiary
5. record worst daily pain intensity (NRS) in the evening using eDiary Week 4 Visit (Visit 5, Day 29 [±0])

1. The following procedures/assessments will be performed:
2. perform adverse event inquiry
3. review prior/concomitant medications
4. perform clinical laboratory tests (serum chemistry, hematology, and urinalysis)
5. perform urine drug screen
6. perform vital signs measurements
7. perform physical examination
8. perform 12-lead ECG (all ECGs taken in triplicate)
9. obtain urine pregnancy test (women of child-bearing potential only)
10. obtain NPSI, DSIS, NePIQoL, and PGIC assessments
11. evaluate area of postherpetic neuralgia pain for dermal irritation
12. measure maximal intensity of brush-evoked allodynia and maximal intensity of punctate-evoked hyperalgesia
13. collect rescue medication and review accountability 14. review eDiary and review eDiary data via website, including the following data recorded by the patient at home:
    a. average daily pain intensity (over the previous 12 hours [NRS]) through the morning of day 29
    b. date/time of study drug application through the evening of day 28
    c. rescue pain medication usage for postherpetic neuralgia
    d. worst daily pain intensity (NRS) through the evening of day 28
15. collect eDiary
16. review study drug compliance and rescue drug compliance
17. collect study drug Early Termination Visit For patients who discontinue the study drug prematurely (do not complete the per protocol treatment period), there will be an ET visit as soon as possible after the last study drug administration.

The follow-up visit activities plus eDiary and unused study drug/rescue medication collection (and compliance checks) will be conducted at the ET visit, for ET visits occurring prior to visit 5 (day 29, week 4). An ET visit may also occur after visit 5 but before the day that visit 6 would normally be scheduled, on day 57±3. If adverse events or other safety findings are present at the ET visit, the clinical course of each adverse event will be monitored at suitable intervals until resolved or stabilized or returned to baseline, until the patient is referred to the care of a health care professional, or until a determination of a cause unrelated to the study drug or study procedure is made. Otherwise, the ET visit will be the last study visit for these patients.

Because premature discontinuations of treatment may occur at any time between randomization and the week 4 visit (visit 5, day 29), patients will be permitted to proceed directly from either visit 3 (day 1, randomization), visit 4 (day 15±1, week 2), or visit 5 (day 29, week 4) to the ET visit. For example, a patient who discontinues study drug on day 20 will have visit 4 (day 15±1, week 2) followed by visit 6 (ET) as soon as possible after day 20 with no visit 5 (day 29, week 4) in between.

The following procedures/assessments will be performed at the ET visit:
1. perform adverse event inquiry
2. review prior/concomitant medications
3. review and record rescue medication use (if any) as concomitant medication, not using eDiary
4. perform clinical laboratory tests (serum chemistry, hematology, and urinalysis)
5. perform vital signs measurements
6. perform physical examination (including body weight)
7. perform 12-lead ECG (all ECGs taken in triplicate)
8. obtain urine pregnancy test (women of child-bearing potential only)
9. obtain NPSI, DSIS, NePIQoL, and PGIC assessments
10. evaluate area of postherpetic neuralgia pain for dermal irritation
11. measure maximal intensity of brush-evoked allodynia and maximal intensity of punctate-evoked hyperalgesia
12. collect rescue medication (if prior to visit 5) and review accountability
13. review eDiary and review eDiary data via website, including the following data recorded by the patient the previous evening (if prior to visit 5):
    a. date/time of study drug application
    b. rescue pain medication usage for postherpetic neuralgia
    c. worst daily pain intensity (NRS) in the evening
14. collect eDiary (if prior to visit 5)
15. review study and rescue drug compliance
16. collect study drug (if prior to visit 5)

Follow-Up Period (after the Week 4 Visit)

At the week 4 visit (visit 5, day 29), patients who completed the double-blind treatment period will enter a 4-week follow-up period, during which they will not use study drug. They should be instructed to return to their primary care physician to resume therapy deemed appropriate for their postherpetic neuralgia.

Follow-Up Visit or ET Visit (Visit 6, Day 57 [±3])

At the end of the follow-up period (visit 6, day 57±3), patients will return to the study center for the follow-up visit. This visit will be the final visit of the study. Activities at the follow-up visit will include the following:
1. perform adverse event inquiry
2. review medications taken since previous visit
3. perform clinical laboratory tests (serum chemistry, hematology, and urinalysis)
4. perform vital signs measurements
5. perform physical examination (including body weight)
6. perform 12-lead ECG (all ECGs taken in triplicate)
7. obtain urine pregnancy test (women of child-bearing potential only)
8. evaluate area of postherpetic neuralgia pain for dermal irritation Activities performed at the ET visit only will include the following:
1. obtain NPSI, DSIS, NePIQoL, and PGIC assessments
2. measure maximal intensity of brush-evoked allodynia and maximal intensity of punctate-evoked hyperalgesia
3. collect rescue medication (if prior to visit 5)
4. review and record rescue medication use (if any) as concomitant medication, not using eDiary
5. review eDiary and review eDiary data via website, including the following data recorded by the patient the previous evening (if prior to visit 5):
    a. date/time of study drug application
    b. rescue pain medication usage for postherpetic neuralgia
    c. worst daily pain intensity (NRS) in the evening
6. collect eDiary (if prior to visit 5)
7. review study and rescue drug compliance
8. collect study drug (if prior to visit 5)

Patient Inclusion Criteria

Patients may be included in the study only if they meet all of the following criteria:
1. Patient has chronic postherpetic neuralgia, defined as pain present for more than 6 months and less than 6 years after onset of herpes zoster skin rash affecting a single dermatome. Patients with more than 1 involved dermatome may also be included, provided the affected dermatomes are contiguous.
2. Patient has average daily pain of at least 4 on the 11-point NRS at screening and during the baseline pain assessment interval (days −7 to −1) immediately before randomization.
3. Patient must properly assess and record pain intensity in an eDiary for at least 5 of the 7 daily morning measurements and at least 5 of the 7 daily evening measurements during the 7 days immediately before randomization.
4. Patient is ≥18 years of age, with a body mass index (BMI) between 18 and 32 kg/m$^2$, inclusive, at screening visit.

5. If the patient is a woman:
    a. The patient cannot become pregnant because she is surgically sterile (hysterectomy or tubal ligation) or postmenopausal for at least 6 months. OR
    b. If fertile, the patient is not pregnant and has negative pregnancy tests at both the screening and randomization visits and agrees to use an acceptable method of contraception (ie, oral contraceptives, hormone implant, intrauterine device, spermicide with barrier method, surgically sterile male sexual partner[s], or no sexual partners) for the duration of the study, including follow-up.
6. If the patient is a man:
    a. The patient is surgically sterile. OR
    b. If capable of producing offspring, the patient must agree to use a barrier method of contraception in combination with a spermicide with any female partner, unless the partner cannot become pregnant because she is surgically sterile (hysterectomy or tubal ligation), she has been postmenopausal for at least 6 months, or she is fertile but using an acceptable method of contraception (ie, oral contraceptives, hormone implant, or intrauterine device) for the duration of the study, including follow-up.
7. Patient must sign the written ICF for the study and be willing to comply with all study procedures and restrictions.
8. Patient must be judged by the investigator to be medically healthy (except for postherpetic neuralgia) and able to participate in the study.

Patient Exclusion Criteria

Patients will be excluded from participating in this study if they meet 1 or more of the following criteria:
1. Patient has any other severe pain that might confound assessment or self-evaluation of pain due to postherpetic neuralgia.
2. Patient has postherpetic neuralgia affecting the face (trigeminal nerve distribution).
3. Patient has a history, in the judgment of the investigator, of inadequate response to more than 2 adequate courses of treatment with other medications used to treat neuropathic pain (e.g., tricyclic antidepressants, serotonin-norepinephrine reuptake inhibitors, anticonvulsants, topical lidocaine, and/or topical capsaicin).
4. Patient is taking oral analgesics (either opioid or non-opioid) or is receiving topical therapy such as the 5% topical lidocaine patch for the treatment of pain and is unwilling or unable to complete a washout period during which the patient will discontinue analgesic therapy or topical pain therapy.
5. Patient has been treated with topical capsaicin at any time in the past 6 months for neuropathic pain.
6. Patient has an NRS score of 10 on 1 or more occasions during the baseline pain assessment interval (days −7 to −1) immediately before randomization or NRS scores of 9 on 3 or more occasions during the same time frame.
7. Patient used rescue medication during the 7-day baseline period.
8. Patient has a history of fibromyalgia.
9. Patient has uncontrolled cardiac, renal, hepatic, or other systemic disorders that, in the opinion of the investigator, may jeopardize the patient.
10. Patient uses Class Ic anti-arrhythmic drugs such as flecainide or propafenone.
11. Patient has a resting heart rate <45 or >100 beats per minute (bpm), QRS ≥120 milliseconds (including complete left and/or right bundle branch block), QT interval corrected for heart rate by Fridericia's formula (QTcF) ≤320 milliseconds or ≥470 milliseconds, and, for patients in sinus rhythm, PR <120 milliseconds or ≥220 milliseconds. (These numerical exclusion criteria will be applied using the mean values of 3 ECGs.)
12. Patient has second- or third-degree atrioventricular block unless treated with a permanent pacemaker.
13. Patient has uncontrolled atrial fibrillation or flutter (ventricular rate >100 bpm).
14. Patient has a congenital arrhythmia syndrome (e.g., Brugada syndrome or long or short QT syndrome).
15. Patient has had myocardial infarction within the past 12 months or current unstable angina, coronary ischemia, or heart failure.
16. Patient has significant edema or loss of skin integrity (including sores or ulcers) other than healed herpes zoster skin rash affecting the region of pain and surrounding area.
17. Patient is intolerant to study drug, its excipients, and/or acetaminophen.
18. Patient uses any over-the-counter (OTC) analgesic medication/topical therapy for the duration of the study except for permitted rescue (for postherpetic neuralgia pain) medications. Stable therapy of more than 30 days for aspirin (up to 81 mg/day) is allowed as cardiovascular prophylaxis.
19. Patient uses any non-pharmacologic pain management techniques (e.g., physical techniques, physiotherapy, massage therapy, acupuncture, biofeedback, and/or psychological support) and is unable or unwilling to discontinue prior to baseline pain assessment.
20. Patient uses any CYP3A4 or CYP2C19 inhibitors or substrates.
21. Patient uses any topical/cosmetic products (e.g., lotions and tanning products) on the skin in the painful region of postherpetic neuralgia.
22. Patient has a history of alcohol or drug abuse within 1 year before the screening visit, or a positive urine drug test at the screening visit for cocaine, marijuana, opioids, amphetamines, methamphetamines, benzodiazepines, barbiturates, methadone, and/or tricyclic antidepressants unless explained by the use of prescription medication. (The use of medical marijuana is not permitted and excludes the patient from the study.)
23. Patient is pregnant or breast-feeding at the time of the screening visit.
24. Patient has findings in laboratory data, vital signs measurements, or physical examination at the screening, baseline pain assessment interval, or randomization visit that, in the opinion of the investigator, may pose undue risk to the patient or may interfere with study data interpretation.
25. Patient was previously randomly assigned to treatment in this study and received/subsequently discontinued study drug.
26. Patient used another investigational drug within 30 days or 5 half-lives (whichever is longer) before the planned first day of study drug application (day 1) in this study.
27. Patient refuses to provide 2 blood samples at the screening visit for pharmacogenomic analyses.
28. Patient is a study center or Sponsor employee who is directly involved in the study or the relative of such an employee.
29. There is any other reason that would make the patient, in the opinion of either the investigator or the Sponsor, unsuitable for the study.

Restrictions

Patients will be required to comply with the following restrictions with respect to activity:

1. After applying ointment, patients should wait for 10 minutes before covering the area with clothing, to allow the ointment to be absorbed by the skin. After the ointment has fully penetrated the skin, the area will be dry.
2. After applying ointment, patients must not apply pressure to the area of skin treated with ointment by leaning against surfaces, such as furniture, for 10 minutes, to allow the ointment to be absorbed by the skin. After the ointment has fully penetrated the skin, the area will be dry.

In addition, patients must maintain (hold constant) their current level of physical activity from the baseline visit through the end of treatment (visit 5, day 29, week 4).

Prior and Concomitant Therapy or Medication

Any prior or concomitant therapy or medication that a patient has had within 90 days before study drug administration and up to the end of the study period, including follow-up, will be recorded on the CRF. Generic or trade name, indication, and dosage will be recorded. The Sponsor will encode all therapy and medication according to the World Health Organization drug dictionary (WHO Drug).

The following medications will not be allowed during this study:

1. Oral analgesics
2. Topical analgesics, including lidocaine (gels, creams and patches) and capsaicin patches
3. Medications that may cause DDIs
4. Rescue pain medication except permitted acetaminophen rescue
5. Class Ic anti-arrhythmic drugs such as flecainide or propafenone
6. At each clinic visit after the screening visit, the investigator will ask patients whether they have taken any medications (other than study drug), including OTC medications, vitamins, or herbal or nutritional supplements, since the previous visit. Indication, dosage, and start and end dates should be entered on the CRF.

Rescue Medications for Postherpetic Neuralgia Pain

Patients will be provided with acetaminophen (TYLENOL, McNeil Consumer Healthcare Division of McNEIL-PPC, Inc) as 325-mg tablets in bottles of 100 tablets and allowed to take 1 to 2 tablets per dose every 6 hours, as needed, and up to 6 tablets or 1950 mg per day (over a 24-hour period) for rescue relief of postherpetic neuralgia pain. Rescue medication will be provided at the screening visit. Rescue medication compliance will be checked at all visits until used rescue medication is collected after the baseline pain assessment interval for patients not continuing in the study, at visit 5 (day 29, week 4) for patients who complete the treatment period, or at the ET visit for patients who prematurely discontinue study drug.

No other rescue medications will be provided or allowed from the washout phone contact through visit 5 (day 29, week 4) or the ET visit. Patients will not be permitted to use rescue medication during the baseline pain assessment interval (days −10 through −1) and during the final week of treatment (the 7-day period before visit 5). During the washout interval, rescue medication use (dates of use and dose taken) will be recorded as concomitant medication. During baseline and the treatment period, rescue medication use will be recorded using the eDiary.

Total Blood Volume

The total amount of blood drawn during the study from each patient will be approximately 50 mL.

Assessment of Safety

In this study, safety will be assessed by qualified study staff by evaluating the following: reported adverse events, clinical laboratory test results, vital signs measurements, ECG findings, physical examination findings (including body weight measurements), dermal irritation findings, and concomitant medication usage.

Definition of an Adverse Event

An adverse event can include any of the following:

1. Intercurrent illnesses.
2. Physical injuries.
3. Events possibly related to concomitant medication.
4. Significant worsening (change in nature, severity, or frequency) of the disease under study or other pre-existing conditions. Note: A condition recorded as pre-existing that is intermittently symptomatic (e.g., headache) and that occurs during the study should be recorded as an adverse event.
5. Drug interactions.
6. Events occurring during diagnostic procedures or during any washout phase of the study.
7. Laboratory or diagnostic test abnormalities that result in the withdrawal of the patient from the study, are associated with clinical signs and symptoms or a serious adverse event, or require medical treatment or further diagnostic work-up, or are considered by the investigator to be clinically significant. Note: Abnormal laboratory test results at the screening visit that preclude a patient from entering the study or receiving study treatment are not considered adverse events but will be evaluated to monitor data from patients who do not meet screening criteria.
8. All events of possible drug-induced liver injury with hyperbilirubinemia (defined as aspartate aminotransferase [AST] or alanine aminotransferase [ALT]≥3 times the upper limit of the normal range [ULN] plus either bilirubin ≥2 times the ULN or International Normalized Ratio [INR]>1.5) or Hy's Law events require immediate study treatment cessation and reporting as a serious adverse event.

Severity of an Adverse Event

The severity of each adverse event must be recorded as 1 of the choices on the following scale:

Mild: No limitation of usual activities
Moderate: Some limitation of usual activities
Severe: Inability to carry out usual activities Definition of a Serious Adverse Event A serious adverse event is an adverse event occurring at any dose that results in any of the following outcomes or actions:

1. Death.
2. A life-threatening adverse event (i.e., the patient was at immediate risk of death from the event as it occurred); does not include an event that, had it occurred in a more severe form, might have caused death.
3. Inpatient hospitalization or prolongation of existing hospitalization means that hospital inpatient admission and/or prolongation of hospital stay were required for treatment of an adverse event or that they occurred as a consequence of the event. Hospitalizations scheduled for an elective procedure or for treatment of a pre-existing condition that has not worsened during participation in the study will not be considered serious adverse events.

4. Persistent or significant disability or incapacity (refers to a substantial disruption of one's ability to conduct normal life functions).
5. A congenital anomaly/birth defect.
6. An important medical event that may not result in death, be life-threatening, or require hospitalization but may jeopardize the patient and may require medical intervention to prevent one of the outcomes listed in this definition. Examples of such events are intensive treatment in an emergency room or at home for allergic bronchospasm, blood dyscrasias or convulsions that do not result in hospitalization, or the development of drug dependency or drug abuse. Note: Any suspected transmission of an infectious agent via a medicinal product is considered an important medical event.

An adverse event that does not meet any of the criteria for seriousness listed above will be regarded as a nonserious adverse event.

Pregnancy

All pregnancies (pregnancies of women participating in the study and female partners of men participating in the study) that occur during the study, or within 30 days of completion of the study, are to be reported immediately to the Sponsor.

Any patient becoming pregnant during the study will be withdrawn from study drug treatment. All patients (or female partners of male patients) who become pregnant will be monitored to the completion or termination of the pregnancy. If the pregnancy continues to term, the outcome (health of the infant up to 8 weeks of age), details of birth, and presence or absence of any birth defect, congenital abnormalities, or maternal and newborn complications will be reported to the Sponsor. Any complication of pregnancy will be reported as an adverse event or serious adverse event, as appropriate.

Chemical Laboratory

Clinical laboratory test (serum chemistry and hematology) and urinalysis will be performed at the time points indicated in Table 8. Specific laboratory tests to be performed are listed below:

The following serum chemistry tests will be performed:
  calcium
  phosphorus
  sodium
  potassium
  chloride
  bicarbonate or carbon dioxide
  glucose
  blood urea nitrogen (BUN)
  creatinine
  cholesterol
  uric acid
  ALT
  AST
  lactic dehydrogenase (LDH)
  gamma-glutamyl transpeptidase (GGT)
  alkaline phosphatase
  creatine phosphokinase
  total protein
  albumin
  total bilirubin
  direct bilirubin
  indirect bilirubin
The following hematology tests will be performed:
  hemoglobin
  hematocrit
  red blood cell (RBC) count
  platelet count
  absolute neutrophil count
  white blood cell (WBC) count and differential count
    polymorphonuclear leukocytes (neutrophils)
    lymphocytes
    eosinophils
    monocytes
    basophils
    atypical lymphocytes
Urinalysis will include testing for the following:
  protein
  glucose
  ketones
  blood (hemoglobin)
  pH
  specific gravity
  microscopic, as needed
    bacteria
    RBCs
    WBCs
    casts
    crystals
Other Clinical Laboratory Tests Other clinical laboratory tests will be performed to ensure the safety of the patients but will not be used to assess the safety of the study drug.

Pregnancy Tests

Urine pregnancy tests will be performed at the study site (with test kits provided by a central laboratory) for all women of child-bearing potential at screening (visit 1), randomization (visit 3, day 1), visit 4 (day 15±1, week 2), visit 5 (day 29, week 4), and at the follow-up/ET visit (visit 6, day 57±3). Any patient who becomes pregnant during the study will be withdrawn.

Urine Drug Screen

A urine drug screen will be performed at the time points indicated in Table 8. The urine drug screen includes a means to detect the presence of drugs prohibited according to the protocol, including cannabinoids, alcohol, cocaine, amphetamines, barbiturates, benzodiazepine, and opiates. If a parameter noted above cannot be tested using urine, an alternative matrix (e.g., serum) may be considered acceptable. The Sponsor's medical expert must be made aware in advance of, and provide approval for, drug screen parameters to which this will apply. A positive result for any of the above drugs or their metabolites, without medical explanation, will preclude the patient from enrollment or continued participation in the study.

Vital Signs

Vital signs will be measured at the time points indicated in Table 8. Vital signs include the following:
  heart rate
  respiration rate
  body temperature
  blood pressure
Electrocardiography A 12-lead ECG will be conducted as triplicate tracings taken at least 1 minute apart at the time points indicated in Table 8. To determine eligibility based upon numerical exclusion criteria of cardiac intervals, the investigator will use the mean values of 3 ECGs. A qualified physician at a central diagnostic center will be responsible for interpreting the ECG. Any ECG finding that is judged by the investigator as a clinically significant change (worsening) compared with a baseline value will be considered an adverse event, recorded on the source documentation and transcribed onto the CRF.

Physical Examinations

Physical examinations, including height (to be obtained at the screening visit only) and weight (screening and follow-up/ET visits only) will be performed at the time points indicated in Table 8. Any physical examination finding that is judged by the investigator as a clinically significant change (worsening) compared with a baseline value will be considered an adverse event, recorded on the CRF, and monitored.

Other Safety Measures and Variables: Concomitant Therapy or Medication

Concomitant therapy or medication usage will be monitored throughout the study.

Dermal Irritation Evaluation

Dermal irritation will be evaluated at the time points indicated in Table 8 using the scale below:
0=no evidence of irritation
1=minimal erythema (barely perceptible)
2=definite erythema, readily visible; minimal edema or minimal papular response
3=erythema and papules
4=definite edema
5=erythema, edema, and papules
6=vesicular eruption
7=strong reaction spreading beyond test site Pharmacodynamic Variables Pharmacodynamic endpoints assessed during the study are the secondary efficacy endpoints change from baseline in maximal intensity of patients' brush-evoked allodynia and change from baseline in maximal intensity of patients' punctate-evoked hyperalgesia.

Safety Variables

The overall safety and tolerability of topical 4% Test Pharmaceutical Composition and 8% Test Pharmaceutical Composition treatment will be assessed throughout the study by evaluating adverse events and the following additional safety variables at the time points specified in Table 8:
clinical laboratory tests
vital signs
physical examination
dermal irritation
12-lead ECGs
concomitant therapy or medication usage Expected Results The results of this study are expected to show that concentrations of the spiro-oxindole in the affected skin area where the 4% Test Pharmaceutical Composition or the 8% Test Pharmaceutical Composition of the invention was administered to the affected skin are of the subject are significantly higher than concentrations of the spiro-oxindole compound in the plasma of the subject following administration, thereby confirming that administration of a pharmaceutical composition of the invention results in minimal or negligible systemic exposure.

Furthermore, the results of this study are expected to show that the pharmaceutical compositions of the invention are effective in treating postherpetic neuralgia in the subjects.

Biological Example 5

An Open-Label, One-Sequence Drug-Drug Interaction Study in Healthy Subjects to Evaluate the Effects of Multiple-Dose Topical Treatment with the 8% Test Pharmaceutical Composition of the Invention on the Pharmacokinetics of Midazolam and Omeprazole The purpose of this study was to investigate whether topical administration to healthy subjects of a 8% pharmaceutical composition of the invention for 7.5 days affects the pharmacokinetics of single oral doses of midazolam (an known CYP3A4 substrate) or omeprazole (a known CYP2C19 substrate).

Primary Objectives:

The primary objectives of this study were to determine the effects of multiple-dose topical treatment with the 8% Test Pharmaceutical Composition on the single-dose pharmacokinetics of oral midazolam and to determine the effects of multiple-dose topical treatment with 8% Test Pharmaceutical Composition on the single-dose pharmacokinetics of oral omeprazole.

Secondary Objectives:

The secondary objectives of the study were to characterize the pharmacokinetics of the spiro-oxindole compound; to characterize the pharmacokinetics of midazolam and omeprazole major metabolites, 1-OH-midazolam and 5-OH-omeprazole; to evaluate the safety and tolerability of the 8% Test Pharmaceutical Composition administered twice daily (BID) for 7.5 days.

Number of Subjects (Planned and Analyzed):

For this study, 32 healthy subjects were planned to be enrolled; data from 32 subjects were analyzed for pharmacokinetics and safety.

Main Criteria for Inclusion:

Subjects were included in the study if all of the following main criteria were met:
1. Healthy male and/or female subjects aged 18 to 50 years, inclusive at the time of screening.
2. Body mass index (BMI) ≥18.0 and ≤32.0 kg/m2.
3. Able and willing to provide written informed consent.
4. Able and willing to comply with all study procedures and restrictions.

Main Criteria for Exclusion:

Subjects were excluded from participating in this study if one or more of the following main criteria were met (not all inclusive):
1. History or evidence of clinically significant illness or surgery within 4 weeks prior to day 1.
2. History or evidence of any clinically significant disease including neurological, dermatological, cardiovascular, endocrine, pulmonary, gastrological, renal, hepatobiliary, hematological, immunological, urologic, psychiatric, metabolic or other major disease. Subjects with Gilbert's syndrome could be included.
3. Presence of open wounds, sunburn, tattoo, major scarring, non-intact or damaged skin (eg, resulting from exudative dermatitis, eczema, acne, infected lesion, burns) in the proposed application area, presence of significant pain, neuropathy, venous stasis or any other condition in the proposed application area that, in the opinion of the investigator, would have interfered with the application of the study drug treatments.
4. Missing or amputated limb (eg, foot, hand, arm, leg).
5. Any clinically significant abnormality (including clinically significant laboratory test result) found at screening or day −1.
6. Pregnant or nursing females (including positive pregnancy test at screening or day −1).
7. Overabundance of hair on the back and/or legs that, in the opinion of the investigator, would have precluded the effective application of study drug to the application area(s). Trimming the hair was permissible by the medical staff prior to enrollment as long as there was no shaving, no waxing, and the trimming blades were not directly on the skin.

Study Drug Dose, Mode of Administration, and Administration Rate:

8% Test Pharmaceutical Composition applied to 53% of body surface area (BSA) BID for 7.5 days.

Other Drugs:

Commercially available midazolam syrup (3 mg) and omeprazole (20 mg delayed-release capsule) were coadministered orally on days 1 and 9, with the day 9 doses administered 1 hour after the final dose of 8% Test Pharmaceutical Composition.

Method of Blinding:

This was an open-label study with no blinding.

Duration of Treatment:

Up to 64 days per subject (including an up to 28-day screening period).

General Design and Methodology:

This was a single center, open-label, 1-sequence drug-drug interaction study in 32 healthy adult male and female subjects. The study consisted of a 28-day screening period, a 10-day inpatient treatment period, and a follow-up visit. Subjects meeting the study inclusion/exclusion requirements were admitted to the clinical research unit on day −1 and were confined until day 10.

Primary Pharmacokinetic Variables and Endpoints:

Blood samples were collected for the assessment of the pharmacokinetics of midazolam and omeprazole. The primary pharmacokinetic variables for midazolam and omeprazole were maximum observed plasma drug concentration ($C_{max}$), area under the plasma concentration-time curve from time 0 to the time of the last measurable concentration ($AUC_{0-t}$), and area under the plasma concentration-time curve from time 0 to extrapolated to infinity ($AUC_{0-inf}$) on days 1 and 9.

The primary pharmacokinetic endpoints were the geometric mean ratios (90% confidence intervals [CIs]) for $C_{max}$, $AUC_{0-t}$, and $AUC_{0-inf}$ for midazolam and omeprazole on day 9 versus day 1.

Secondary Pharmacokinetic Measures and Endpoints:

The secondary pharmacokinetic parameters for midazolam and omeprazole were time to maximum observed plasma drug concentration ($t_{max}$), apparent oral clearance (CL/F), apparent terminal elimination rate constant ($\lambda_z$), apparent terminal half-life ($t_{1/2}$), and percentage extrapolated AUC ($AUC_{ext}$).

Blood samples were collected for the assessment of the pharmacokinetics of the major metabolites of midazolam (1-OH-midazolam) and omeprazole (5-OH-omeprazole), and for the spiro-oxindole compound. Further secondary pharmacokinetic variables included $C_{max}$, $t_{max}$, $AUC_{0-t}$, $AUC_{0-inf}$, CL/F, $\lambda_z$, $t_{1/2}$, and % $AUC_{ext}$ for 1-OH-midazolam and 5-OH-omeprazole, on days 1 and 9, and $C_{max}$, morning predose concentrations ($C_{trough}$), average plasma concentration over the dosing interval ($C_{ave}$), and area under the plasma concentration-time curve over the dosing interval ($AUC_{0-\tau}$) were presented for the spiro-oxindole compound.

Safety Variables:

Safety was assessed by adverse events (including deaths, serious adverse events, and withdrawals due to adverse events), results of clinical laboratory tests (serum chemistry, hematology, and urinalysis), vital signs (blood pressure, pulse, and oral body temperature), pulse oximetry, 12-lead electrocardiogram (ECG) results, physical examination findings, dermal irritation, and concomitant medication usage.

Pharmacogenomic Variables:

Blood samples were collected for the assessment of cytochrome P450 family 2, subfamily C, polypeptide 19 (CYP2C19) metabolic status of subjects.

Statistical Considerations:

A. Analysis Populations

Three analysis sets were defined for analysis purposes:
1. The enrolled set included all subjects who passed screening procedures.
2. The pharmacokinetic analysis set included all subjects in the safety analysis set (as defined below) who had at least 1 measurable concentration of midazolam, omeprazole, or their metabolites, or the spiro-oxindole compound.
3. The safety analysis set included all subjects who received at least 1 dose of study drug. In this analysis set, treatment was assigned based upon the treatment subjects actually received.

B. Sample Size and Power Considerations

A total of 32 subjects were planned to be enrolled in the study, with the intent that at least 28 subjects would complete the study. The within-subject coefficient of variation (% CV) for midazolam pharmacokinetic parameters ($C_{max}$, AUC) was estimated to be 21%. Assuming a within-subject CV of 21% and an expected true ratio of 1.05 for day 9 versus day 1, a total of 28 subjects completing the study would provide at least 90% power to detect bioequivalence in a single pharmacokinetic parameter of midazolam before and after multiple administration of the spiro-oxindole compound at the 0.05 significance level for a 1-sided test. Assuming a 10% to 20% discontinuation rate, 4 additional subjects were included so that a total of 32 subjects were enrolled in this study. This sample size also provided approximately 86% power to detect bioequivalence in a single omeprazole pharmacokinetic parameter (AUC) before and after multiple administration of the spiro-oxindole compound at the 0.05 significance level, assuming a within-subject CV of 26% and an expected true ratio of 1.0. SAS® proc power was used for sample size calculation.

Pharmacokinetic Analyses:

Descriptive statistics (n, mean, geometric mean, standard deviation [SD], % CV, median, minimum, and maximum) were used to summarize plasma midazolam, omeprazole and their metabolites, and the spiro-oxindole compound concentration for all subjects overall at each scheduled time point. Descriptive statistics (as noted above) were also used to summarize plasma omeprazole, 5-OH-omeprazole, and the spiro-oxindole compound concentration for all subjects overall by CYP2C19 genotype at each scheduled time point. Pharmacokinetic parameters were derived by noncompartmental analysis. Descriptive statistics (as noted above) were used to summarize the calculated pharmacokinetic parameters for midazolam, omeprazole and their metabolites, and the spiro-oxindole compound by treatment for all subjects. Descriptive statistics (as noted above) were also used to summarize the calculated pharmacokinetic parameters for omeprazole, 5-OH-omeprazole, and the spiro-oxindole compound by treatment and CYP2C19 genotype. Plots of geometric mean and individual plasma concentrations and of select pharmacokinetic parameters for midazolam, omeprazole and their metabolites and the spiro-oxindole compound at select sampling times were provided. Additionally, plots of individual select pharmacokinetic parameters by CYP2C19 phenotype for omeprazole at select time points were provided.

Safety Analyses:

The overall safety and tolerability of midazolam, omeprazole, and the 8% Test Pharmaceutical Composition was assessed throughout the study by monitoring adverse events, clinical laboratory tests, vital signs, peripheral oxygen saturation (SpO$_2$), safety 12-lead ECGs, physical examination findings, dermal irritation, and concomitant medication usage. Descriptive statistics for continuous variables included n, mean, SD, standard error [SE], median, minimum, and maximum. Number of subjects and percentages were used for the description of adverse events and other categorical variables.

Pharmacogenomic Analyses:

Pharmacogenomic data were listed.

Summary of Results

A. Subject Disposition and Demography

A total of 94 healthy subjects were screened for enrollment into this study. Of the 94 subjects screened, 32 subjects at 1 center in the USA met entry criteria and were considered to be eligible for enrollment into the study. Of the 62 subjects who were not enrolled, 4 subjects were excluded on the basis of inclusion criteria, 47 subjects were excluded on the basis of exclusion criteria, 3 subjects withdrew consent, 1 subject was lost to follow up before the baseline visit, and 7 subjects were excluded based on "Other" reasons. Of the 32 subjects enrolled, all received at least 1 administration of study drug and were evaluated for safety and pharmacokinetics. The planned number of 32 subjects was met. One subject withdrew from the study due to an adverse event. There were more males (27 [84%]) than females (5 [16%]). Most of the subjects were not Hispanic or Latino (27 [84%] subjects) and most were either white (13 [41%] subjects) or black (18 [56%] subjects). Subjects had a mean age of 35.1 years (range: 19 to 50 years), a mean weight of 76.81 kg (range: 54.1 to 98.5 kg), a mean height of 173.92 cm (range: 155.0 to 188.0 cm), a mean BMI of 25.42 kg/m2 (range: 19.2 to 32.0 kg/m2), and a mean BSA of 1.92 m2 (range: 1.6 to 2.3 m2). With regards to CYP2C19 phenotype, subjects were evenly distributed for ultra-rapid, extensive, and intermediate metabolizers (10 [31%] subjects each). Only 2 (6%) subjects were classified as poor metabolizers.

B. Pharmacokinetics Results

1. Midazolam/1-OH-Midazolam

Mean plasma midazolam concentrations were similar with or without coadministration of the spiro-oxindole compound. On both days 1 and 9, midazolam appeared to be rapidly absorbed as it was quantifiable in all subjects by 0.25 hours postdose. Upon reaching a peak, midazolam concentrations declined steadily in a multiphasic manner. Most subjects had measurable concentrations through to at least 16 hours postdose.

On day 1 after oral administration of a single dose of 3 mg midazolam and 20 mg omeprazole, midazolam was rapidly absorbed, reaching $t_{max}$ at a median time of 0.63 hours on day 1 and 0.75 hours on day 9. Midazolam systemic exposure parameters ($C_{max}$ and AUC) were similar on both days 1 and 9. $C_{max}$ was 16.95 ng/mL on day 1 compared to 14.60 ng/mL on day 9. Over a 24-hour period postdose, $AUC_{0-t}$ reached a geometric mean value of 42.24 hr*ng/mL on day 1 and 39.36 hr*ng/mL on Day 9. $AUC_{0-inf}$ was 43.80 hr*ng/mL on Day 1 and 40.73 hr*ng/mL on day 9. In both cases, $AUC_{0-t}$ accounted for >95% of the $AUC_{0-inf}$.

Selected parameters of midazolam systemic exposure on day 1 were compared to corresponding parameters on day 9 and the results are summarized in Table 9 below. The ratio of the geometric means for $C_{max}$, $AUC_{0-t}$, and $AUC_{0-inf}$ on day 9 (7.5 days of treatment with 8% Test Pharmaceutical Composition) to day 1 (no 8% Test Pharmaceutical Composition) were 86.169, 93.657, and 93.381, respectively. The 90% CIs for $AUC_{0-t}$ and $AUC_{0-inf}$ were entirely contained within the predetermined range of 80% to 125%. However, for $C_{max}$, the lower bound of the 90% CI was slightly outside this range. These data indicate that the spiro-oxindole compound had no relevant effect on midazolam pharmacokinetics.

TABLE 9

Statistical Analysis of the Effect of the Spiro-Oxindole Compound on Midazolam Pharmacokinetic Parameters (Pharmacokinetic Analysis Set)

| Treatment | Pharma-cokinetic parameter | Geometric LS mean ration (%) (test/reference) | 90% CI of ratio (%) (test/reference) |
|---|---|---|---|
| Midazolam with spiro-oxindole compound (test) versus midazolam without spiro-oxindole compound (reference) | $AUC_{0-inf}$ $AUC_{0-t}$ $C_{max}$ | 93.381 93.657 86.169 | (87.752, 99.370) (87.982, 99.699) (78.658, 94.397) |

CI = confidence interval; LS = least squares.

Mean plasma 1-OH-midazolam concentrations were similar with or without coadministration of the spiro-oxindole compound. On both days 1 and 9, 1-OH-midazolam was quantifiable by 0.25 hours. Upon reaching a peak, mean 1-OH-midazolam concentrations declined steadily in a multiphasic manner. Most subjects had measurable concentrations through to at least 16 hours postdose. Concentrations of the 1-OH metabolite were less than parent midazolam.

On both days 1 and 9, midazolam was rapidly metabolized with its 1-OH metabolite reaching $t_{max}$ at a median time of 0.75 hours. Systemic exposure parameters ($C_{max}$ and AUC) for 1-OH-midazolam were similar on both days 1 and 9. Geometric mean $C_{max}$ was 7.33 ng/mL on day 1 and 6.67 ng/mL on day 9. Geometric $AUC_{0-t}$ and $AUC_{0-inf}$ were 15.82 and 16.83 hr*ng/mL, respectively on day 1, and 17.18 hr*ng/mL and 17 92 hr*ng/mL on day 9. On both days, $AUC_{0-t}$ accounted for >94% of $AUC_{0-inf}$. Systemic exposure to 1-OH-midazolam was lower than that of parent midazolam on both days 1 and 9. The half-life of 1-OH-midazolam was similar to that of parent midazolam, and was also similar from day 1 and day 9. Geometric mean $t_{1/2}$ was 4.39 hours and 4.68 hours on days 1 and 9, respectively. These data suggest that concomitant administration of the spiro-oxindole compound had no relevant effect on systemic exposure to 1-OH-midazolam.

2. Omeprazole and 5-OH-Omeprazole

Mean plasma omeprazole concentrations were similar with or without coadministration of the spiro-oxindole compound. On both days 1 and 9, 0.75 to 1.5 hours elapsed before omeprazole concentrations were quantifiable in a majority of subjects. Upon reaching a peak, omeprazole concentrations declined steadily in a multiphasic manner until no longer quantifiable, which was between 9 to 12 hours in most subjects. In a few subjects, omeprazole remained quantifiable until 16 to 24 hours.

After oral administration of a single dose of 3 mg midazolam and 20 mg omeprazole, omeprazole was absorbed reaching tmax at median times of 2.0 and 2.5 hours on days 1 and 9, respectively. Systemic exposure parameters ($C_{max}$ and AUC) for omeprazole were similar on both days 1 and 9. Geometric mean $C_{max}$ was 227.39 ng/mL on day 1 and 227.04 ng/mL on day 9. On day 1, geometric mean $AUC_{0-t}$ and $AUC_{0-inf}$ were 545.29 and 634.65 hr*ng/mL, respectively, while on day 9, they were 556.16 and 633.97 hr*ng/mL, respectively. On both days, $AUC_{0-t}$ accounted for >99% of $AUC_{0-inf}$.

Selected parameters of omeprazole systemic exposure on day 1 were compared to corresponding parameters on day 9, and the results are summarized in Table 10 below. The ratios of the geometric means for $C_{max}$, $AUC_{0-t}$, and $AUC_{0-inf}$ on day 9 (7.5 days of treatment with 8% Test Pharmaceutical Composition) to day 1 (no 8% Test Pharmaceutical Composition) were 98.939, 101.553, and 105.751, respectively. The 90% CIs for $AUC_{0-t}$, and $AUC_{0-inf}$ were entirely contained with the predetermined range of 80% to 125%. These data suggest that the spiro-oxindole compound had no relevant effect on omeprazole pharmacokinetics. Mean 5-OH-omeprazole plasma concentrations were similar with or without coadministration of the spiro-oxindole compound. On both days 1 and 9, 0.75 to 1.5 hours elapsed before 5-OH-omeprazole concentrations were quantifiable in a majority of subjects. Upon reaching a peak, 5-OH-omeprazole concentrations declined steadily in a multiphasic manner until no longer quantifiable, which was 12 hours in most subjects. In a few subjects, 5-OH-omeprazole remained quantifiable until 16 hours. Concentrations of the 5-OH metabolite were less than those of parent omeprazole.

TABLE 10

Statistical Analysis of the Effect of the Spiro-Oxindole Compound on Omeprazole Pharmacokinetic Parameters (Pharmacokinetic Analysis Set)

| Treatment | Pharmacokinetic parameter | Geometric LS mean ration (%) (test/reference) | 90% CI of ratio (%) (test/reference) |
|---|---|---|---|
| Omeprazole with spiro-oxindole compound (test) versus midazolam without spiro-oxindole compound (reference) | $AUC_{0-inf}$ | 105.751 | (97.426, 114.787) |
| | $AUC_{0-t}$ | 101.553 | (93.656, 110.116) |
| | $C_{max}$ | 98.939 | (86.061, 113.745) |

CI = confidence interval; LS = least squares.

On both days 1 and 9, omeprazole was metabolized to its 5-OH metabolite. On day 1, $t_{max}$ of 5-OH-omeprazole was reached at a median time of 2.00 hours, while on day 9, median $t_{max}$ was 2.5 hours. Systemic exposure parameters ($C_{max}$ and AUC) for 5-OH-omeprazole were similar on both days 1 and 9. Geometric mean for $C_{max}$ was 148.71 ng/mL on day 1 and 142.30 ng/mL on day 9. Geometric $AUC_{0-t}$ and $AUC_{0-inf}$ were 436.73 and 447.15 hr*ng/mL, respectively, on day 1, and 430.54 hr*ng/mL and 439.66 hr*ng/mL on day 9. On both days, $AUC_{0-t}$ accounted for >98% of $AUC_{0-inf}$. Variability of systemic exposure was low on both days 1 and 9, with % CVs ranging from 22.7% to 36.7%. Half-life of 5-OH-omeprazole was similar on day 1 compared to day 9. Geometric mean $t_{1/2}$ was 1.55 and 1.53 hours on days 1 and 9, respectively. These data suggest that concomitant administration of the spiro-oxindole compound had no relevant effect on systemic exposure to 5-OH-omeprazole.

3. Spiro-Oxindole Compound

A total of 17 of 32 subjects had quantifiable levels of the spiro-oxindole compound in the predose sample on day 2 ranging from 35.8 to 455.5 pg/mL. The reason for the presence of measurable concentrations on the first day of dosing with the spiro-oxindole compound is unknown. All subjects had quantifiable plasma concentrations of the spiro-oxindole compound by day 3. On days 3 to 7, mean trough concentrations increased each successive day indicating that steady state had not been achieved after 7.5 days of dosing.

On day 9, concentrations were highly variable over the first 24 hours, often reaching multiple peaks. All 31 subjects had quantifiable concentrations at 24 hours postdose (mean 11651.61 pg/mL) and at the follow-up visit (360±24 hours; mean 326.29 pg/mL). Over the period of 24 hours from the final application of the 8% Test Pharmaceutical Composition, concentrations varied from a geometric mean $C_{trough}$ predose value) of 12760.52 pg/mL to a $C_{max}$ of 15072.40 pg/mL. For the first 12 hours after the final application (equivalent to the 8% Test Pharmaceutical Composition dosing interval from days 2 to 9), geometric mean $AUC_{0-12}$ was 132906.66 hr*pg/mL, with an average concentration of 11075.55 pg/mL over this 12-hour period, which coincided with the oral administration of midazolam and omeprazole.

There was no apparent relationship of the spiro-oxindole compound exposure with CYP2C19 phenotype.

Variability of the spiro-oxindole compound systemic exposure on day 9 was moderate, with % CV values ranging from 56.3% to 66.8%.

Conclusions:

Midazolam, the model substrate for CYP3A4, was coadministered with multiple doses of the spiro-oxindole compound. There was no evidence of a clinically meaningful effect of a topical formulation of the spiro-oxindole compound under exaggerated dosing conditions on the pharmacokinetics of oral midazolam, a sensitive probe CYP3A4 substrate, or its metabolite 1-OH-midazolam.

Omeprazole, the model substrate for CYP2C19, was coadministered with multiple doses of the spiro-oxindole compound. There was no evidence of a significant effect of topical formulation of the spiro-oxindole compound under exaggerated dosing conditions on the pharmacokinetics of oral omeprazole, a sensitive probe CYP2C19 substrate, or its metabolite 5-OH-omeprazole.

After topical application under exaggerated dosing conditions, the spiro-oxindole compound was very slowly absorbed and did not reach steady state within 7.5 days of BID dosing.

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A method of treating postherpetic neuralgia in a mammal, wherein the method comprises periodically administering to an affected skin area of the mammal a topical pharmaceutical composition comprising one or more excipients and a therapeutically effective amount of a spiro-oxindole compound having the following formula:

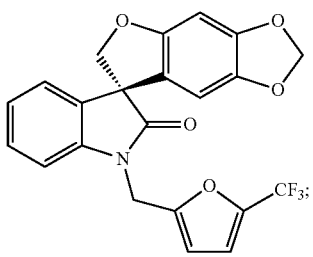 [SMILES: O=C1N(Cc2ccc(C(F)(F)F)o2)c2ccccc2[C@]12COc1cc3c(cc12)OCO3]

wherein:
(a) the periodic administration results in minimal or negligible systemic exposure of the spiro-oxindole compound where the minimal or negligible systemic exposure occurs when the concentration of the spiro-oxindole compound in the plasma and tissues of the mammal is from about 5-fold to about 100-fold less than the concentration of the spiro-oxindole compound in the affected skin area after administration of the topical pharmaceutical to the affected skin area;
(b) the periodic administration results in a greater concentration of the spiro-oxindole compound in the affected skin area than the concentration of the spiro-oxindole compound in the plasma of the mammal;
(c) the periodic administration is once a day, twice a day, three times a day or four times a day; and
(d) the topical pharmaceutical composition is periodically administered to the affected skin in a dose volume of from about 1.0 μL/cm² to about 9.0 μL/cm².

2. The method of claim 1, wherein the topical pharmaceutical composition comprises 2% to 8% (w/w) of the spiro-oxindole compound.

3. The method of claim 1 wherein the topical pharmaceutical composition comprises 45% to 55% (w/w) PEG 400; 5% to 15% (w/w) diethylene glycol monoethyl ether; 2.5% to 7.5% (w/w) oleyl alcohol; 2.5% to 7.5% (w/w) isopropyl myristate; 0.1% w/w to 7.5% (w/w) stearyl alcohol; 0.05% to 1% (w/w) butylated hydroxytoluene; and 15% to 30% (w/w) PEG 3350.

4. The method of claim 1, wherein the topical pharmaceutical composition comprises 2.0% (w/w) of the spiro-oxindole compound; 52.9% (w/w) PEG 400; 10% (w/w) diethylene glycol monoethyl ether; 5% (w/w) oleyl alcohol; 5% (w/w) isopropyl myristate; 5% (w/w) stearyl alcohol; 0.1% (w/w) butylated hydroxytoluene; and 20% (w/w) PEG 3350.

5. The method of claim 1, wherein the topical pharmaceutical composition comprises 4.0% (w/w) of the spiro-oxindole compound; 50.9% (w/w) PEG 400; 10% (w/w) diethylene glycol monoethyl ether; 5% (w/w) oleyl alcohol; 5% (w/w) isopropyl myristate; 5% (w/w) stearyl alcohol; 0.1% (w/w) butylated hydroxytoluene; and 20% (w/w) PEG 3350.

6. The method of claim 1, wherein the topical pharmaceutical composition comprises 8.0% (w/w) of the spiro-oxindole compound; 46.9% (w/w) PEG 400; 10% (w/w) diethylene glycol monoethyl ether; 5% (w/w) oleyl alcohol; 5% (w/w) isopropyl myristate; 5% (w/w) stearyl alcohol; 0.1% (w/w) butylated hydroxytoluene; and 20% (w/w) PEG 3350.

7. The method of claim 1 wherein the periodic administration is once a day.

8. The method of claim 1 wherein the periodic administration is twice a day.

9. The method of claim 1 wherein the dose volume is from about 1.0 μL/cm² to about 4.0 μL/cm² of skin.

10. The method of claim 9 wherein the dose volume is 3.0 μL/cm².

11. The method of claim 1 wherein the therapeutically effective amount of the topical pharmaceutical composition is from about 500 mg to about 2000 mg per each periodic administration to the affected skin area.

12. The method of claim 11 wherein the therapeutically effective amount of the topical pharmaceutical composition is about 1200 mg per each periodic administration to the affected skin area.

13. The method of claim 1 wherein the therapeutically effective amount of the topical pharmaceutical composition is effective in reducing the severity of the postherpetic neuralgia or alleviating the postherpetic neuralgia.

14. The method of claim 1 wherein the mammal is human.

15. The method of claim 1 wherein the periodic administration of the topical pharmaceutical composition is effective in reducing a daily average postherpetic neuralgia intensity or severity in the affected skin area in the human.

16. The method of claim 15 wherein the periodic administration of the topical pharmaceutical composition is effective in reducing the intensity or severity of the postherpetic neuralgia in the affected skin area as assessed by a NRS, NPSI, DSIS, NePIQoL and/or PGIC score.

17. The method of claim 16 wherein the periodic administration of the topical composition is effective in reducing the intensity or severity of the postherpetic neuralgia by 30% when compared to the baseline intensity or severity of the postherpetic neuralgia.

18. The method of claim 16 wherein the periodic administration of the topical composition is effective in reducing the intensity or severity of the postherpetic neuralgia by 50% when compared to the baseline intensity or severity of the postherpetic neuralgia.

19. A method of locally treating postherpetic neuralgia in a mammal with a minimal or negligible systemic exposure to a spiro-oxindole compound having the following formula:

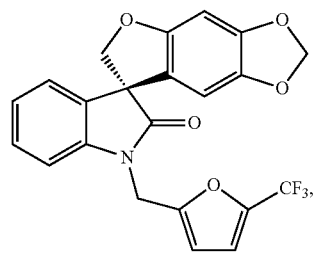 [SMILES: O=C1N(Cc2ccc(C(F)(F)F)o2)c2ccccc2[C@]12COc1cc3c(cc12)OCO3]

wherein the method comprises increasing the concentration of the Spiro-oxindole compound to a therapeutically effective amount in an affected skin area in the mammal by periodically administering to the affected skin area a topical pharmaceutical composition comprising one or more excipients and a therapeutically effective amount of the spiro-oxindole compound.

20. The method of claim 19 wherein the mammal is a human.

21. A method of treating postherpetic neuralgia in a mammal, wherein the method comprises periodically administering to an affected skin area of the mammal a topical pharmaceutical composition comprising one or more excipients and a therapeutically effective amount of a spiro-oxindole compound having the following formula:

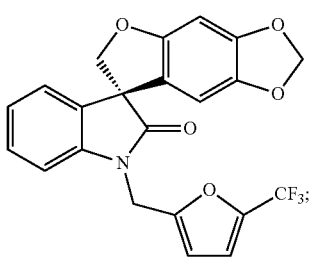 [SMILES: O=C1N(Cc2ccc(C(F)(F)F)o2)c2ccccc2[C@]12COc1cc3c(cc12)OCO3]

and a therapeutically effective amount of one or more other therapeutic agents; wherein:

(a) the periodic administration results in minimal or negligible systemic exposure of the spiro-oxindole compound where the minimal or negligible systemic exposure occurs when the concentration of the spiro-oxindole compound in the plasma and tissues of the mammal is from about 5-fold to about 100-fold less than the concentration of the spiro-oxindole compound in the affected skin area after administration of the topical pharmaceutical to the affected skin area;

(b) the periodic administration results in a greater concentration of the spiro-oxindole compound in the affected skin area than the concentration of the spiro-oxindole compound in the plasma of the mammal;

(c) the periodic administration is once a day, twice a day, three times a day or four times a day; and (d) the topical pharmaceutical composition is periodically administered to the affected skin in a dose volume of from about 1.00 µL/cm$^2$ to about 9.0 µl/cm$^2$.

22. The method of claim 21 wherein the one or more other therapeutic agent is acetaminophen.

* * * * *

UNITED STATES PATENT AND TRADEMARK OFFICE
CERTIFICATE OF CORRECTION

PATENT NO. : 9,682,033 B2
APPLICATION NO. : 15/016921
DATED : June 20, 2017
INVENTOR(S) : Michael Fetell et al.

Page 1 of 1

It is certified that error appears in the above-identified patent and that said Letters Patent is hereby corrected as shown below:

Item (56):
Column 1, Page 4, Line 4 "Coppola, "*N*-Acylation of Isatins. A Direct Route to *N*-Arylisatoic Anhydrides," *J. Heterocyclic Chem.* 24: 1249-1251, September/October 1987." should read, --Coppola, "*N*-Arylation of Isatins. A Direct Route to *N*-Arylisatoic Anhydrides," *J. Heterocyclic Chem.* 24: 1249-1251, September/October 1987.--.

Item (56):
Column 1, Page 9, Line 34 "Weidmann et al., "2-[(2-Pyridylmethyl)sulfinyl]-1*H*-thieno[3,4-*d*]imidazoles. A Novel Class of Gastric $H^+/K^+$-ATPase Inhibitors, *Med. Chem.* 35: 438-450, 1992." should read, --Weidmann et al., "2-[(2-Pyridylmethyl)sulfinyl]-1*H*-thieno[3,4-*d*]imidazoles. A Novel Class of Gastric $H^+/K^+$-ATPase Inhibitors," *J. Med. Chem.* 35: 438-450, 1992.--.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*